United States Patent
Cullis et al.

(10) Patent No.: US 8,859,768 B2
(45) Date of Patent: Oct. 14, 2014

(54) HETEROARYLS AND USES THEREOF

(75) Inventors: Courtney A. Cullis, Bedford, MA (US); Krista E. Granger, Medford, MA (US); Jianping Guo, Winchester, MA (US); Masaaki Hirose, Kanagawa (JP); Gang Li, Westborough, MA (US); Miho Mizutani, Cambridge, MA (US); Tricia J. Vos, Winchester, MA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 13/206,671

(22) Filed: Aug. 10, 2011

(65) Prior Publication Data

US 2012/0142732 A1    Jun. 7, 2012

Related U.S. Application Data

(60) Provisional application No. 61/372,553, filed on Aug. 11, 2010, provisional application No. 61/372,628, filed on Aug. 11, 2010, provisional application No. 61/469,157, filed on Mar. 30, 2011.

(51) Int. Cl.

| | |
|---|---|
| C07D 239/02 | (2006.01) |
| C07D 241/02 | (2006.01) |
| C07D 213/22 | (2006.01) |
| C07D 413/00 | (2006.01) |
| C07D 401/00 | (2006.01) |
| A61K 31/505 | (2006.01) |
| A61K 31/44 | (2006.01) |
| A61K 31/42 | (2006.01) |
| A61K 31/422 | (2006.01) |
| C07D 413/14 | (2006.01) |
| C07D 417/14 | (2006.01) |
| C07D 413/04 | (2006.01) |

(52) U.S. Cl.
CPC ............ *A61K 31/422* (2013.01); *C07D 413/14* (2013.01); *C07D 417/14* (2013.01); *C07D 413/04* (2013.01)
USPC ........ 544/298; 544/406; 546/257.4; 546/256; 546/268.4; 546/271.4; 514/269; 514/336; 514/340; 514/374; 514/333

(58) Field of Classification Search
USPC .............. 544/298, 406; 546/257.4, 256, 268, 546/271.4; 514/269, 336, 340, 374, 333, 514/342
See application file for complete search history.

(56) References Cited

U.S. PATENT DOCUMENTS

| | | |
|---|---|---|
| 3,257,203 A | 6/1966 | Sus et al. |
| 3,821,384 A | 6/1974 | Ariyan et al. |
| 3,852,293 A | 12/1974 | Ariyan et al. |
| 4,371,607 A | 2/1983 | Donges |
| 5,134,142 A | 7/1992 | Matsuo et al. |
| 6,015,826 A | 1/2000 | Pechacek et al. |
| 6,608,087 B1 | 8/2003 | Charifson et al. |
| 6,984,652 B2 | 1/2006 | Yager et al. |
| 7,074,801 B1 | 7/2006 | Yoshida et al. |
| 7,405,235 B2 | 7/2008 | Levy et al. |
| 7,504,513 B2 | 3/2009 | Boylan et al. |
| 7,741,348 B2 | 6/2010 | Nan et al. |
| 8,440,664 B2 | 5/2013 | Cardin et al. |
| 8,586,582 B2 | 11/2013 | Liang et al. |
| 2002/0022729 A1 | 2/2002 | Kawai et al. |
| 2003/0096816 A1 | 5/2003 | Cao et al. |
| 2004/0116425 A1 | 6/2004 | Li et al. |
| 2004/0198773 A1 | 10/2004 | Hart et al. |
| 2004/0248896 A1 | 12/2004 | Dean et al. |
| 2005/0004122 A1 | 1/2005 | Brown et al. |
| 2005/0054697 A1 | 3/2005 | Yager et al. |
| 2005/0124678 A1 | 6/2005 | Levy et al. |
| 2006/0041006 A1 | 2/2006 | Ibrahim et al. |
| 2006/0074119 A1 | 4/2006 | Andrews et al. |

(Continued)

FOREIGN PATENT DOCUMENTS

| | | |
|---|---|---|
| DE | 275870 A1 | 2/1990 |
| EP | 0853083 A1 | 7/1998 |

(Continued)

OTHER PUBLICATIONS

Laszlo et al. (bioorganic & Medical Chemistry Letters 8(1998) 2689-2694).*

(Continued)

*Primary Examiner* — Shirley V Gembeh
(74) *Attorney, Agent, or Firm* — Choate, Hall & Stewart LLP; Andrea L. C. Reid

(57) ABSTRACT

This invention provides compounds of formula IA or IB:

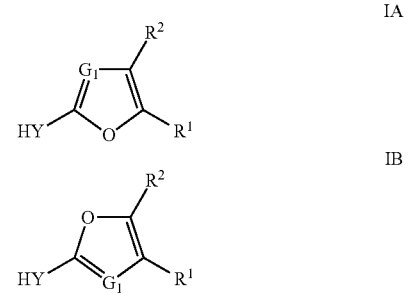

wherein HY, $R^1$, $R^2$, and $G_1$, are as described in the specification. The compounds are inhibitors of VPS34 and/or PI3K and are thus useful for treating proliferative, inflammatory, or cardiovascular disorders.

28 Claims, No Drawings

(56) References Cited

U.S. PATENT DOCUMENTS

| | | |
|---|---|---|
| 2006/0199804 A1 | 9/2006 | Hummersone et al. |
| 2007/0203210 A1 | 8/2007 | Boylan et al. |
| 2008/0021217 A1 | 1/2008 | Borchardt et al. |
| 2008/0045570 A1 | 2/2008 | Brenchley et al. |
| 2008/0132546 A1 | 6/2008 | Basarab et al. |
| 2008/0255120 A1 | 10/2008 | Lin et al. |
| 2008/0293716 A1 | 11/2008 | Drewry et al. |
| 2008/0306060 A1 | 12/2008 | Alexander et al. |
| 2009/0012031 A1 | 1/2009 | Chinnaiyan et al. |
| 2009/0030016 A1 | 1/2009 | Gandhi et al. |
| 2009/0036435 A1 | 2/2009 | Curry et al. |
| 2009/0247567 A1 | 10/2009 | Do et al. |
| 2009/0325925 A1 | 12/2009 | Renou et al. |
| 2010/0075951 A1 | 3/2010 | Cardin et al. |
| 2010/0256172 A1 | 10/2010 | Shi et al. |
| 2010/0267759 A1 | 10/2010 | Seefeld et al. |
| 2011/0003806 A1 | 1/2011 | Hirose et al. |
| 2011/0003807 A1 | 1/2011 | Banno et al. |
| 2011/0021531 A1 | 1/2011 | Chobanian et al. |
| 2012/0172345 A1 | 7/2012 | Freeze et al. |
| 2012/0178723 A1 | 7/2012 | Hirose et al. |
| 2012/0214794 A1 | 8/2012 | Freeze et al. |
| 2013/0165464 A1 | 6/2013 | Chau et al. |
| 2013/0165472 A1 | 6/2013 | Chau et al. |
| 2013/0165483 A1 | 6/2013 | Chau et al. |
| 2013/0217689 A1 | 8/2013 | Cardin et al. |
| 2013/0267563 A1 | 10/2013 | Hirose et al. |

FOREIGN PATENT DOCUMENTS

| | | |
|---|---|---|
| GB | 874634 A | 8/1961 |
| JP | 10087490 | 4/1998 |
| JP | 2007-197324 A | 8/2007 |
| WO | WO-97/12615 A1 | 4/1997 |
| WO | WO-98/08845 A1 | 3/1998 |
| WO | WO-98/47894 A1 | 10/1998 |
| WO | WO-00/02871 A1 | 1/2000 |
| WO | WO-00/35912 A1 | 6/2000 |
| WO | WO-00/63204 A2 | 10/2000 |
| WO | WO-02/088107 A1 | 11/2002 |
| WO | WO-03/015776 A1 | 2/2003 |
| WO | WO-03/027085 A2 | 4/2003 |
| WO | WO-03/027107 A1 | 4/2003 |
| WO | WO-03/040096 A2 | 5/2003 |
| WO | WO-2004/016592 A1 | 2/2004 |
| WO | WO-2004/016741 A2 | 2/2004 |
| WO | WO-2004/096797 A1 | 11/2004 |
| WO | WO-2006/046031 A1 | 5/2006 |
| WO | WO-2006/068933 A2 | 6/2006 |
| WO | WO-2006/078287 A2 | 7/2006 |
| WO | WO-2006/097030 A1 | 9/2006 |
| WO | WO-2006/102194 A1 | 9/2006 |
| WO | WO-2006/114313 A1 | 11/2006 |
| WO | WO-2007/002559 A1 | 1/2007 |
| WO | WO-2007/043400 A1 | 4/2007 |
| WO | WO-2007/087488 A2 | 8/2007 |
| WO | WO-2007/096315 A1 | 8/2007 |
| WO | WO-2007/110344 A1 | 10/2007 |
| WO | WO-2007/129044 A1 | 11/2007 |
| WO | WO-2007/129161 A2 | 11/2007 |
| WO | WO-2007/138110 A2 | 12/2007 |
| WO | WO-2008/014238 A2 | 1/2008 |
| WO | WO-2008/021235 A2 | 2/2008 |
| WO | WO-2008/023159 A1 | 2/2008 |
| WO | WO-2008/024980 A2 | 2/2008 |
| WO | WO-2008/036541 A1 | 3/2008 |
| WO | WO-2008/083070 A1 | 7/2008 |
| WO | WO-2008/090382 A1 | 7/2008 |
| WO | WO-2008/097835 A2 | 8/2008 |
| WO | WO-2008/098105 A1 | 8/2008 |
| WO | WO-2008/134679 A1 | 11/2008 |
| WO | WO-2008/139161 A1 | 11/2008 |
| WO | WO-2008/157273 A1 | 12/2008 |
| WO | WO-2009/040730 A2 | 4/2009 |
| WO | WO-2009/042607 A1 | 4/2009 |
| WO | WO-2009/049028 A1 | 4/2009 |
| WO | WO-2009/094224 A1 | 7/2009 |
| WO | WO-2009/106885 A1 | 9/2009 |
| WO | WO-2009/122148 A1 | 10/2009 |
| WO | WO-2009/154741 A1 | 12/2009 |
| WO | WO-2009/158374 A2 | 12/2009 |
| WO | WO-2010/001126 A1 | 1/2010 |
| WO | WO-2010/005841 A1 | 1/2010 |
| WO | WO-2010/017079 A1 | 2/2010 |
| WO | WO-2010/055304 A2 | 5/2010 |
| WO | WO-2010/071741 A1 | 6/2010 |
| WO | WO-2010/080873 A1 | 7/2010 |
| WO | WO-2010/090716 A1 | 8/2010 |
| WO | WO-2010/132598 A1 | 11/2010 |
| WO | WO-2011/043371 A1 | 4/2011 |

OTHER PUBLICATIONS

Sheridan (J. Chem. Inf. Comput. Sci. 2002, 42, 103-108).*
4-Oxazolecarboxylic acid, 5-[(ethoxymethylene)amino]-2-(4-pyridinyl)-, ethyl ester- (CA Index Name), CAS Registry No. 885901-22-4, entered May 29, 2006.
Adib, M. et al., Facile One-Pot Three-Component Synthesis of Functionalized Pyridylfuran-2-amines, Helvetica Chimica Acta, 89(2):299-303 (2006).
Boppana, K. et al., Knowledge based identification of MAO-B selective inhibitors using pharmacophore and structure based virtual screening models, European Journal of Medicinal Chemistry, 44:3584-3590 (2009).
Chattopadhyay, S. K. et al., Efficient Construction of the Carbon Skeleton of the Novel Polyoxazole-Based Cyclopeptide IB-01211 via a Biomimetic Macrocyclisation, Synlett, 4:555-558 (2010).
Database Chemcats, Chemical Abstracts Service, Columbus, Ohio, US, XP002545555, order No. T5337328.
Fletcher, A. N. et al., Laser Dye Stability, Part 12. The Pyridinium Salts, Applied Physics, B43:155-160 (1987).
Hernandez, D. et al., Synthesis and Antitumor Activity of Mechercharmycin A Analogues, Journal of Medicinal Chemistry, 51: 5722-5730 (2008).
Hernandez, D. et al., Synthesis of Natural Product Derivatives Containing 2,4-Concatenated Oxazoles, European Journal of Organic Chemistry, (19): 3389-3396 (2008).
International Search Report for PCT/US09/00513, 3 pages (Jun. 10, 2009).
International Search Report for PCT/US09/03607, 4 pages (Sep. 23, 2009).
International Search Report for PCT/US10/00234, 3 pages (Jun. 1, 2010).
International Search Report for PCT/US11/47245, 2 pages (Dec. 22, 2011).
International Search Report for PCT/US11/47407, 2 pages (Dec. 22, 2011).
International Search Report for PCT/US11/56135, 4 pages (May 31, 2012).
Liang, J. et al., Crystal Structure of P13K SH3 Domain at 2.0 A Resolution, Journal of Molecular Biology, 257:632-643 (1996).
Menear, K. A. et al., Identification and optimisation of novel and selective small molecular weight kinase inhibitors of mTOR, Bioorganic & Medicinal Chemistry Letters, 19:5898-5901 (2009).
Revesz, L. et al., SAR of 2,6-Diamino-3,5-difluoropyridinyl Substituted Heterocycles as Novel p38 MAP Kinase Inhibitors, Bioorganic & Medicinal Chemistry Letters, 12(16):2109-2112 (2002).
Thompson, M. J. et al., Development of a Diversity-Oriented Approach to Oxazole-5-amide Libraries, Journal of Organic Chemistry, 74(10):3856-3865 (2009).
Wang, Q. et al., Copper-Mediated Amidation of Heterocyclic and Aromatic C-H Bonds, Organic Letters, 11( 22): 5178-5180 (2009).
Written Opinion for PCT/US09/00513, 5 pages (Jun. 10, 2009).
Written Opinion for PCT/US09/03607, 5 pages (Sep. 23, 2009).
Written Opinion for PCT/US10/00234, 6 pages (Jun. 1, 2010).
Written Opinion for PCT/US11/47245, 5 pages (Dec. 22, 2011).
Written Opinion for PCT/US11/47407, 7 pages (Jun. 10, 2009).
Written Opinion for PCT/US11/56135, 13 pages (May 31, 2012).

(56) References Cited

OTHER PUBLICATIONS

Zhang, F. et al., Decarboxylative C-H Cross-Coupling of Azoles, Angew. Chem. Int. Ed., 49(15): 2768-2771 (2010).
2-Thiophenecarboxylic acid, 3-(4-chlorophenyl)-4-cyano-5-(4-morpholinyl)-(CA Index Name), CAS Registry No. 883097-33-4, entered May 5, 2006.
2-Thiophenecarboxylic acid, 3-(4-chlorophenyl)-4-cyano-5-(4-morpholinyl)-, methyl ester (CA Index Name), CAS Registry No. 882283-38-7, entered Apr. 30, 2006.
Abdelrazek et al., Heterocyclic Synthesis with Nitriles: Synthesis of Some Novel Thiophene and Thieno[2,3-d]Pyrimidine Derivatives, Phosphorus, Sulfur, Silicons, 71:93-97 (1992).
Al-Azawe et al., Synthesis of 2, 5-Disubstituted Thiazoles and Their Reactions with Grignard Reagents, Journal of the Iraqi Chemical Society, 13(1): 1-13 (1988).
Batista et al., Synthesis and characterization of new thienylpyrrolyl-benzothiazoles as efficient and thermally stable nonlinear optical chromophores, Tetrahedron, 63(20):4258-4265 (2007).
Batista et al., Synthesis and Second-Order Nonlinear Optical Properties of New Chromophores Containing Benzimidazole, Thiophene, and Pyrrole Heterocycles, Tetrahedron, 63(39): 9842-9849 (2007).
Berndt, A. et al., The p110σ crystal structure uncovers mechanisms for selectivity and potency of novel P13K inhibitors, Nature Chemical Biology, 6(2):117-124 (2010).
Carbamic acid,4,4'-diphenyl[2,2'-bithiazole]-5,5'-diyl)bis-, dimethyl ester (9CI)(CA Index Name), CAS Registry No. 505060-78-6, entered Apr. 25, 2003.
Choi, W. et al., Synthesis and Antiproliferative Activities of 1-Substituted-3-(3-chloro-5-methoxy phenyl)-4-pyridinylpyrazole Derivatives Against Melanoma Cell Line, Bulletin of the Korean Chemical Society, 30(9):2027-2031 (2009).
Cudworth et al., Structure-Activity Relationship Development of Dihaloaryl Triazole Compounds as Insecticides and Acaricides. 1. Phenyl Thiophen-2-yl Triazoles, Journal of Agricultural and Food Chemistry, 55(18): 7517-7526 (2007).
Benzamide, N-[2-(5-amino-1-phenyl-1H-pyrazol-4-yl)-4-phenyl-5-thiazolyl]-4-methyl- (CA Index Name), CAS Registry No. 1017527-68-2, entered Apr. 27, 2008.
5-Thiazolecarboxamide, N-[2'-(aminosulfonyl)[1,1-biphenyl]-2-yl]-4-(4-methoxyphenyl)-2-(1Hpyrrol-1-yl)- (CA Index Name), CAS Registry No. 1027033-64-2, entered Jun. 10, 2008.
1,2,4-Oxadiazole-3-ethanamine, 5-[5-(1H-imidazol-2-yl)-2-thienyl]-N,N-dimethyl-(CA Index Name), CAS Registry No. 1066888-52-5, entered Oct. 27, 2008.
1,2,4-Oxadiazole, 5-[5-(1H-imidazol-2-yl)-2-thienyl]-3-(methoxymethyl)-(CA Index Name), CAS Registry No. 1069660-66-7, entered Nov. 2, 2008.
2,7-Naphthyridine, 1,2,3,4-tetrahydro-5-[5-[5-(1H-imidazol-2-yl)-2-thienyl]-1,2,4-oxadiazol-3-yl]- 6-methyl-(CA Index Name), CAS Registry No. 1069717-72-1, entered Nov. 2, 2008.
Pyrazolo[1,5-a]pyrimidin-7(4H)-one,3-ethyl-5-[5-(1H-imidazol-2-yl)-2-thienyl]-(CA Index Name), CAS Registry No. 1087437-07-7, entered Dec. 21, 2008.
3H-1,2,4-Triazole-3-thione, 2,4-dihydro-4-methyl-544-methyl-2-(5-methyl-3-isoxazolyl)-5-thiazolyl]-(CA Index Name), CAS Registry No. 264616-86-6, entered May 12, 2000.
Acetamide, N-(3,5-dichlorophenyl)-2-[[4-methyl-5-[methyl-2-(5-methyl-3-isoxazolyl)-5-thiazolyl]-4H-1,2,4-triazol-3-yl]thio]-(CA Index Name), CAS Registry No. 264626-19-9, entered May 12, 2000.
Acetamide, N-(4-chlorophenyl)-2-[[4-methyl-5-[4-methyl-2-(5-methyl-3-isoxazolyl)-5-thiazolyl]-4H-1,2,4-triazol-3-yl]thio]-(CA Index Name), CAS Registry No. 264626-21-3, entered May 12, 2000.
Benzamide, N,N'-(4,4'-di-2-thienyl[2,2'-bithiazole]-5,5'-diyl)bis-(CA Index Name) CAS Registry No. 691381-57-4, entered Jun. 10, 2004.
Carbamic acid, N,N'-(4,4'-di-2-thienyl[2,2'-bithiazole]-5,5'-diyl)bis-,C,C'-dimethyl ester (CA Index Name) CAS Registry No. 691381-58-5, entered Jun. 10, 2004.
Benzamide, N,N'-[4,4'-bis(4-fluorophenyl)[2,2'-bithiazole]-5,5'-diyl]bis[4-methyl-(CA Index Name) CAS Registry No. 691381-60-9, entered Jun. 10, 2004.
4-Thiazolecarboxamide, 2-(4-acetyl-5-methyl-1H-1,2,3-triazol-1-yl)-N,N-diethyl-5-phenyl-(CA Index Name), CAS Registry No. 709639-21-4, entered Jul. 14, 2004.
Imidazo[1,2-a]pyridine, 6-[3-[5-(2H-tetrazol-5-yl)-2-thienyl]-1H-pyrazol-4-yl]-3-(2-thiazolyl)-(CA Index Name) CAS Registry No. 732241-18-8, entered Aug. 25, 2004).
Benzamide, N-(4'-amino-2',3'-dihydro-3',4-diphenyl-2'-thioxo[2,5'-bithiazol]-5-yl)-(CA Index Name)CAS Registry No. 879910-33-5, entered Apr. 10, 2006.
Database CAS Registry (Columbus, Ohio), RN 893689-50-4 (Entered Jul. 17, 2006).
Database CAS Registry (Columbus, Ohio), RN 893692-42-7 (Entered Jul. 17, 2006).
Database CAS Registry (Columbus, Ohio), RN 893704-20-6 (Entered Jul. 17, 2006).
Database CAS Registry (Columbus, Ohio), RN 893705-40-3 (Entered Jul. 17, 2006).
Database CAS Registry (Columbus, Ohio), RN 898517-78-7 (Entered Aug. 3, 2006).
2-Thiazolamine, 4-[5-(2H-tetrazol-5-yl)-2-thienyl]-(CA Index Name), CAS Registry No. 937625-84-8, entered Jun. 17, 2007.
1H-Pyrazole-1-carboxylic acid, 5-[2,2'-bithiophen]-5-yl-, ethyl ester (CA Index Name), CAS Registry No. 957595-63-0, entered Dec. 12, 2007.
Datta et al., A Novel Route to Methyl 3-3(3,4-Disubstituted 5-alkylthio/amino-2-thienyl) propenoates, Synthesis, 7:556-567 (1988).
Emmitte et al., Discovery of Thiophene Inhibitors of Polo-like Kinase, Bioorganic & Medicinal Chemistry Letters, 19(3): 1018-1021 (2009).
Fridman et al., Spectroscopy, Photophysical and Photochemical Properties of Bisimidazole, Derivatives, Journal of Photochemistry and Photobiology, A: Chemistry, 188(1): 25-33 (2007).
Green et al., Parallel Synthesis of 2-aryl-4-aminobenzimidazoles and their Evaluation as Gonadotropin Releasing Hormone Antagonists, Journal of Combinatorial Chemistry, 11(1): 117-125 (2009).
Heyde et al., A Simple Route to N,N-Dialkyl Derivatives of 2-Amino-5-thiophenecarboxylates, Eur. J. Org. Chem.: 3273-3278 (2000).
Hirai et al., Heterocyclic Cation Systems. 14. Sythesis of Thieno[3,2-e][1,4]diazepine, Thiazolo[4,5-e][1,4]diazepine, and s-Triazolo[3,4-c]thiazolo[4,5-e][1,4]diazepine Derivatives, Journal of Organic Chemistry, 45:253-260 (1980).
Hirai et al., Novel Synthesis of Thiophene Derivatives from 1,3-Oxathil-2-ylideneimmonium Salt, Chemical & Pharmaceutical Bulletin, 19(10): 2194-2197 (1971).
Lethu et al., Discovery of a New Class of Protein Farnesyltransferase Inhibitors in the Arylthiophene Series, J. Med. Chem., 52: 6205-6208 (2009).
Liu et al., Highly Selective and Potent Thiophenes as PI3K Inhibitors with Oral Antitumor Activity, Med. Chem. Lett., 2:809-813 (2011).
Lucchesini, A Simple Way to Sequentially Connected Polycycles Containing Terminal Pyrrole Rings: Synthesis of Possible Precursors of Materials for Nonlinear Optics, Tetrahedron, 48(45): 9951-9966 (1992).
Mamedov et al., Synthesis and Some Properties of the Methyl Ester and N,N-diethylamide of 2-Azido-5-Phyenyl-4-Thiazolecarboxylic Acid, Chemistry of Heterocyclic Compounds, 29(5): 607-611 (1993).
Matschke et al., Quinomethides Versus Unsymmetric Hybrids: Two Variations of Non-Radicaloid SEM-States in Four-Electron Redox Systems of bis-4H-imidazoles, Structural Chemistry, 19(3):399-405 (2008).
Moorthy et al., In Silico-Based Structural Analysis of Arylthiophene Derivatives for Ftase Inhibitory Activity, hERG, and Other Toxic Effects, Journal of Biomolecular Screening, 16(9):1037-1046 (2011).
Morpholine, 4-(5-(4,5-diphenyl-1H-imidazol-2-yl)-2-thienyl]-, Ryan Scientific Screening Library, Publication date: Jan. 25, 2008, CAS Registry No. 851954-74-0.

(56) References Cited

OTHER PUBLICATIONS

Nagasaki et al., CASREACT 139:52925 (2003).
Nagasaki et al., Useful Synthesis of Various Thiazole and Polythiazolyl Derivatives from Thiocarboxamide and -Bromacyl Compound, Heterocycles, 60(2): 321-335 (2003).
Pinto et al., The Synthesis of 5-alkoxy and 5-amino Substituted Thiophenes, Tetrahedron Letters, 41(10): 1597-1600 (2000).
Raap, Some Synthesis with Dimethyl Monothionemalonate, Canadian Journal of Chemistry, 46:13, 2255-2261 (1968).
Rehwald et al., New Synthesis of 2,4-Diaminothiophenes- Use of (1,3-oxathioI-2- ylidene)Malononitrile, Heterocycles, 45(3): 493-500 (1997).
Welker et al., Recent Syntheses of PI3K/Akt/mTOR signaling pathway inhibitors, Bioorganic & Medicinal Chemistry, 21(14): 4063-4091 (2013).
Zhou et al., Selenium-Containing Heterocycles from Isoselenocyanates: Synthesis of 1,3-Selenazoles from N-Phenylimidoyl Isoselenocyanates, Helvetica Chimica Acta, 83: 1576-1598 (2000).

* cited by examiner

HETEROARYLS AND USES THEREOF

The present application claims the benefit of U.S. Provisional Application Ser. No. 61/372,553, filed Aug. 11, 2010, U.S. Provisional Application Ser. No. 61/372,628, filed Aug. 11, 2010, and U.S. Provisional Application Ser. No. 61/469,157, filed Mar. 30, 2011 which are hereby incorporated by reference in their entirety.

BACKGROUND OF THE INVENTION

Phosphatidylinositol 3-kinase (PI3K) is a family of lipid kinases that phosphorylate phosphatidylinositol at the 3' position of the inositol ring. PI3K is comprised of several classes of genes, including Class IA, IB, II and III and some of these classes contain several isoforms (reviewed in Engelman et al., Nature Review Genetics 7:606-619 (2006)). Adding to the complexity of this family is the fact that PI3Ks function as heterodimers, comprising a catalytic domain and a regulatory domain. The PI3K family is structurally related to a larger group of lipid and serine/threonine protein kinases known as the phosphatidylinositol 3-kinase like kinases (PIKKs), which also includes DNA-PK, ATM, ATR, mTOR, TRRAP and SMG1.

PI3K is activated downstream of various mitogenic signals mediated through receptor tyrosine kinases, and subsequently stimulates a variety of biological outcomes; including increased cell survival, cell cycle progression, cell growth, cell metabolism, cell migration and angiogenesis (reviewed in Cantley, Science 296:1655-57 (2002); Hennessy et al., Nature Reviews Drug Discovery 4:988-1004 (2005); Engelman et al., Nature Review Genetics 7:606-619 (2006)). Thus, PI3K hyper-activation is associated with a number of hyper-proliferative, inflammatory, or cardiovascular disorders; including cancer, inflammation, and cardiovascular disease.

There are a number of genetic aberrations that lead to constitutive PI3K signaling; including activating mutations in PI3K itself (Hennessy et al., Nature Reviews Drug Discovery 4:988-1004 (2005); reviewed in Bader et al., Nature Reviews Cancer 5:921-9 (2005)); RAS (reviewed in Downward Nature Reviews Cancer 3:11-22 (2003)) and upstream receptor tyrosine kinases (reviewed in Zwick et al., Trends in Molecular Medicine 8:17-23 (2002)) as well as inactivating mutations in the tumor suppressor PTEN (reviewed in Cully et al., Nature Reviews Cancer 6:184-92 (2006)). Mutations in each of these gene classes have proven to be oncogenic and are commonly found in a variety of cancers.

The molecules defined within this invention inhibit the activity of PI3K, and therefore may be useful for the treatment of proliferative, inflammatory, or cardiovascular disorders. Cases where PI3K pathway mutations have been linked to proliferative disorders where the molecules defined within this invention may have a therapeutic benefit include benign and malignant tumors and cancers from diverse lineage, including but not limited to those derived from colon (Samuels et al., Science 304:554 (2004); reviewed in Karakas et al., British Journal of Cancer 94: 455-59 (2006)), liver (reviewed in Karakas et al., British Journal of Cancer 94: 455-59 (2006)), intestine (reviewed in Hennessy et al., Nature Reviews Drug Discovery 4:988-1004 (2005)), stomach (Samuels et al., Science 304:554 (2004); reviewed in Karakas et al., British Journal of Cancer 94: 455-59 (2006)), esophagus (Phillips et al., International Journal of Cancer 118:2644-6 (2006)); pancreas (reviewed in Downward Nature Reviews Cancer 3:11-22 (2003)); skin (reviewed in Hennessy et al., Nature Reviews Drug Discovery 4:988-1004 (2005)), prostate (reviewed in Hennessy et al., Nature Reviews Drug Discovery 4:988-1004 (2005)), lung (Samuels et al., Science 304:554 (2004); reviewed in Karakas et al., British Journal of Cancer 94: 455-59 (2006)), breast (Samuels et al., Science 304:554 (2004); Isakoff et al., Can Res 65:10992-1000 (2005); reviewed in Karakas et al., British Journal of Cancer 94: 455-59 (2006)), endometrium (Oda et al., Can Res 65:10669-73 (2005); reviewed in Hennessy et al., Nature Reviews Drug Discovery 4:988-1004 (2005)), cervix (reviewed in Hennessy et al., Nature Reviews Drug Discovery 4:988-1004 (2005)); ovary (Shayesteh et al., Nature Genetics 21:99-102 (1999); reviewed in Karakas et al., British Journal of Cancer 94: 455-59 (2006)), testes (Moul et al., Genes Chromosomes Cancer 5:109-18 (1992); Di Vizio et al., Oncogene 24:1882-94 (2005)), hematological cells (reviewed in Karakas et al., British Journal of Cancer 94: 455-59 (2006); Hennessy et al., Nature Reviews Drug Discovery 4:988-1004 (2005)), pancreas (reviewed in Downward Nature Reviews Cancer 3:11-22 (2003)), thyroid (reviewed in Downward Nature Reviews Cancer 3:11-22 (2003); reviewed in Hennessy et al., Nature Reviews Drug Discovery 4:988-1004 (2005)); brain (Samuels et al., Science 304:554 (2004); reviewed in Karakas et al., British Journal of Cancer 94: 455-59 (2006)), bladder (Lopez-Knowles et al., Cancer Research 66:7401-7404 (2006); Hennessy et al., Nature Reviews Drug Discovery 4:988-1004 (2005)); kidney (reviewed in Downward Nature Reviews Cancer 3:11-22 (2003)) and Head and Neck (reviewed in Engelman et al., Nature Reviews Genetics 7:606-619 (2006)).

Other classes of disorders with aberrant PI3K pathway signaling where the molecules defined within this invention may have a therapeutic benefit include inflammatory and cardiovascular diseases, including but not limited to allergies/anaphylaxis (reviewed in Rommel et al., Nature Reviews Immunology 7:191-201 (2007)), acute and chronic inflammation (reviewed in Ruckle et al., Nature Reviews Drug Discovery 5:903-12 (2006); reviewed in Rommel et al., Nature Reviews Immunology 7:191-201 (2007)), rheumatoid arthritis (reviewed in Rommel et al., Nature Reviews Immunology 7:191-201 (2007)); autoimmunity disorders (reviewed in Ruckle et al., Nature Reviews Drug Discovery 5:903-12 (2006)), thrombosis (Jackson et al., Nature Medicine 11:507-14 (2005); reviewed in Ruckle et al., Nature Reviews Drug Discovery 5:903-12 (2006)), hypertension (reviewed in Ruckle et al., Nature Reviews Drug Discovery 5:903-12 (2006)), cardiac hypertrophy (reviewed in Proud et al., Cardiovascular Research 63:403-13 (2004)), and heart failure (reviewed in Mocanu et al., British Journal of Pharmacology 150:833-8 (2007)).

Vacuolar Protein Sorting 34 (VPS34) is the sole Class III PI3K family member. VPS34 functions in the formation and trafficking of multiple intracellular vesicles, including vacuoles, endosomes, multivesicular bodies, lysosomes and autophagosomes (reviewed in Backer Biochem J 2008; Yan and Backer Biochem J 2007). VPS34 carries out these activities by phosphorylating PtdIns forming PtdIns3P, resulting in the recruitment and localization of a variety of FYVE and PX domain containing effector proteins that facilitate vesicular formation, elongation and movement. At a cellular level, inhibition of VPS34 results in defects in protein sorting and autophagy. Broadly defined, autophagy is a regulated process whereby cells catabolize subcellular components targeted for degradation by enclosing them in double-membrane vesicles which then fuse with lysosomes. Autophagy has been best characterized as occurring during times of nutrient deprivation, but also plays a role in normal cellular and tissue homeostasis and functions, including the development of multiple tissue types, the immune response, clearance of neuronal aggregates and tumor suppression. In addition to functioning in vesicle formation and movement, VPS34 may also participate in several signal transduction pathways (reviewed in Backer Biochem J 2008). Given that VPS34 plays an important role in many critical cellular processes including autophagy, inhibitors of VPS34 may have therapeutic application in a number of diseases, including but not limited to cancer, muscular disorders, neurodegeneration, inflammatory disease, infectious disease and other age related illnesses (reviewed in Shintani and Klionshy Science 2004; Kondo et al Nat Rev Cancer 2005; Delgato et al Immunol Rev 2009).

Clearly, it would be beneficial to provide novel VPS34 and/or PI3K inhibitors that possess good therapeutic properties, especially for the treatment of proliferative, inflammatory, or cardiovascular disorders.

1. General Description of Compounds of the Invention

This invention provides compounds that are inhibitors of VPS34 and/or PI3K, and accordingly are useful for the treatment of proliferative, inflammatory, or cardiovascular disorders. The compounds of this invention are represented by a compound of formula IA or IB:

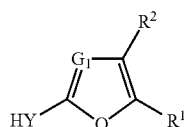

IA

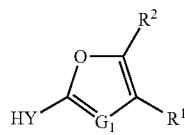

IB or a pharmaceutically acceptable salt thereof, wherein:
$G_1$ is N or $CR^3$, wherein $R^3$ is H, —CN, halogen, —Z—$R^5$, $C_{1-6}$ aliphatic, or 3-10-membered cycloaliphatic, wherein:
  Z is selected from an optionally substituted $C_{1-3}$ alkylene chain, —O—, —N($R^{3a}$)—, —S—, —S(O)—, —S(O)$_2$—, —C(O)—, —CO$_2$—, —C(O)N$R^{3a}$—, —N($R^{3a}$)C(O)—, —N($R^{3a}$)CO$_2$—, —S(O)$_2$N$R^{3a}$—, —N($R^{3a}$)S(O)$_2$—, —OC(O)N($R^{3a}$)—, —N($R^{3a}$)C(O)N$R^{3a}$—, —N($R^{3a}$)S(O)$_2$N($R^{3a}$)—, or —OC(O)—;
  $R^{1a}$ is hydrogen or an optionally substituted $C_{1-4}$ aliphatic, and
  $R^5$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
$R^1$ is CY, CN, —CON($R^4$)$_2$, —COOR$^4$, —C(O)CH$_3$, —NHCOR$^4$, —NHSO$_2$R$^4$, —NHCON($R^4$)$_2$, —NHCOOR$^4$, —NHSO$_2$N($R^4$)$_2$, —CONHOH, —CH$_2$OH, —CH$_2$NH$_2$, —CH$_2$NHCOCH$_3$, —SO$_2$NH$_2$, —CONH=NHNH$_2$, or —NHSO$_2$OR$^4$, wherein CY is an optionally substituted group selected from a 3-7-membered cycloaliphatic or heterocyclic group or a 5-6-membered aryl, or heteroaryl group; wherein:
  $R^4$ is H, —$Z_2$—$R^6$, optionally substituted $C_{1-6}$ aliphatic, 6-10-membered aryl, or 5-10-membered heteroaryl having 1-5 heteroatoms independently selected from nitrogen, oxygen, or sulfur or optionally substituted 3-10-membered cycloaliphatic, wherein:
    $Z_2$ is selected from an optionally substituted $C_{1-3}$ alkylene chain, —S(O)—, —S(O)$_2$—, —C(O)—, —CO$_2$—, —C(O)NR$^{4a}$—, S(O)$_2$NR$^{4a}$—, or —(CH$_2$)$_q$O(CH$_2$)$_q$—;
    $R^{4a}$ is hydrogen or an optionally substituted $C_{1-4}$ aliphatic, and
    $R^6$ is an optionally substituted group selected from $C_{1-6}$ aliphatic, —OR$^{4a}$, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  q is 0 to 3;
$R^2$ is hydrogen, halogen, CN, —N($R^{21}$)$_2$, or an optionally substituted monocyclic group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, wherein $R^2$ is optionally substituted with 1-4 occurrences of $R^{2a}$, wherein each occurrence of $R^{2a}$ is independently —$R^{12a}$, -$T_2$-$R^{12d}$, -$T_2$-$R^{12a}$, or —$V_2$-$T_2$-$R^{12d}$, and:
  each occurrence of $R^{12a}$ is independently halogen, —CN, —NO$_2$, —$R^{12c}$, —N($R^{12b}$)$_2$, —OR$^{12b}$, —SR$^{12c}$, —S(O)$_2$R$^{12c}$, —C(O)R$^{12b}$, —C(O)OR$^{12b}$, —C(O)N($R^{12b}$)$_2$, —S(O)$_2$N($R^{12b}$)$_2$, —OC(O)N($R^{12b}$)$_2$, —N($R^{12e}$)C(O)R$^{12b}$, —N($R^{12e}$)SO$_2$R$^{12c}$, —N($R^{12e}$)C(O)OR$^{12b}$, —N($R^{12e}$)C(O)N($R^{12b}$)$_2$, or —N($R^{12e}$)SO$_2$N($R^{12b}$)$_2$;
  each occurrence of $R^{12b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  or two occurrences of $R^{12b}$, taken together with a nitrogen atom to which they are bound, form an optionally substituted 4-7-membered heterocyclyl ring having 0-1 additional heteroatoms selected from nitrogen, oxygen, or sulfur;
  each occurrence of $R^{12c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
  each occurrence of $R^{12d}$ is independently hydrogen or an optionally substituted group selected from 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{12e}$ is independently hydrogen or an optionally substituted $C_{1-6}$ aliphatic group;

each occurrence of $V_2$ is independently —N($R^{12e}$)—, —O—, —S—, —S(O)—, —S(O)$_2$—, —C(O)—, —C(O)O—, —C(O)N($R^{12e}$)—, —S(O)$_2$N($R^{12e}$)—, —OC(O)N($R^{12e}$)—, —N($R^{12e}$)C(O)—, —N($R^{12e}$)SO$_2$—, —N($R^{12e}$)C(O)O—, —N($R^{12e}$)C(O)N($R^{12e}$)—, —N($R^{12e}$)SO$_2$N($R^{12e}$)—, —OC(O)—, or —C(O)N($R^{12e}$)—O—; and $T_2$ is an optionally substituted $C_1$-$C_6$alkylene chain wherein the alkylene chain optionally is interrupted by —N($R^{13}$)—, —O—, —S—, —S(O)—, —S(O)$_2$—, —C(O)—, —C(O)O—, —C(O)N($R^{13}$)—, —S(O)$_2$N($R^{13}$)—, —OC(O)N($R^{13}$)—, —N($R^{13}$)C(O)—, —N($R^{13}$)SO$_2$—, —N($R^{13}$)C(O)O—, —N($R^{13}$)C(O)N($R^{13}$)—, —N($R^{13}$)S(O)$_2$N($R^{13}$)—, —OC(O)—, or —C(O)N($R^{13}$)—O— or wherein $T_3$ or a portion thereof optionally forms part of an optionally substituted 3-7 membered cycloaliphatic or heterocyclyl ring, wherein $R^{13}$ is hydrogen or an optionally substituted $C_{1-4}$aliphatic group;

each occurrence of $R^{21}$ is independently hydrogen, —S(O)$_2R^{2a}$, —C(O)$R^{2a}$, or an optionally substituted C1-6aliphatic, provided that only one occurrence of $R^{21}$ is hydrogen; or wherein two occurrences of R21, taken together with the atom to which they are bound, form an optionally substituted 5-6-membered heteroaryl ring having 0-3 additional heteroatoms independently selected from nitrogen, oxygen or sulfur; and HY is an optionally substituted group selected from:

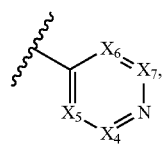

A

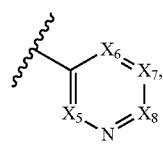

B

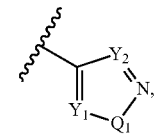

C

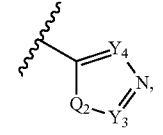

D

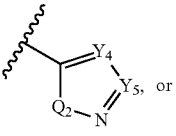

E

-continued

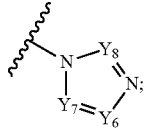

F wherein each occurrence of $X_4$, $X_5$, $X_6$, $X_7$, and $X_8$ is independently —$CR^{10}$ or N, provided no more than two occurrences of $X_4$, $X_5$, $X_6$, $X_7$, and $X_8$ are N;

each occurrence of $Q_1$ and $Q_2$ is independently S, O or —$NR^9$;

each occurrence of $Y_1$, $Y_2$, $Y_3$, $Y_4$, $Y_5$, $Y_6$, $Y_7$, and $Y_8$ is independently —$CR^{10}$ or N, provided no more than two occurrences of $Y_6$, $Y_7$, and $Y_8$ are N;

or wherein two adjacent occurrences of $X_4$ and $X_5$, $X_6$, and $X_7$, $X_7$ and $X_8$, $Y_1$ and $Q_1$, $Y_3$ and $Q_2$, $Y_4$ and $Y_5$ or $Y_6$ and $Y_7$ together with the atom to which they are bound, form an optionally substituted fused group selected from 5-6-membered aryl, or 5-6-membered heteroaryl having 1-5 heteroatoms independently selected from nitrogen, oxygen, or sulfur;

wherein $R^{10}$ is —$R^{10b}$, —$V_1$—$R^{10c}$, -$T_1$-$R^{10b}$, or —$V_1$-$T_1$-$R^{10b}$ wherein:

$V_1$ is —$NR^{11}$—, —$NR^{11}$—C(O)—, —$NR^{11}$—C(S)—, —$NR^{11}$—C($NR^{11}$)—, —$NR^{11}$C(O)O$R^{10a}$—, —$NR^{11}$C(O)$NR^{11}$—, —$NR^{11}$C(S)OR$^{10a}$—, —$NR^{11}$C(S)NR$^{11}$—, —$NR^{11}$C(S)SR$^{10a}$—, —$NR^{11}$C($NR^{11}$)OR$^{10a}$—, —$NR^{11}$C($NR^{11}$)$NR^{11}$—, —$NR^{11}$S(O)$_2$—, —$NR^{11}$S(O)$_2NR^{11}$—, —C(O)—, —$CO_2$—, —C(O)$NR^{11}$—, —C(O)$NR^{11}$O—, —$SO_2$—, or —$SO_2NR^{11}$—;

each occurrence of $R^{10a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

$T_1$ is an optionally substituted $C_1$-$C_6$ alkylene chain wherein the alkylene chain optionally is interrupted by —N($R^{11}$)—, —O—, —S—, —S(O)—, —S(O)$_2$—, —C(O)—, —C(O)O—, —C(O)N($R^{11}$)—, —S(O)$_2$N($R^{11}$)—, —OC(O)N($R^{11}$)—, —N($R^{11}$)C(O)—, —N($R^{11}$)SO$_2$—, —N($R^{11a}$)C(O)O—, —$NR^{10a}$C(O)N($R^{10a}$)—, —N($R^{10a}$)S(O)$_2$N($R^{10a}$)—, —OC(O)—, or —C(O)N($R^{11}$)—O— or wherein $T_1$ forms part of an optionally substituted 3-7 membered cycloaliphatic or heterocyclyl ring;

each occurrence of $R^{10b}$ is independently hydrogen, halogen, —CN, —$NO_2$, —N($R^{11}$)$_2$, —OR$^{10a}$, —SR$^{10a}$, —S(O)$_2R^{10a}$, —C(O)$R^{10a}$, —C(O)OR$^{10a}$, —C(O)N($R^{11}$)$_2$, —S(O)$_2$N($R^{11}$)$_2$, —OC(O)N($R^{11}$)$_2$, —N($R^{11}$)C(O)$R^{10a}$, —N($R^{11}$)SO$_2R^{10a}$, —N($R^{11}$)C(O)OR$^{10a}$, —N($R^{11}$)C(O)N($R^{11}$)$_2$, or —N($R^{11}$)SO$_2$N($R^{11}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^{10c}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur, or $R^{10a}$ and $R^{10c}$ taken together with a nitrogen atom to which they are bound form an optionally substituted 4-7-membered heterocyclyl ring having 0-1 additional heteroatoms independently selected from nitrogen, oxygen, or sulfur;

each occurrence of $R^{11}$ is independently hydrogen, —C(O)$R^{11a}$, —CO$_2R^{11a}$, —C(O)N($R^{11a}$)$_2$, —C(O)N($R^{11a}$)—OR$^{11a}$, —SO$_2R^{11a}$, —SO$_2$N($R^{11a}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{11a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

each occurrence of $R^9$ is independently hydrogen, —C(O)$R^{9a}$, —CO$_2R^{9a}$, —C(O)N($R^{9b}$)$_2$, —SO$_2R^{9a}$, —SO$_2$N($R^{9b}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{9a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;

wherein each occurrence of $R^{9b}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur; or two occurrences of $R^{9b}$ taken together with the nitrogen atom to which they are bound, form an optionally substituted group selected from 3-6-membered heterocyclyl having 1-5 heteroatoms independently selected from nitrogen, oxygen, or sulfur, or 5-10-membered heteroaryl having 1-5 heteroatoms independently selected from nitrogen, oxygen, or sulfur; provided that:

a. when $R^2$ is a ring, then $R^2$ is substituted with at least one $R^{2a}$;

b. when CY is a 3-7-membered cycloaliphatic or a 5-6-membered aryl group, then the cycloaliphatic or aryl group is substituted with at least one non-hydrogen substituent;

c. when $R^2$ is hydrogen, then HY is selected from:

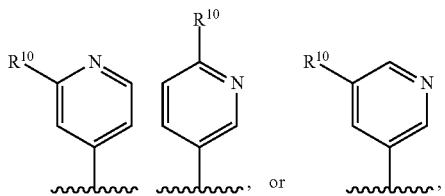

wherein $R^{10'}$ is —NHR$^{11}$;

d. when $G_1$ is N, $R^1$ is CONH$_2$, $R^2$ is phenyl substituted with a para-piperazin-1-yl group or a para-methoxy group, then HY is a group other than indolyl, 4-pyridinyl, 3-pyridinyl, indazolyl, pyrrolopyridinyl, or pyrazolyl;

e. when HY is unsubstituted 3-pyridinyl, then neither $R^1$ nor $R^2$ is CN or unsubstituted piperidinyl;

f. when HY is unsubstituted 4-pyridinyl and $R^2$ is —N($R^{21}$)$_2$, then $R^1$ and $R^3$ are not both optionally substituted —C(O)phenyl;

g. when HY is 4-pyridinyl, then HY is not tetra substituted h. the compound is other than:

4-Oxazolecarboxylic acid, 5-(2-methoxy-4-nitrophenyl)-2-(4-methyl-2-phenyl-5-thiazolyl)-, ethyl ester;

2-Pyrimidinamine, 4-[4-(4-fluorophenyl)-2-(4-pyridinyl)-5-oxazolyl]-N-[(1S)-1-phenylethyl]-;

Ethanone, 1-[5-(4-chlorophenyl)-2-(4-pyridinyl)-4-oxazolyl]-;

3H-Pyrazol-3-one, 5-[4,5-bis(4-methoxyphenyl)-2-oxazolyl]-1,2-dihydro-;

Pyridine, 4-[4-chloro-5-[4-(trichloromethyl)phenyl]-2-oxazolyl]-;

Pyrimidine, 5-[4-chloro-5-[4-(trichloromethyl)phenyl]-2-oxazolyl]-2,4,6trimethoxy-;

Pyridine, 3-[4-(4-fluorophenyl)-5-iodo-2-oxazolyl]-4-methyl-;

4-Oxazolecarboxylic acid, 5-[(ethoxymethylene)amino]-2-(4-pyridinyl)-, ethyl ester; 2-Pyridinecarboxylic acid, 5-[5-bromo-2-(5-chloro-3-pyridinyl)-4-oxazolyl]-, methyl ester;

2-Pyridinecarboxylic acid, 5-[5-bromo-2-(1-ethyl-1H-pyrazol-4-yl)-4-oxazolyl]-, methyl ester;

4-Oxazolecarboxamide, 2-[2-(acetylamino)-4-pyridinyl]-N-[3-(aminocarbonyl)-1-methyl-1H-pyrazol-4-yl]-;

4-Oxazolecarboxamide, 2-[2-(acetylamino)-4-pyridinyl]-N-[3-(aminocarbonyl)-1-ethyl-1H-pyrazol-4-yl]-;

Pyridine, 3-[4-bromo-5-(3,4-dichlorophenyl)-2-oxazolyl]-;

Benzenepropanamide, α-[[4-[5-(3,4-dichlorophenyl)-2-(3-pyridinyl)-4-oxazolyl]benzoyl]amino]-, (αS)—;

Benzoic acid, 4-[5-(3,4-dichlorophenyl)-2-(3-pyridinyl)-4-oxazolyl]-, methyl ester;

Benzoic acid, 4-[5-(3,4-dichlorophenyl)-2-(3-pyridinyl)-4-oxazolyl]-;

Pyridine, 3-[4-(4-chlorophenyl)-5-(4-methylphenyl)-2-oxazolyl]-4-methyl-;

Pyridinium, 4-[4,5-bis(4-methoxyphenyl)-2-oxazolyl]-1-methyl-, perchlorate; or

Benzenamine, 4-[5-(4-chlorophenyl)-2-(4-pyridinyl)-4-oxazolyl]-N,N-dimethyl-.

DETAILED DESCRIPTION OF THE INVENTION

2. Compounds and Definitions

Compounds of this invention include those described generally for formula IA or IB above, and are further illustrated by the classes, subclasses, and species disclosed herein. It will be appreciated that preferred subsets described for each variable herein can be used for any of the structural subsets as well. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40°, in the absence of moisture or other chemically reactive conditions, for at least a week, or a compound which maintains its integrity long enough to be useful for therapeutic or prophylactic administration to a patient.

The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound.

As used herein, "a 3-7-membered saturated, partially unsaturated, or aromatic monocyclic ring having 0-3 heteroatoms independently selected from nitrogen, oxygen, or sulfur, or an 8-10-membered partially unsaturated, or aromatic bicyclic ring system having 0-5 heteroatoms independently selected from nitrogen, oxygen, or sulfur" includes cycloaliphatic, heterocyclic, aryl and heteroaryl rings.

As used herein, the term "aromatic" includes aryl and heteroaryl groups as described generally below and herein.

The term "aliphatic" or "aliphatic group", as used herein, means an optionally substituted straight-chain or branched $C_{1-12}$ hydrocarbon, or a cyclic $C_{1-12}$ hydrocarbon which is completely saturated or which contains one or more units of unsaturation, but which is not aromatic (also referred to herein as "carbocycle", "cycloaliphatic", "cycloalkyl", or "cycloalkenyl"). For example, suitable aliphatic groups include optionally substituted linear, branched or cyclic alkyl, alkenyl, alkynyl groups and hybrids thereof, such as (cycloalkyl)alkyl, (cycloalkenyl)alkyl, or (cycloalkyl)alkenyl. Unless otherwise specified, in various embodiments, aliphatic groups have 1-12, 1-10, 1-8, 1-6, 1-4, 1-3, or 1-2 carbon atoms.

The term "alkyl", used alone or as part of a larger moiety, refers to an optionally substituted straight or branched chain hydrocarbon group having 1-12, 1-10, 1-8, 1-6, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-8 or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentyl, cyclohexenyl, and cycloheptenyl.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1,2-trifluoroethyl, 1,2,2-trifluoroethyl, and pentafluoroethyl.

The term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The terms "aryl" and "ar-", used alone or as part of a larger moiety, e.g., "aralkyl", "aralkoxy", or "aryloxyalkyl", refer to an optionally substituted $C_{6-14}$ aromatic hydrocarbon moiety comprising one to three aromatic rings. Preferably, the aryl group is a $C_{6-10}$ aryl group. Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. Preferably, the aralkyl group is $C_{6-10}$ aryl$C_{1-6}$alkyl, including, without limitation, benzyl, phenethyl, and naphthylmethyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9, or 10 ring atoms; having 6, 10, or 14π electrons shared in a cyclic array; and having, in addition to carbon atoms, from one to five heteroatoms. A heteroaryl group may be mono-, bi-, tri-, or polycyclic, preferably mono-, bi-, or tricyclic, more preferably mono- or bicyclic. The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR$^+$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3-7-membered ring. The substituents can be on the same or different atoms.

An alkylene chain also can be optionally interrupted by a functional group. An alkylene chain is "interrupted" by a functional group when an internal methylene unit is interrupted by the functional group. Examples of suitable "interrupting functional groups" are described in the specification and claims herein.

For purposes of clarity, all bivalent groups described herein, including, e.g., the alkylene chain linkers described above, are intended to be read from left to right, with a corresponding left-to-right reading of the formula or structure in which the variable appears.

An aryl (including aralkyl, aralkoxy, aryloxyalkyl and the like) or heteroaryl (including heteroaralkyl and heteroaralkoxy and the like) group may contain one or more substituents and thus may be "optionally substituted". In addition to the substituents defined above and herein, suitable substituents on the unsaturated carbon atom of an aryl or heteroaryl group also include and are generally selected from -halo, —$NO_2$, —CN, —$R^+$, —$C(R^+)=C(R^+)_2$, —$C\equiv CR^+$, —$OR^+$, —$SR^\circ$, —$S(O)R^\circ$, —$SO_2R^\circ$, —$SO_3R^+$, —$SO_2N(R^+)_2$, —$N(R^+)_2$, —$NR^+C(O)R^+$, —$NR^+C(S)R^+$, —$NR^+C(O)N(R^+)_2$, —$NR^+C(S)N(R^+)_2$, —$N(R^+)C(=NR^+)$—$N(R^+)_2$, —$N(R^+)C(=NR^+)$—$R^\circ$, —$NR^+CO_2R^+$, —$NR^+SO_2R^\circ$, —$NR^+SO_2N(R^+)_2$, —O—$C(O)R^+$, —O—$CO_2R^+$, —$OC(O)N(R^+)_2$, —$C(O)R^+$, —$C(S)R^\circ$, —$CO_2R^+$, —$C(O)$—$C(O)R^+$, —$C(O)N(R^+)_2$, —$C(S)N(R^+)_2$, —$C(O)N(R^+)$—$OR^+$, —$C(O)N(R^+)C(=NR^+)$—$N(R^+)_2$, —$N(R^+)C(=NR^+)$—$N(R^+)$—$C(O)R^+$, —$C(=NR^+)$—$N(R^+)_2$, —$C(=NR^+)$—$OR^+$, —$N(R^+)$—$N(R^+)_2$, —$C(=NR^+)$—$N(R^+)$—$OR^+$, —$C(R^O)=N$—$OR^+$, —$P(O)(R^+)_2$, —$P(O)(OR^+)_2$, —O—$P(O)$—$OR^+$, and —$P(O)(NR)$—$N(R)_2$, wherein $R^+$, independently, is hydrogen or an optionally substituted aliphatic, aryl, heteroaryl, cycloaliphatic, or heterocyclyl group, or two independent occurrences of $R^+$ are taken together with their intervening atom(s) to form an optionally substituted 5-7-membered aryl, heteroaryl, cycloaliphatic, or heterocyclyl ring. Each $R^\circ$ is an optionally substituted aliphatic, aryl, heteroaryl, cycloaliphatic, or heterocyclyl group.

An aliphatic or heteroaliphatic group, or a non-aromatic carbocyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: =O, =S, =C(R*)$_2$, =N—N(R*)$_2$, =N—OR*, =N—NHC(O)R*, =N—NHCO$_2$R°=N—NHSO$_2$R° or =N—R* where R° is defined above, and each R* is independently selected from hydrogen or an optionally substituted C$_{1-6}$ aliphatic group.

In addition to the substituents defined above and herein, optional substituents on the nitrogen of a non-aromatic heterocyclic ring also include and are generally selected from —R$^+$, —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R$^+$)$_2$, —C(S)N(R$^+$)$_2$, —C(=NH)—N(R$^+$)$_2$, or —N(R$^+$)S(O)$_2$R$^+$; wherein each R$^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of R$^+$ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of R$^+$ (or any other variable similarly defined in the specification and claims herein), are taken together with their intervening atom(s) include, but are not limited to the following: a) two independent occurrences of R$^+$ (or any other variable similarly defined in the specification or claims herein) that are bound to the same atom and are taken together with that atom to form a ring, for example, N(R$^+$)$_2$, where both occurrences of R$^+$ are taken together with the nitrogen atom to form a piperidin-1-yl, piperazin-1-yl, or morpholin-4-yl group; and b) two independent occurrences of R$^+$ (or any other variable similarly defined in the specification or claims herein) that are bound to different atoms and are taken together with both of those atoms to form a ring,
for example where a phenyl group is substituted with two occurrences of OR$^+$

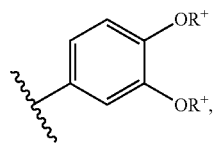

these two occurrences of R$^+$ are taken together with the oxygen atoms to which they are bound to form a fused 6-membered oxygen containing ring:

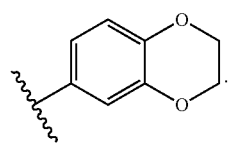 [SMILES: *c1ccc2c(c1)OCCO2]

It will be appreciated that a variety of other rings (e.g., spiro and bridged rings) can be formed when two independent occurrences of R$^+$ (or any other variable similarly defined in the specification and claims herein) are taken together with their intervening atom(s) and that the examples detailed above are not intended to be limiting.

Exemplary rings that are formed when two independent occurrences of X$_4$ and X$_5$, or X$_6$ and X$_7$; are taken together with their intervening atom(s) include, but are not limited to the following: pyrazolopyrimidinyl, purinyl, quinolyl, tetrahydroquinolinyl, quinazolinyl, naphthyridinyl, pyridopyrimidinyl, pyrazolopyridinyl, pyrrolopyridinyl, pyrrolopyrimidinyl, imidazopyridinyl, 1H-pyrrolo[2,3-b]pyridinyl-2(3H)-one, 3,4-dihydro-1,8-naphthyridinyl-2(1H)-one, 1,8-naphthyridinyl-2(1H)-one, 1H-pyridyl[2,3-d][1,3]oxazin-2(4H)-one, 1H-imidazo[4,5-b]pyridyl-2(3H)-one, oxazolo[4,5-b]pyridyl-2(3H)-one, 1,2-dihydropyridyl[2,3-b]pyrazin-3(4H)-one, 2H-pyridyl[3,2-b][1,4]oxazin-3(4H)-one, 3,4-dihydropyridyl[2,3-d]pyrimidin-2 (1H)-one, imidazopyridinyl, and tetrahydroquinazolinyl.

Exemplary rings that are formed when two independent occurrences of Y$_1$ and Q$_1$, Y$_3$ and Q$_2$, or Y$_4$ and Y$_5$ are taken together with their intervening atom(s) include, but are not limited to the following: indolyl, indazolyl, 4H-furo[3,2-b]pyrrolyl, 4H-thieno[3,2-b]pyrrolyl, 5H-furo[2,3-b]pyrrolyl, 5H-thieno[2,3-b]pyrrolyl, pyrrolo[3,4-b]pyrrolyl, pyrrolo[3,2-b]pyrrolyl, pyrrolo[2,3-b]pyrrolyl, dihydropyrrolo[3,2-b]pyrrolyl, dihydropyrrolo[2,3-b]pyrrolyl, 5H-pyrrolo[3,2-b]oxazole, 5H-pyrrolo[3,2-d]thiazole, pyrrolopyrimidinyl, pyrrolopyridinyl, pyrazolopyrimidinyl and pyrazolopyridinyl.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures where there is a replacement of hydrogen by deuterium or tritium, or a replacement of a carbon by a $^{13}$C- or $^{14}$C-enriched carbon are within the scope of this invention. Such compounds are useful, as a nonlimiting example, as analytical tools or probes in biological assays.

It is to be understood that, when a disclosed compound has at least one chiral center, the present invention encompasses one enantiomer of inhibitor free from the corresponding optical isomer, racemic mixture of the inhibitor and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95% 99% or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present invention encompasses a diastereomer free of other diastereomers, a pair of diastereomers free from other diasteromeric pairs, mixtures of diasteromers, mixtures of diasteromeric pairs, mixtures of diasteromers in which one diastereomer is enriched relative to the other diastereomer(s) and mixtures of diasteromeric pairs in which one diastereomeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diastereomeric pair(s) relative to other diastereomers or diastereomeric pair(s) for the compound, for example, by a molar excess of at least 50%, 75%, 90%, 95%, 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

3. Description of Exemplary Compounds

In certain embodiments, for compounds of general formula IA or IB, $R^1$ is CY and CY is:

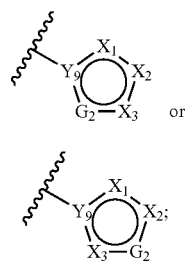

wherein:
$X_1$, $X_2$, and $X_3$, are each independently N, O, S, $NR^{4'}$, or $CR^7$, provided that only one of
$X_1$, $X_2$, or $X_3$ may be O or S;
$Y_9$ is N or $CR^7$;
$G_2$ is $CR^{7'}$, —N= or —$NR^{4'}$—, wherein:
$R^{4'}$ is independently hydrogen, —$Z_2$—$R^6$, optionally substituted
$C_{1-6}$ aliphatic, or optionally substituted 3-10-membered cycloaliphatic, wherein:
$Z_2$ is selected from an optionally substituted $C_{1-3}$ alkylene chain, —S(O)—, —S(O)$_2$—, —C(O)—, —CO$_2$—, —C(O)$NR^{4a}$—, or —S(O)$_2NR^{4a}$—,
$R^{4a}$ is hydrogen or an optionally substituted $C_{1-4}$ aliphatic, and
$R^6$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of $R^7$ and $R^{7'}$ is independently hydrogen, —CN, halogen, —$Z_3$—$R^8$, $C_{1-6}$ aliphatic, or 3-10-membered cycloaliphatic, wherein:
$Z_3$ is selected from an optionally substituted $C_{1-3}$ alkylene chain, —O—, —$N(R^{7a})$—, —S—, —S(O)—, —S(O)$_2$—, —C(O)—, —CO$_2$—, —C(O)$NR^{7a}$—, —$N(R^{7a})C(O)$—, —$N(R^{7a})CO_2$—, —S(O)$_2NR^{7a}$—, —$N(R^{7a})S(O)_2$—, —OC(O)$N(R^{7a})$—, —$N(R^{7a})C(O)NR^{7a}$—, —$N(R^{7a})S(O)_2N(R^{7a})$—, or —OC(O)—;
$R^{7a}$ is hydrogen or an optionally substituted $C_{1-4}$ aliphatic, and
$R^8$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

In certain other embodiments, for compounds of general formula IA or IB, $R^1$ is CY and CY is

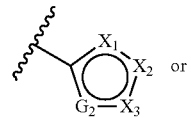

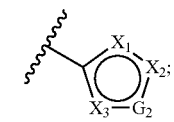

is wherein:
$X_1$, $X_2$, and $X_3$, are each independently N, O, S, $NR^{4'}$, or $CR^7$, provided that only one of
$X_1$, $X_2$, or $X_3$ may be O or S, $G_2$ is $CR^{7'}$, —N= or —$NR^{4'}$—, wherein:
$R^{4'}$ is independently H, —$Z_2$—$R^6$, optionally substituted $C_{1-6}$ aliphatic, or optionally substituted 3-10-membered cycloaliphatic, wherein:
$Z_2$ is selected from an optionally substituted $C_{1-3}$ alkylene chain, —S(O)—, —S(O)$_2$—, —C(O)—, —CO$_2$—, —C(O)$NR^{4a}$—, or —S(O)$_2NR^{4a}$—.
$R^{4a}$ is hydrogen or an optionally substituted $C_{1-4}$ aliphatic, and
$R^6$ is an optionally substituted group selected from $C_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur;
each occurrence of $R^7$ or $R^{7'}$ is independently hydrogen, —CN, halogen, —$Z_3$—$R^8$, $C_{1-6}$ aliphatic, or 3-10-membered cycloaliphatic, wherein:
$Z_3$ is selected from an optionally substituted $C_{1-3}$ alkylene chain, —O—, —S—, —S(O)—, —S(O)$_2$—, —C(O)—, —CO$_2$—, —C(O)NR$^{7a}$—, —N(R$^{7a}$)C(O)—, —N(R$^{7a}$)CO$_2$—, —S(O)$_2$NR$^{7a}$—, —N(R$^{7a}$)S(O)$_2$—, —OC(O)N(R$^{7a}$)—, —N(R$^{7a}$)C(O)NR$^{7a}$—, —N(R$^{7a}$)S(O)$_2$N(R$^{7a}$)—, or —OC(O)—.

R$^{7a}$ is hydrogen or an optionally substituted C$_{1-4}$ aliphatic, and

R$^8$ is an optionally substituted group selected from C$_{1-6}$ aliphatic, 3-10-membered cycloaliphatic, 4-10-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

In other embodiments, for compounds described directly above, R$^1$ is CY and CY is

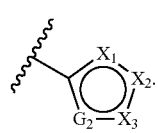

In still other embodiments, for compounds described directly above, R$^1$ is CY and CY is:

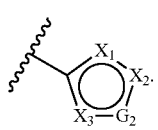

In still other embodiments, X$_1$ is N, G$_2$ is N(R$^{4'}$), and X$_2$ and X$_3$ are CH.

In yet other embodiments, X$_1$ and X$_2$ are N, G$_2$ is N(R$^{4'}$), and X$_3$ is CH.

In other embodiments, X$_3$ is N, G$_2$ is N(R$^{4'}$), and X$_1$ and X$_2$ are CH.

In yet other embodiments, X$_1$ is N(R$^{4'}$), G$_2$ is N, and X$_2$ and X$_3$ are CH.

In still other embodiments, X$_1$ and G$_2$ are N, X$_3$ is N(R$^{4'}$), and X$_2$ is CH.

In yet other embodiments, X$_1$ and X$_2$ are CH, G$_2$ is N, and X$_3$ is N(R$^{4'}$). In still other embodiments, X$_2$ and G$_2$ are CH, X$_1$ is N, and X$_3$ is N(R$^{4'}$).

In other embodiments, G$_2$ is N, X$_3$ is CH$_2$, X$_2$ is N(R$^{4'}$), and X$_1$ is N.

In still other embodiments, R$^1$ is an optionally substituted 6-membered aryl or heteroaryl ring.

In other embodiments, R$^1$ is selected from:

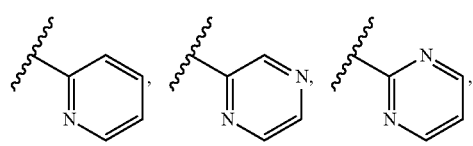

-continued

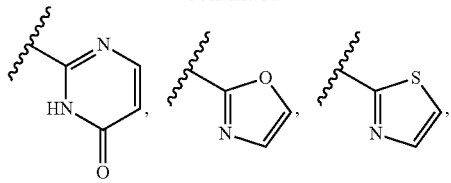

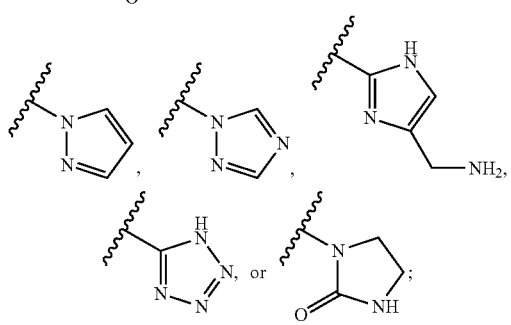

wherein R$^1$ is optionally further substituted with one or more occurrences of R$^7$ or R$^{4'}$ In yet other embodiments, R$^1$ is selected from:

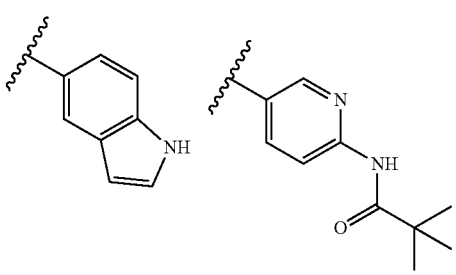

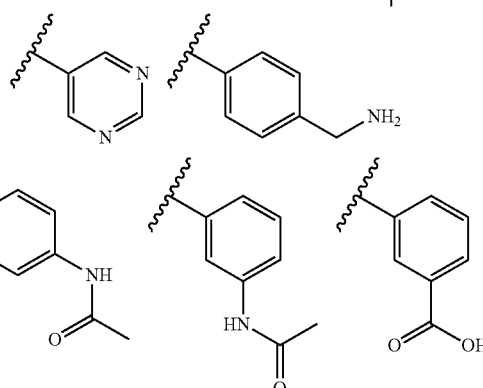

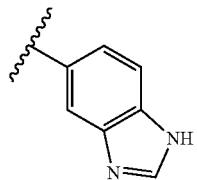 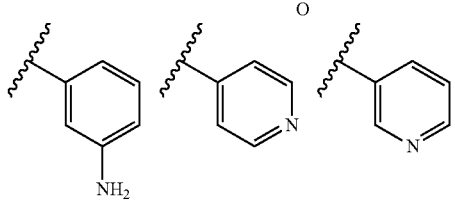 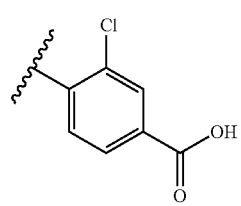

-continued

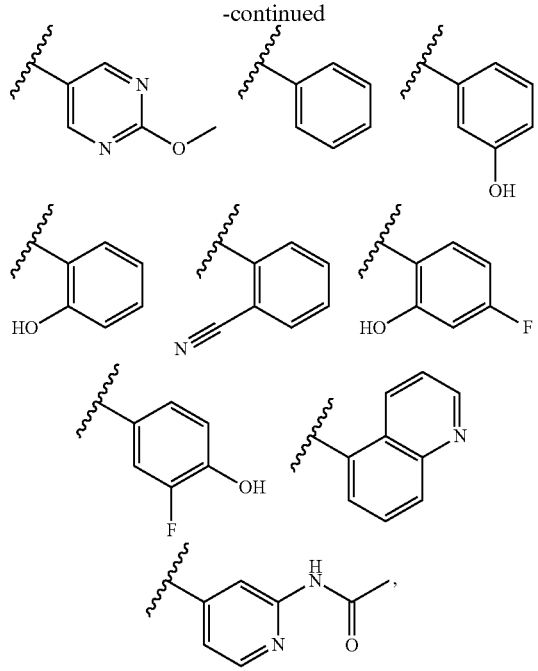

wherein R¹ is optionally further substituted with one or more occurrences of R⁷ or R⁴'

In other embodiments, R¹ is CON(R⁴)₂ or COOR⁴.

In still other embodiments, R¹ is COOR⁴.

In yet other embodiments, R¹ is COOR⁴ or CY and CY is

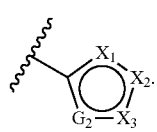

i

In still other embodiments, R¹ is CON(R⁴)₂.

In some embodiments, when R¹ is CON(R⁴)₂, each occurrence of R⁴ is independently hydrogen, —Z₂—R⁶, optionally substituted $C_{1-6}$aliphatic, optionally substituted $C_{3-7}$cycloaliphatic, optionally substituted $C_{3-7}$heterocyclyl, or optionally substituted 5-6-membered aryl or heteroaryl ring.

In other embodiments, when R¹ is CON(R⁴)₂, each occurrence of R⁴ is independently hydrogen, —Z₂—R⁶, or optionally substituted $C_{1-6}$aliphatic. In certain embodiments, Z₂ is $C_{1-3}$ aliphatic and R⁶ is —OR⁴ᵃ or an optionally substituted $C_{3-7}$cycloaliphatic, optionally substituted $C_{3-7}$heterocyclyl, or optionally substituted 5-6-membered aryl or heteroaryl ring.

In some embodiments for compounds of formula I-A or I-B, HY is an optionally substituted group selected from:

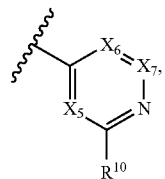

H

-continued

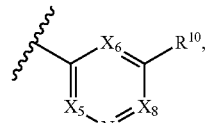

J

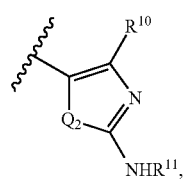

K

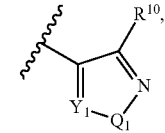

L

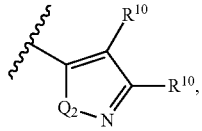

M

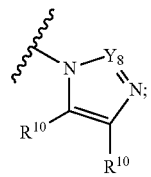

N

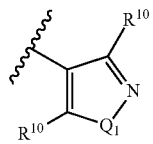

O

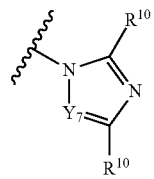

P

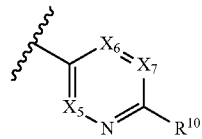

Q wherein each occurrence of X₅, X₆, and X₇ is independently —CR¹⁰ or N, provided no more than two occurrences of X₅, X₆, and X₇ are N;

each occurrence of Q₁ and Q₂ is independently S, O or —NR⁹;

each occurrence of Y₁, Y₇, and Y₈ is independently —CR¹⁰ or N;

or wherein two adjacent occurrences of X₆, and X₇, Y₁ and Q₁, or two adjacent occurrences of R¹⁰, taken together with the atom to which they are bound, form an optionally substituted fused group selected from 5-6-membered aryl, or 5-6-membered heteroaryl having 1-5 heteroatoms independently selected from nitrogen, oxygen, or sulfur.

In still other embodiments, HY is selected from:

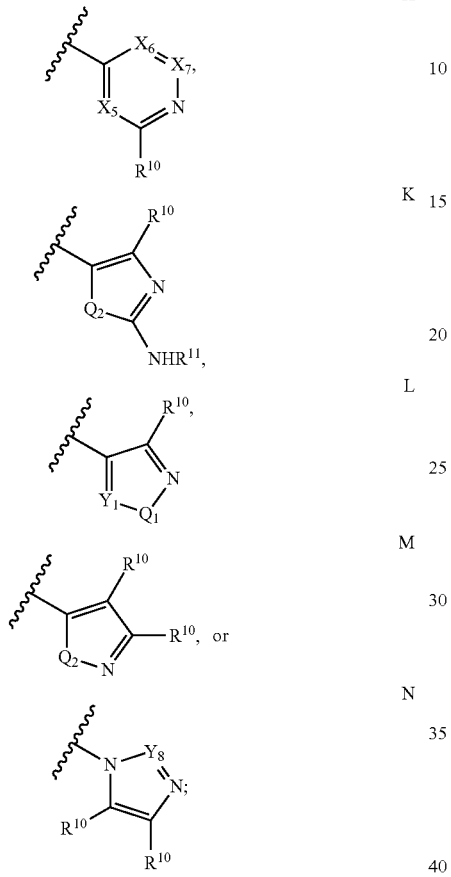

wherein each occurrence of $X_5$, $X_6$, and $X_7$ is independently —$CR^{10}$ or N, provided no more than two occurrences of $X_5$, $X_6$, and $X_7$ are N;

each occurrence of $Q_1$ and $Q_2$ is independently S, O or —$NR^9$;

each occurrence of $Y_1$, $Y_7$, and $Y_8$ is independently —$CR^{10}$ or —$NR^9$;

or wherein two adjacent occurrences of $X_6$, and $X_7$, $Y_1$ and $Q_1$, or two adjacent occurrences of $R^{10}$, taken together with the atom to which they are bound, form an optionally substituted fused group selected from 5-6-membered aryl, or 5-6-membered heteroaryl having 1-5 heteroatoms independently selected from nitrogen, oxygen, or sulfur.

In yet other embodiments, HY is selected from:

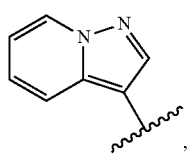  i

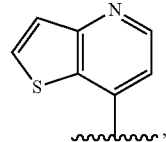 ii

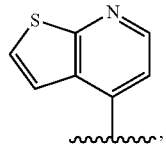 iii

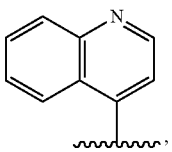 iv

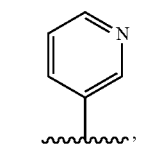 v

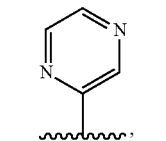 vi

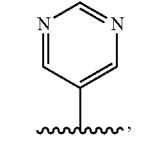 vii

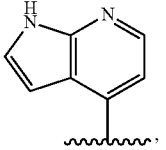 viii

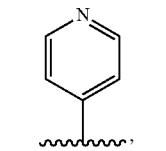 ix

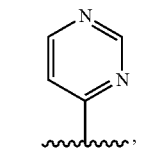 x

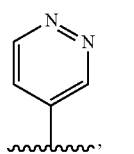 xi

-continued
xii 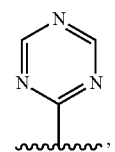
xiii 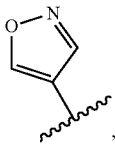
xiv 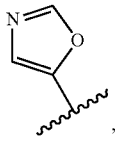
xv 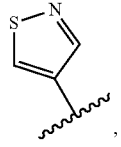
xvi 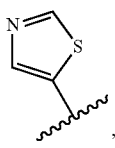
xvii 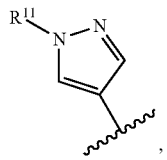
xviii 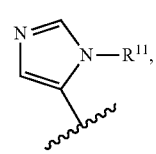
xvix 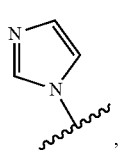
xvx 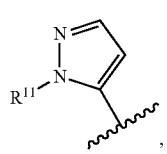
xvxi 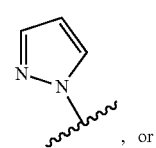, or
xvxii 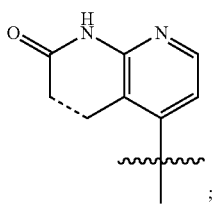;
wherein each HY group is optionally additionally substituted with one or more occurrences of $R^{10}$, and the dashed line in xvxii represents a single bond or a double bond.
In yet other embodiments, HY is selected from:
i 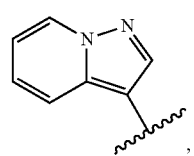,
ii 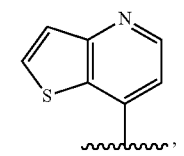,
iii 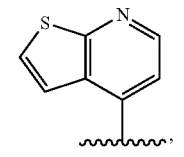,
iv 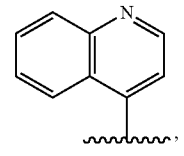,
v 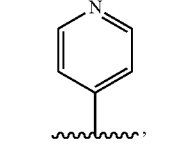,
vi 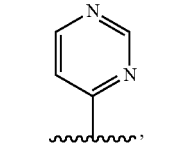,
vii 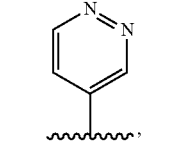,

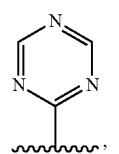, viii
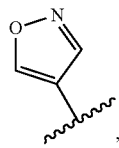, ix
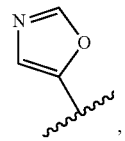, x
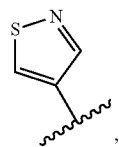, xi
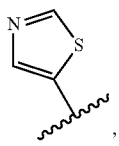, xii
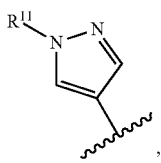, xiii
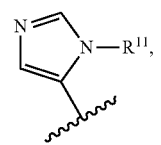, xiv
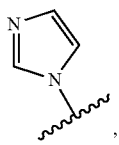, xv
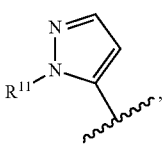, xvi
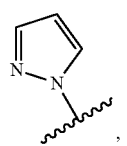,
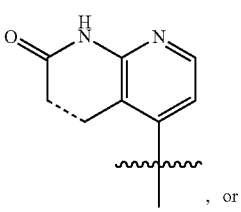, xviii
or
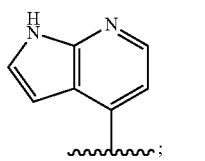; xvix
wherein each HY group is optionally additionally substituted with one or more occurrences of $R^{10}$, and the dashed line in xviii represents a single bond or a double bond.
In still other embodiments, HY is selected from:
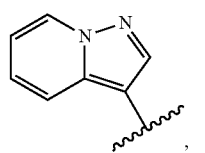, i
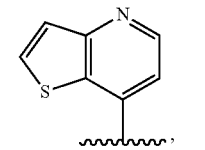, ii
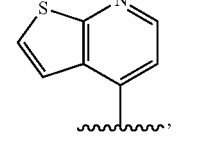, iii
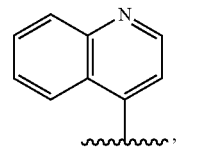, iv
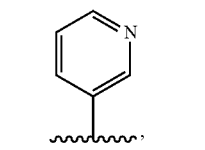, v
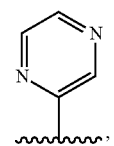; vi -continued

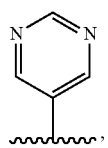
vii

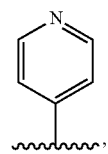
ix

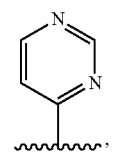
x

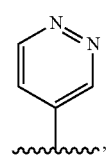
xi

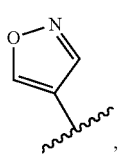
xiii

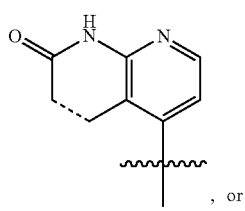
xvxii

, or

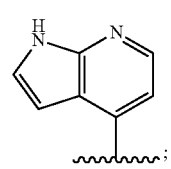
viii

;

wherein each HY group is optionally additionally substituted with one or more occurrences of $R^{10}$, and the dashed line in xvxii represents a single bond or a double bond.

In still other embodiments, HY is selected from:

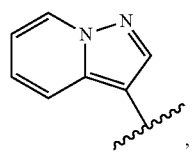
i

,

-continued

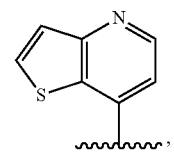
ii

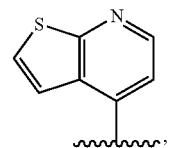
iii

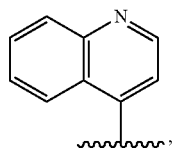
iv

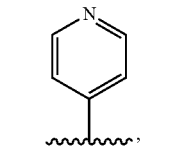
v

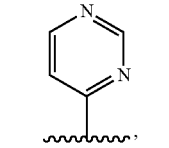
vi vii ix xviii

, or xvix

;

wherein each HY group is optionally additionally substituted with one or more occurrences of $R^{10}$, and the dashed line in xviii represents a single bond or a double bond.

In yet other embodiments, HY is selected from:

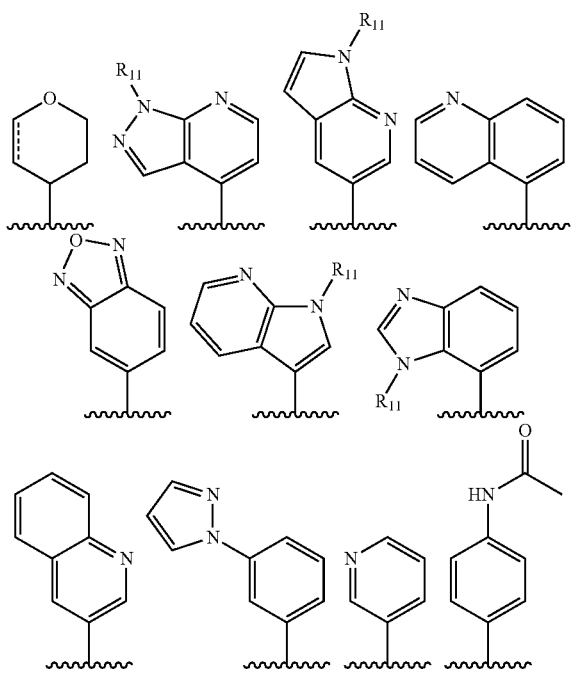

wherein HY is additionally optionally substituted at one or more carbon atoms with one or more occurrences of $R^{10}$.

In still other embodiments, HY is selected from

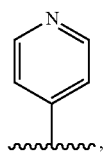

(v)

wherein HY is additionally optionally substituted with one or more occurrences of $R^{10}$.

In yet other embodiments for compounds of general formula IA and IB, HY is

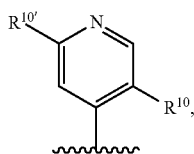

wherein $R^{10'}$ is NHCOR$^{10c}$ or —NHCOOR$^{10c}$ and wherein $R^1$, $R^2$ and $R^{10}$ are as defined generally and in subsets herein.

In yet other embodiments for compounds of general formula IA and IB, HY is

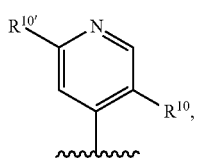

wherein $R^{10'}$ is NHCOR$^{10c}$ and wherein $R^1$, $R^2$ and $R^{10}$ are as defined generally and in subsets herein.

In yet other embodiments, HY is

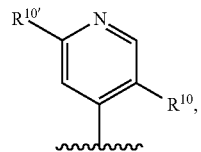

wherein $R^{10}$ is hydrogen, methyl, chloro, bromo, fluoro, CN, CF$_3$, OR$^{10c}$, COR$^{10c}$, and $R^{10'}$ is NHCOR$^{10c}$ or —NHCOOR$^{10c}$.

In still other embodiments, $G_1$ is $C(R^3)$.

In yet other embodiments, $G_1$ is CH.

In other embodiments, $G_1$ is N.

In other embodiments, $R^2$ is a 6-10-membered aryl or 5-10-membered heteroaryl having 1-5 heteroatoms independently selected from nitrogen, oxygen, or sulfur; optionally substituted with 1-3 occurrences of $R^{2a}$.

In yet other embodiments, $R^2$ is a phenyl group; optionally substituted with one or more independent occurrences of halogen, C$_{1-3}$ alkyl, C$_{3-6}$cycloalkyl, C$_{3-6}$heterocyclyl, —CN, C$_{1-3}$ haloalkyl, —(CH$_2$)$_p$N(R$^{12}$)$_2$, —OR$^{12b}$, —NHC(O)R$^{12b}$, —NHC(O)NHR$^{12b}$, —NHS(O)$_2$R$^{12b}$, C(O)OR$^{12b}$, —C(O)N(R$^{12b}$)$_2$, or —C(O)R$^{12b}$.

In yet other embodiments, $R^2$ is a phenyl group; optionally substituted with one or more independent occurrences of halogen, C$_{1-3}$ alkyl, —CN, C$_{1-3}$haloalkyl, —CH$_2$N(R$^{12b}$)$_2$, —OC$_{1-3}$ alkyl, —OC$_{1-3}$ haloalkyl, —NHC(O)C$_{1-3}$ alkyl, —NHC(O)NHC$_{1-3}$ alkyl, —NHS(O)$_2$C$_{1-3}$ alkyl, or —C(O)H.

In yet other embodiments, $R^2$ is a phenyl group; optionally substituted with one or more independent occurrences of halogen, C$_{1-3}$ alkyl, —CN, C$_{1-3}$ haloalkyl, —CH$_2$N(CH$_3$)$_2$, —OC$_{1-3}$ alkyl, —OC$_{1-3}$haloalkyl, —NHC(O)C$_{1-3}$ alkyl, —NHC(O)NHC$_{1-3}$ alkyl, —NHS(O)$_2$C$_{1-3}$ alkyl, or —C(O)H.

In still other embodiments, $R^2$ is a phenyl group substituted with 1 or 2 occurrences of halogen.

In yet other embodiments, $R^2$ is a phenyl group substituted with 1 occurrence of halogen. In certain embodiments, the halogen is Cl.

In still other embodiments, $R^2$ is a phenyl group substituted with 1 occurrence of halogen in the meta position. In certain embodiments, the halogen is Cl.

In yet other embodiments, $R^2$ is a phenyl group substituted with 1 occurrence of halogen in the meta position and is further substituted with 1 occurrence of $R^{2a}$. In certain embodiments, the halogen is Cl and $R^{2a}$ is —CH$_2$N(R$^{12b}$)$_2$ In yet other embodiments, $R^2$ is a 3-10-membered cycloaliphatic, 4-10-membered heterocyclyl having 1-5 heteroatoms independently selected from nitrogen, oxygen, or sulfur.

In still other embodiments, $R^2$ is an optionally substituted N-linked 3-, 4-, 5-, 6-, or 7-membered heterocyclyl ring. In some embodiments, the wherein the N-linked 3-, 4-, 5-, 6-, or 7-membered heterocyclyl ring is optionally substituted with one or more occurrences of $R^{2a}$.

In some embodiments, $R^2$ is an optionally substituted N-linked 5- or 6-membered ring optionally substituted with one or more occurrences of $R^{2a}$.

In some embodiments, the ring is optionally substituted with one or more C$_{1-3}$alkyl groups.

In still other embodiments of the invention, compounds of formula I-A are provided wherein:
(a) $R^1$ is $CON(R^4)_2$ or CY;
(b) $R^2$ is phenyl substituted with one or more occurrences of $R^{2a}$; and
(c) HY is

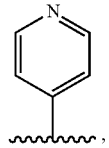, wherein HY is additionally optionally substituted with one or more occurrences of $R^{10}$ In yet other embodiments of the invention, compounds of formula I-B are provided wherein:
(a) $R^1$ is $CON(R^4)_2$ or CY;
(b) $R^2$ is phenyl substituted with one or more occurrences of $R^{2a}$; and
(c) HY is

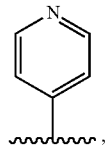, wherein HY is additionally optionally substituted with one or more occurrences of $R^{10}$ It will be appreciated that the description of $R^1$, $R^2$, and HY directly above also include the additional subsets and species for $R^1$, $R^2$ and HY described above and herein.

General Synthetic Methods and Intermediates:

The compounds of the present invention can be prepared by methods known to one of ordinary skill in the art and/or by reference to the schemes shown below and the synthetic examples that follow. Exemplary synthetic routes are set forth in the Schemes below, and in the Examples.

Examples of the solvent for the below-mentioned reactions include, but are not limited to halogenated hydrocarbons such as dichloromethane, chloroform, carbon tetrachloride, 1,2-dichloroethane and the like, aromatic hydrocarbons such as benzene, toluene, xylene and the like, alcohols such as methanol, ethanol, isopropanol, tert-butanol, phenol and the like, ethers such as diethyl ether, tetrahydrofuran, dioxane, DME and the like, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like.

One of ordinary skill in the art will recognize that numerous variations in reaction conditions including variations in solvent, reagents, catalysts, reaction temperatures and times are possible for each of the reactions described. Variation of order of synthetic steps and alternative synthetic routes are also possible.

In many cases, synthesis can be started from commercially available furan/oxazole analogs to prepare target compounds. In some cases, specially functionalized furan/oxazole analogs can be prepared by the procedures described in the Schemes below.

The compounds of the present invention can be prepared by methods known to one of ordinary skill in the art and/or by reference to the schemes shown below and the synthetic examples that follow.

Scheme 1: General method for the synthesis of oxazoles

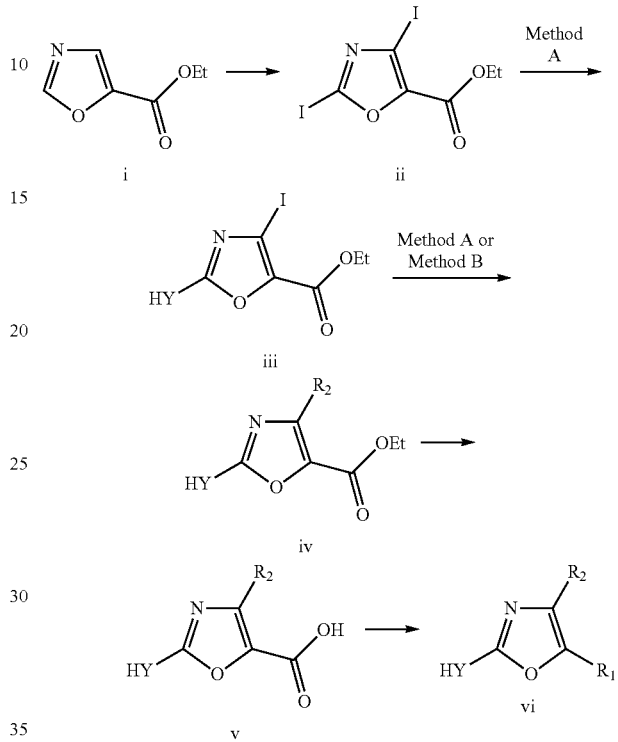

Scheme 1 describes a method of preparing substituted oxazoles vi. Treatment of ethyl 1,3-oxazole-5-carboxylate with lithium hexamethyldisilazane and iodine in DMPU gives ii as reported in the literature (Vedejs, E., Luchetta, L. M. *J. Org. Chem.* 1999, 64, 1011). Compounds iii can then be prepared from compounds ii by Method A. Method A is the coupling reaction of an aryl or heteroaryl bromide with an appropriate aryl or heteroaryl stannane under suitable conditions, for example $Pd(PPh_3)_4$, CuI, LiCl in an appropriate solvent, such as dioxane, at elevated temperature. Alternatively, Method A can refer to the coupling reaction of an aryl or heteroaryl bromide with an appropriate boronic acid or boronic ester under suitable conditions, for example $Pd(PPh_3)_4$, $Cs_2CO_3$, in an appropriate solvent, such as dioxane, at elevated temperature or under microwave irradiation. Method A can subsequently be used to prepare compounds iv from iii when $R_2$ is an aromatic or heteroaromatic group. When $R_2$ is a substituted amino group, compounds iv can be prepared by Method B. Method B is the coupling of an aryl or heteroaryl bromide with an amine under suitable conditions, for example $Pd_2(dba)_3$, xantphos, $Cs_2CO_3$, in an appropriate solvent, such as dioxane, at elevated temperature or under microwave irradiation. Alternatively, Method B can refer to the direct displacement of a halogen by an amine under suitable conditions, for example reaction in an appropriate solvent, such as DMSO, at an elevated temperature or under microwave irradiation. Compounds vi can be prepared via the intermediate acids v (obtained by hydrolysis of the ester of compounds iv under standard conditions) or by transformation of the esters iv directly to a variety of groups using standard methods.

Scheme 2: Alternate general method for the synthesis of oxazoles vi

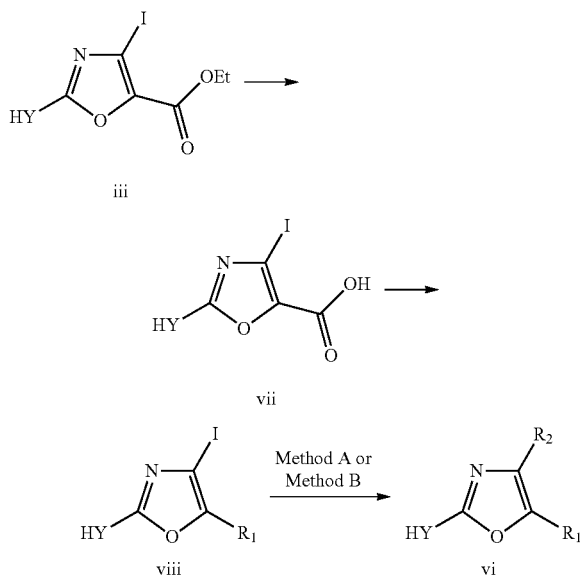

Scheme 2 describes an alternative method of preparing substituted oxazoles vi. Compounds vi can be prepared via the intermediate acids vii (obtained by hydrolysis of the ester of compounds iii under standard conditions) or by transformation of the esters iii directly to a variety of groups using standard methods. Oxazoles vi can be prepared from viii by reaction according to Method A or Method B.

Scheme 3: General method for the synthesis of oxazoles xv

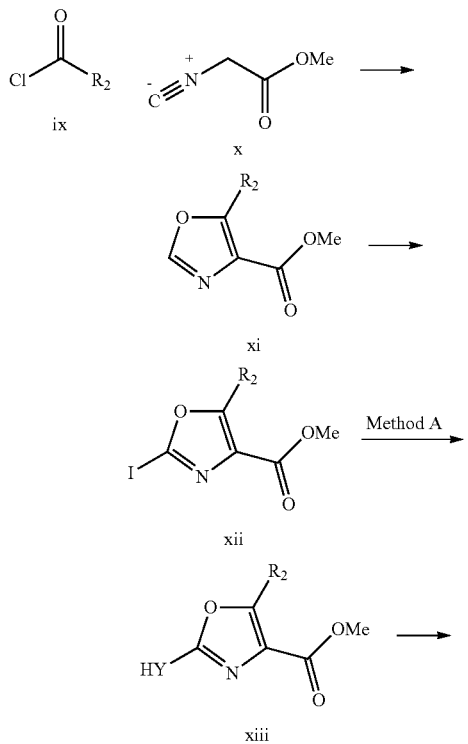

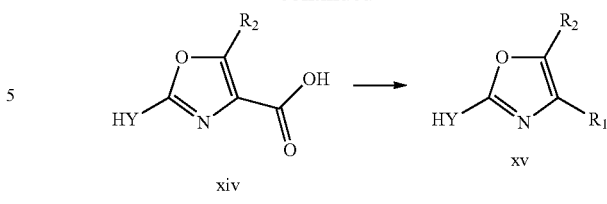

Scheme 3 describes a method of preparing substituted oxazoles xv. Acid chlorides ix can be reacted with methyl isocyanoacetate (x) according to procedures described in the literature (e.g., Hirashima, S. et al. *J. Med. Chem.* 2006, 49, 4721). The resulting oxazoles xi can be iodinated under standard conditions, for example treatment with lithium hexamethyldisilazine and iodine in a solvent such as THF to give iodides xii. The oxazoles xiii can be prepared from xii using Method A. Compounds xiii can be elaborated to oxazoles xv through a series of standard transformations as described for the preparation of compounds vi from iv in Scheme 1.

Scheme 4: Alternate general method for the synthesis of oxazoles xv

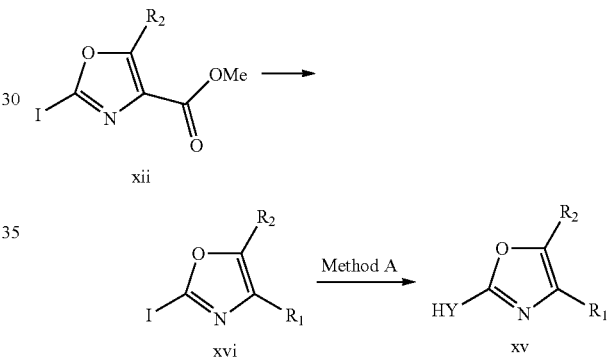

Scheme 4 describes an alternative method of preparing substituted oxazoles xv. Compounds xvi can be prepared from esters xii through a series of standard transformations as described for the preparation of compounds vi from iv in Scheme 1. Compounds xvi can be elaborated to oxazoles xv using Method A.

Scheme 5: General route for the synthesis of substituted furans xxi

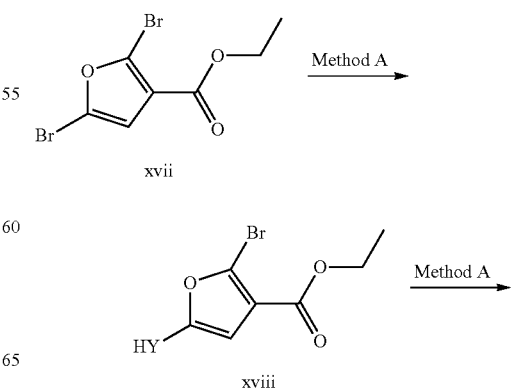

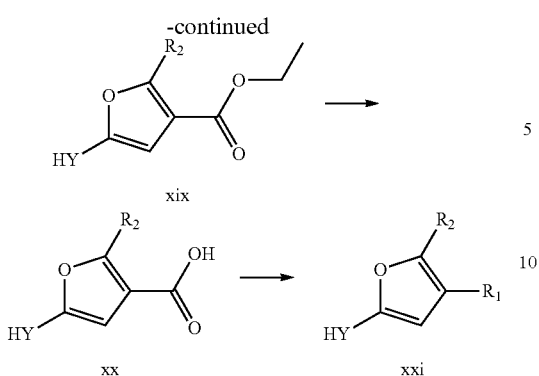

Scheme 5 describes a general method for preparation of furans of formula xxi. Ethyl 5-[2-(acetylamino)pyridin-4-yl]-2-bromo-3-furoate xvii can be transformed according to Method A to furan xviii. Reaction again according to Method A or Method B can be used as a method to prepare compounds xix. Compounds xxi can be prepared from esters xix through a series of standard transformations as described for the preparation of compounds vi from iv in Scheme 1.

Scheme 5: Alternate general route for the synthesis of substituted furans xxi

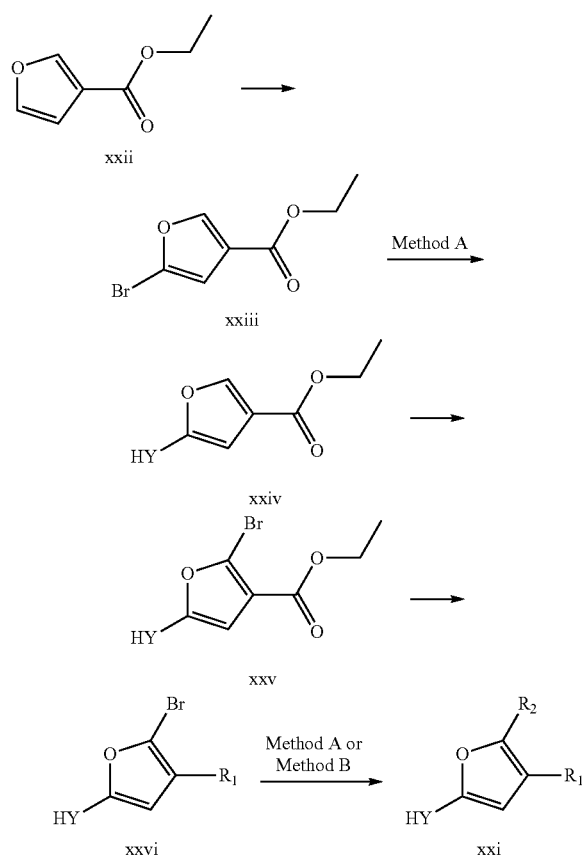

Scheme 6 describes an alternative a general method for preparation of furans of formula xxi. Furan xxii can be halogenated under standard conditions, for example treatment with bromine in a suitable solvent, such as chloroform, at an appropriate temperature. The bromides xxiii can then be transformed according to Method A to furans xxiv. Compounds xxiv can also undergo bromination under standard conditions, for example treatment with NBS in a suitable solvent, such as DMF, at an appropriate temperature, such as 80° C., to give bromides xxv. Compounds xxvi can be prepared from esters xxv through a series of standard transformations as described for the preparation of compounds vi from iv in Scheme 1. Compounds xxxvi can be transformed to furans xxi by either Method A or Method B.

4. Uses, Formulation and Administration

As discussed above, the present invention provides compounds that are useful as inhibitors of VPS34 and/or PI3K, and thus the present compounds are useful for treating proliferative, inflammatory, or cardiovascular disorders such as tumor and/or cancerous cell growth mediated by VPS34 and/or PI3K. In particular, the compounds are useful in the treatment of cancers in a subject, including, but not limited to, lung and bronchus, prostate, breast, pancreas, colon and recum, thyroid, liver and intrahepatic bile duct, hepatocellular, gastric, glioma/glioblastoma, endometrial, melanoma, kidney, and renal pelvis, urinary bladder, uterine corpus, uterine cervix, ovary, multiple myeloma, esophagus, acute myelogenous leukemia, chronic myelogenous leukemia, lymphocytic leukemia, myeloid leukemia, brain, oral cavity, and pharynx, small intestine, non-Hodgkin lymphoma, and villous colon adenoma.

In some embodiments, compounds of the invention are suitable for the treatment of breast cancer, bladder cancer, colon cancer, glioma, glioblastoma, lung cancer, hepatocellular cancer, gastric cancer, melanoma, thyroid cancer, endometrial cancer, renal cancer, cervical cancer, pancreatic cancer, esophageal cancer, prostate cancer, brain cancer, or ovarian cancer.

In other embodiments, compounds of the invention are suitable for the treatment of inflammatory and cardiovascular disorders including, but not limited to, allergies/anaphylaxis, acute and chronic inflammation, rheumatoid arthritis; autoimmunity disorders, thrombosis, hypertension, cardiac hypertrophy, and heart failure.

Accordingly, in another aspect of the present invention, pharmaceutical compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of VPS34 and/or PI3K.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for treating a proliferative, inflammatory, or cardiovascular disorder is provided comprising administering an effective amount of a compound, or a pharmaceutical composition to a subject in need thereof. In certain embodiments of the present invention an "effective amount" of the compound or pharmaceutical composition is that amount effective for treating a proliferative, inflammatory, or cardiovascular disorder, or is that amount effective for treating cancer. In other embodiments, an "effective amount" of a compound is an amount which inhibits binding of PI3K and thereby blocks the resulting signaling cascades that lead to the abnormal activity of growth factors, receptor tyrosine kinases, protein serine/threonine kinases, G protein coupled receptors and phospholipid kinases and phosphatases.

The compounds and compositions, according to the method of the present invention, may be administered using any amount and any route of administration effective for treating the disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disease being treated and the severity of the disease; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

While one or more of the inventive compounds may be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the therapeutic agents concurrently or sequentially. Alternatively, the therapeutic agents can be combined into one composition which is administered to the patient.

In one embodiment, the compounds of this invention are used in combination with other therapeutic agents, such as other inhibitors of VPS34 and/or PI3K. In some embodiments, a compound of the invention is administered in conjunction with a therapeutic agent selected from the group consisting of cytotoxic agents, radiotherapy, and immunotherapy. It is understood that other combinations may be undertaken while remaining within the scope of the invention.

Another aspect of the invention relates to inhibiting VPS34 and/or PI3K, activity in a biological sample or a patient, which method comprises administering to the patient, or contacting said biological sample with a compound of formula I or a composition comprising said compound. The term "biological sample", as used herein, generally includes in vivo, in vitro, and ex vivo materials, and also includes, without limitation, cell cultures or extracts thereof; biopsied material obtained from a mammal or extracts thereof; and blood, saliva, urine, feces, semen, tears, or other body fluids or extracts thereof.

Still another aspect of this invention is to provide a kit comprising separate containers in a single package, wherein the inventive pharmaceutical compounds, compositions and/or salts thereof are used in combination with pharmaceutically acceptable carriers to treat disorders, symptoms and diseases where VPS34 and/or PI3K kinase plays a role.

EXPERIMENTAL PROCEDURES

I-A. Preparation of Certain Exemplary Compounds

Compounds (Shown in Table 1 below) were prepared using the general methods and specific examples described directly below.

EXAMPLES

Table 1 below depicts certain compounds represented by compounds of general formula IA and IB.

TABLE 1

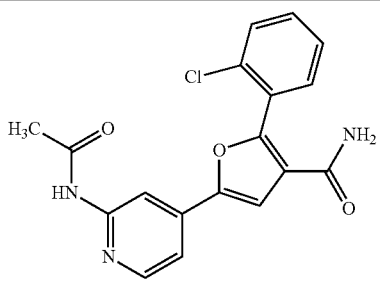 [SMILES: CC(=O)Nc1cc(-c2cc(C(N)=O)c(-c3ccccc3Cl)o2)ccn1]

I-1

TABLE 1-continued

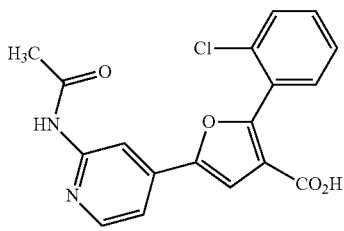 [SMILES: CC(=O)Nc1cc(-c2cc(C(=O)O)c(-c3ccccc3Cl)o2)ccn1]

I-2

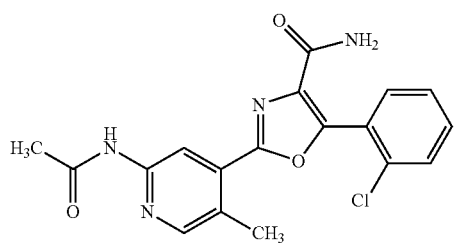 [SMILES: CC(=O)Nc1cc(-c2nc(C(N)=O)c(-c3ccccc3Cl)o2)c(C)cn1]

I-3

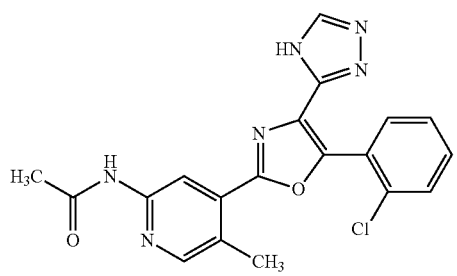 [SMILES: CC(=O)Nc1cc(-c2nc(-c3nnc[nH]3)c(-c3ccccc3Cl)o2)c(C)cn1]

I-4

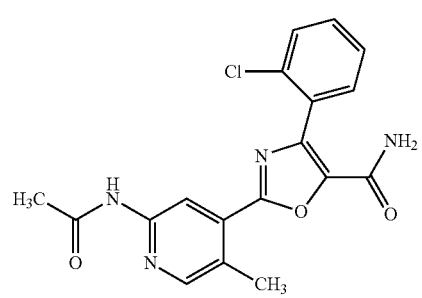 [SMILES: CC(=O)Nc1cc(-c2nc(-c3ccccc3Cl)c(C(N)=O)o2)c(C)cn1]

I-5

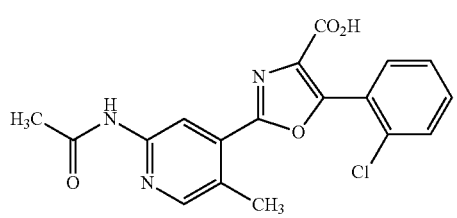 [SMILES: CC(=O)Nc1cc(-c2nc(C(=O)O)c(-c3ccccc3Cl)o2)c(C)cn1]

I-6

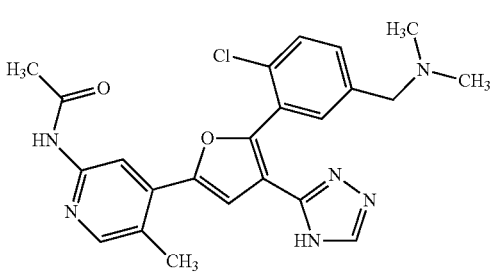 [SMILES: CC(=O)Nc1cc(-c2cc(-c3nnc[nH]3)c(-c3cc(CN(C)C)ccc3Cl)o2)c(C)cn1]

I-7

TABLE 1-continued
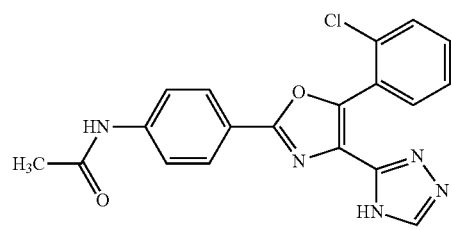 [SMILES: CC(=O)Nc1ccc(-c2nc(-c3nnc[nH]3)c(-c3ccccc3Cl)o2)cc1] I-8
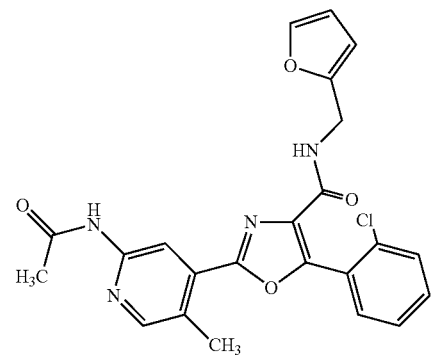 I-9
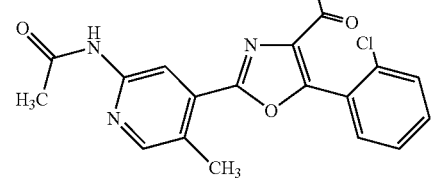 I-10
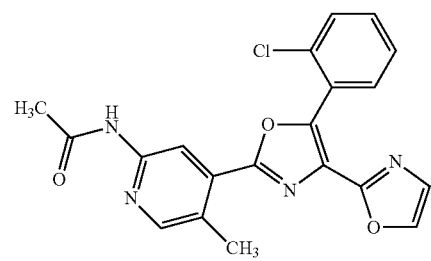 [SMILES: CC(=O)Nc1cc(-c2nc(-c3ncco3)c(-c3ccccc3Cl)o2)c(C)cn1] I-11
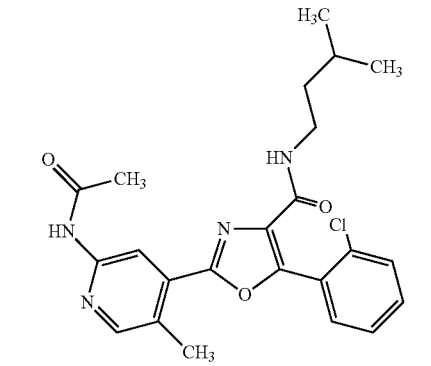 [SMILES: CC(=O)Nc1cc(-c2nc(C(=O)NCCC(C)C)c(-c3ccccc3Cl)o2)c(C)cn1] I-12
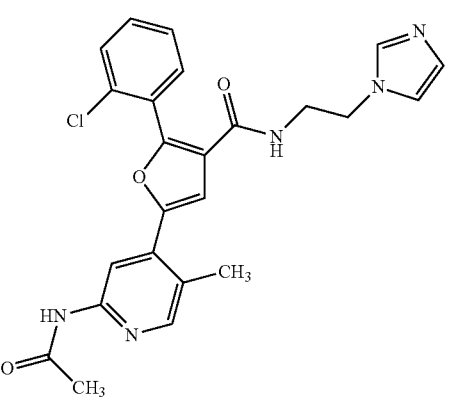 [SMILES: CC(=O)Nc1cc(-c2cc(C(=O)NCCn3ccnc3)c(-c3ccccc3Cl)o2)c(C)cn1] 
TABLE 1-continued
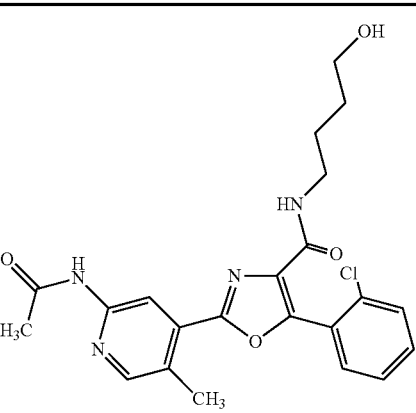 I-13
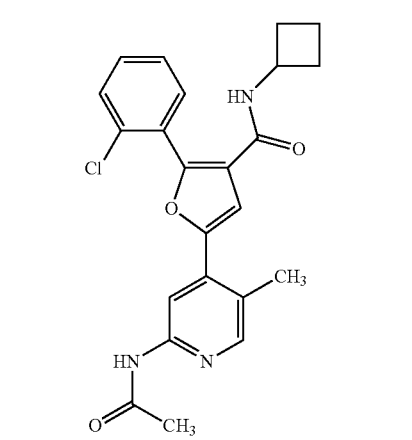 [SMILES: CC(=O)Nc1cc(-c2cc(C(=O)NC3CCC3)c(-c3ccccc3Cl)o2)c(C)cn1] I-14
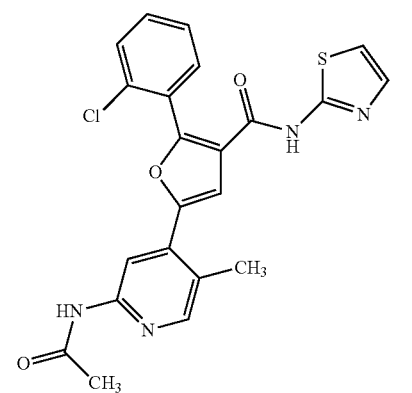 [SMILES: CC(=O)Nc1cc(-c2cc(C(=O)Nc3nccs3)c(-c3ccccc3Cl)o2)c(C)cn1] I-15
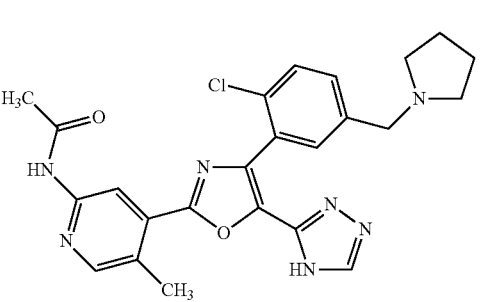 [SMILES: CC(=O)Nc1cc(-c2nc(-c3cc(CN4CCCC4)ccc3Cl)c(-c3nnc[nH]3)o2)c(C)cn1] I-16

TABLE 1-continued
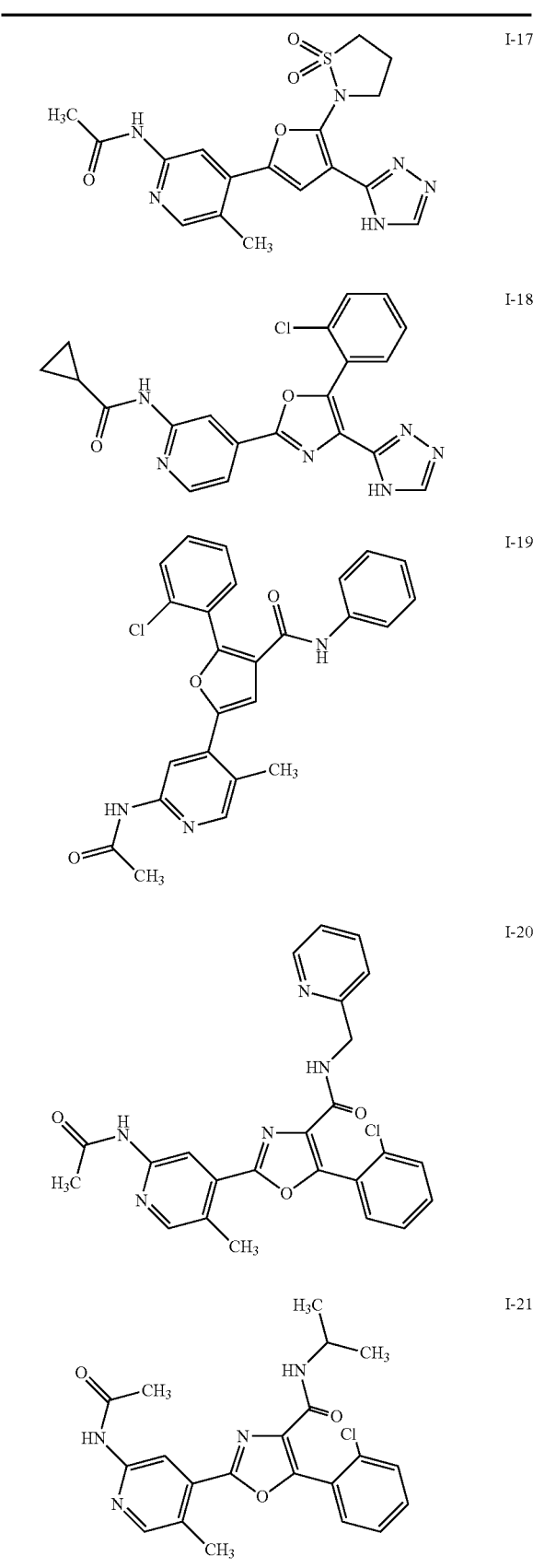
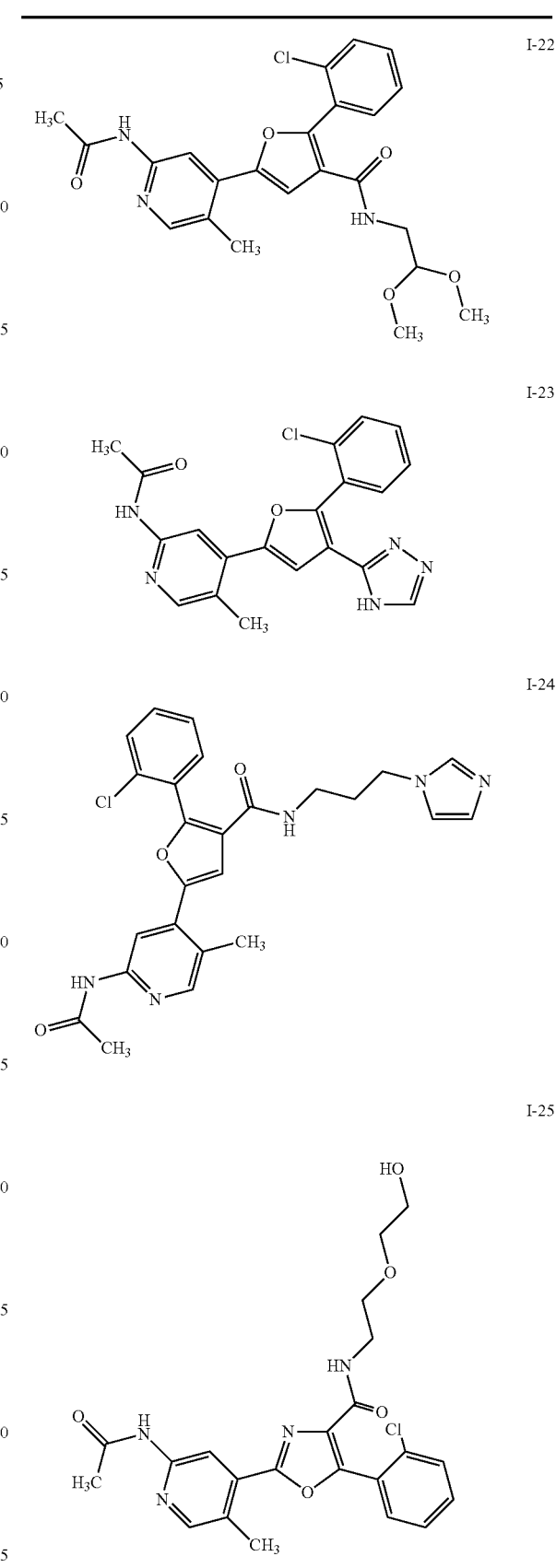

TABLE 1-continued
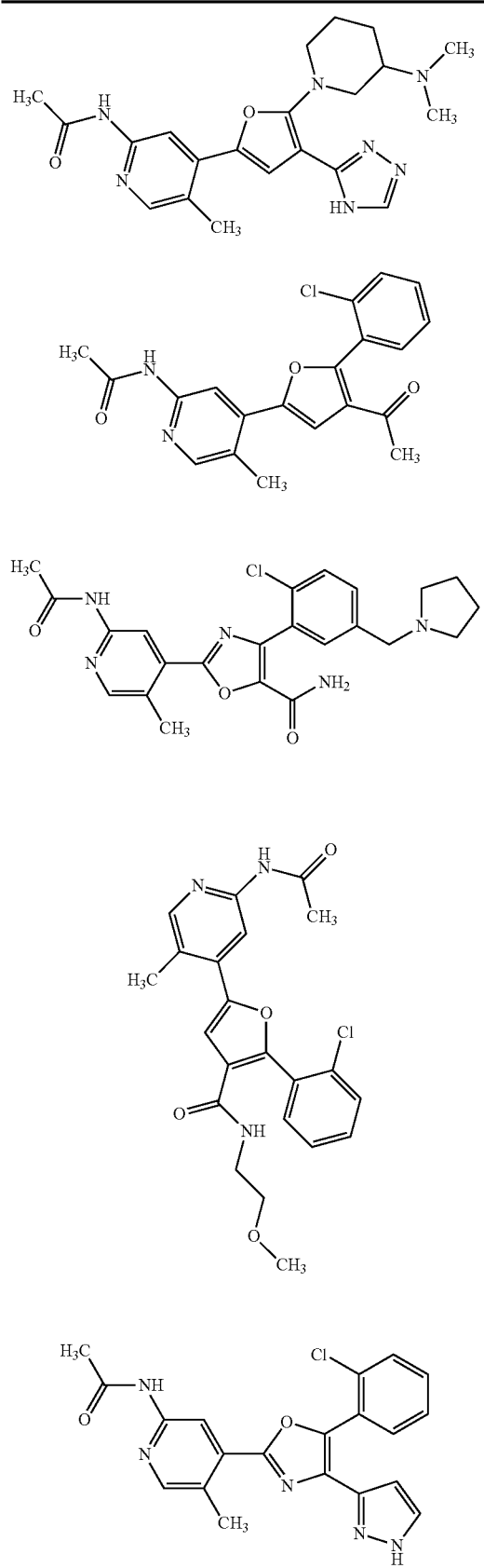
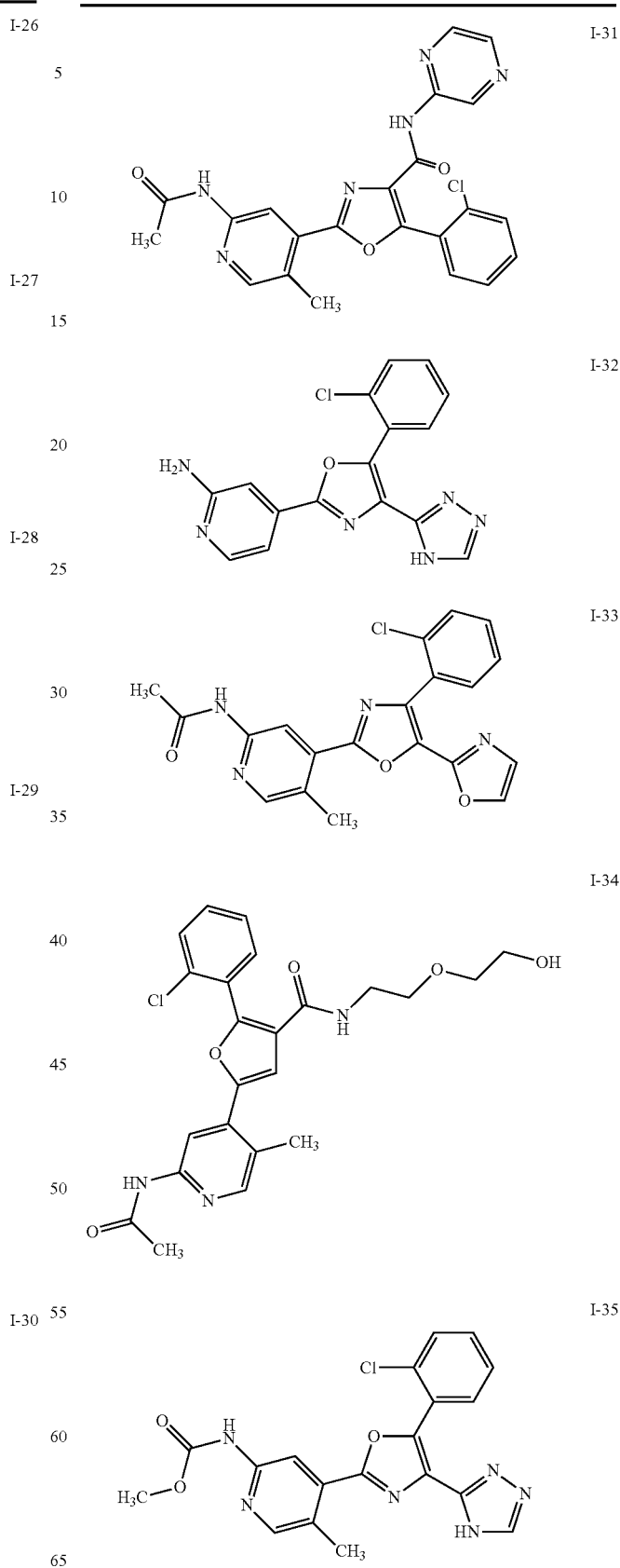

TABLE 1-continued
I-36
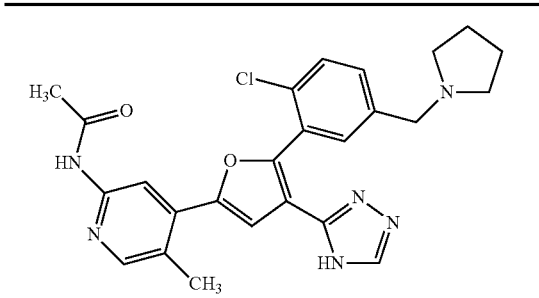
I-37
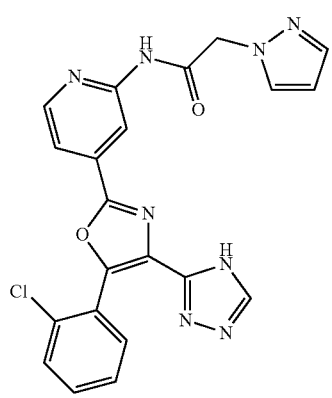 [SMILES: O=C(Cn1cccn1)Nc1cc(-c2nc(-c3nnc[nH]3)c(-c3ccccc3Cl)o2)ccn1]
I-38
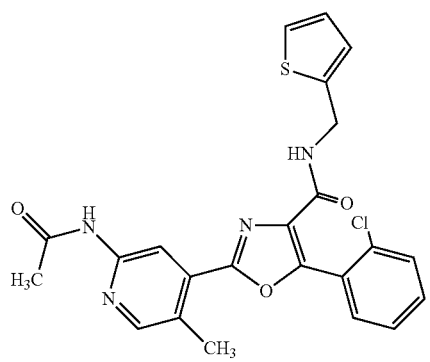 [SMILES: CC(=O)Nc1cc(-c2nc(C(=O)NCc3cccs3)c(-c3ccccc3Cl)o2)c(C)cn1]
I-39
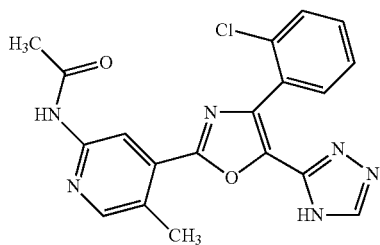 [SMILES: CC(=O)Nc1cc(-c2nc(-c3ccccc3Cl)c(-c3nnc[nH]3)o2)c(C)cn1]
I-40
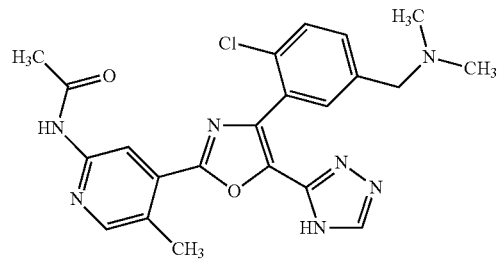 [SMILES: CC(=O)Nc1cc(-c2nc(-c3cc(CN(C)C)ccc3Cl)c(-c3nnc[nH]3)o2)c(C)cn1]
TABLE 1-continued
I-41
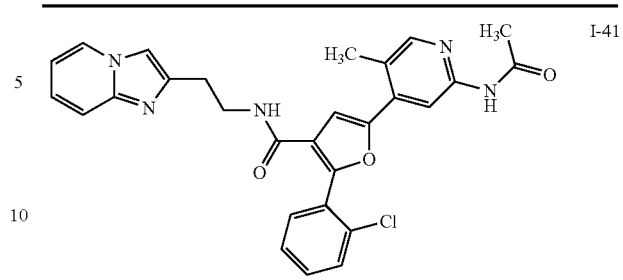
I-42
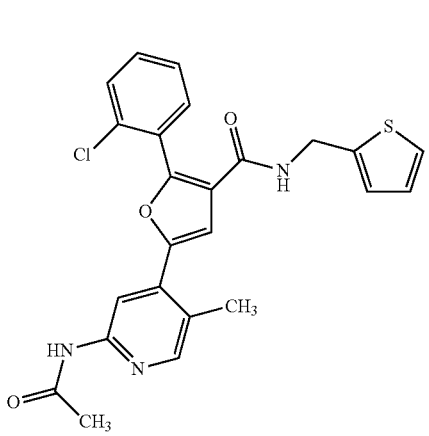 [SMILES: CC(=O)Nc1cc(-c2cc(C(=O)NCc3cccs3)c(-c3ccccc3Cl)o2)c(C)cn1]
I-43
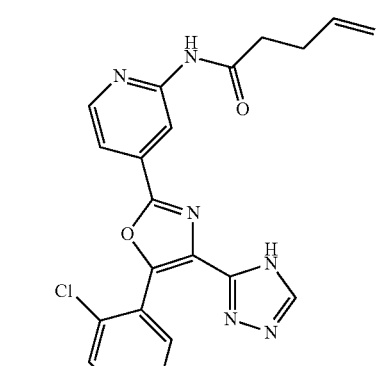
I-44
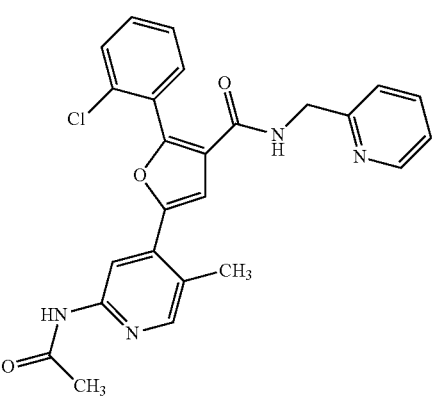 [SMILES: CC(=O)Nc1cc(-c2cc(C(=O)NCc3cccnc3)c(-c3ccccc3Cl)o2)c(C)cn1]

TABLE 1-continued
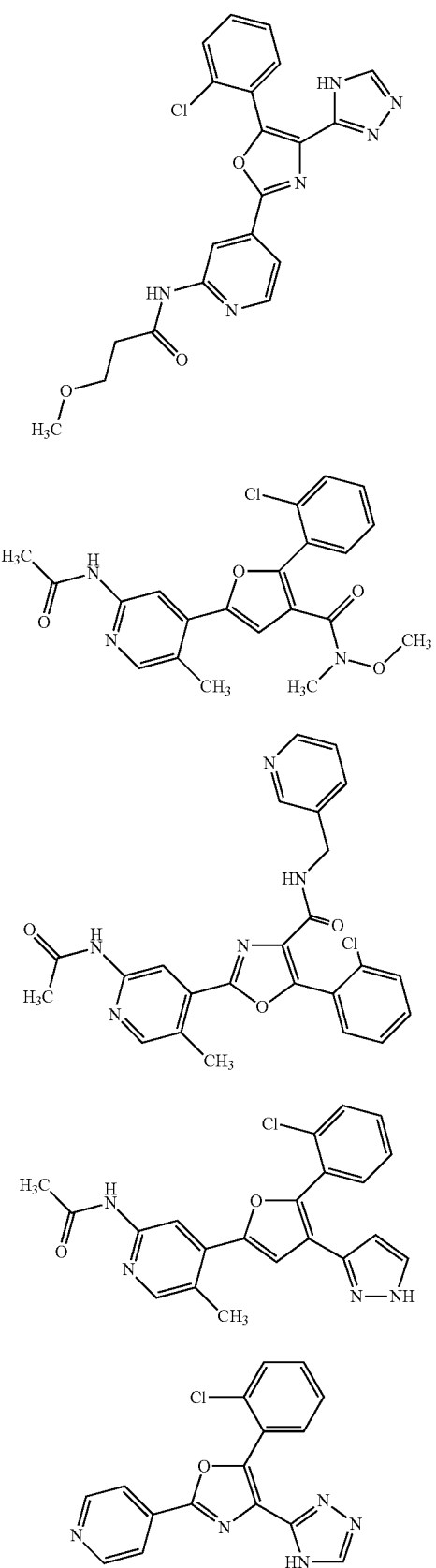
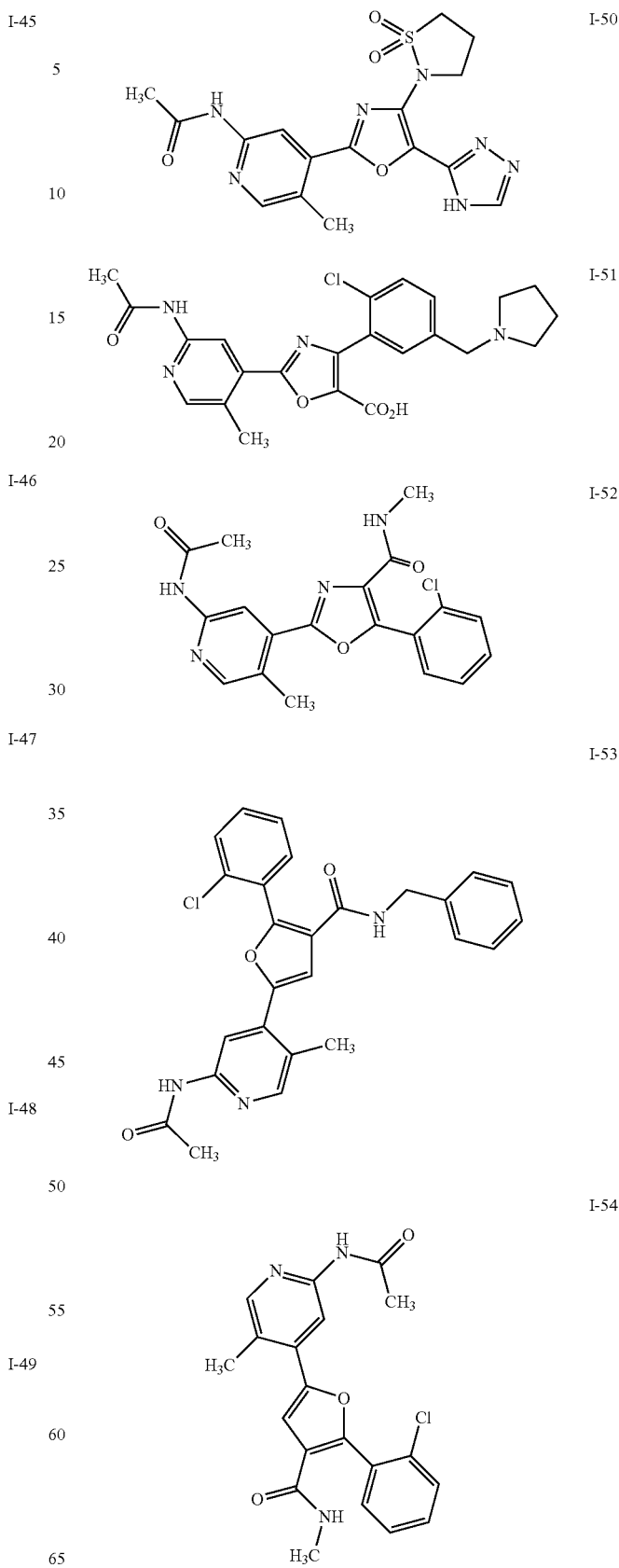

TABLE 1-continued
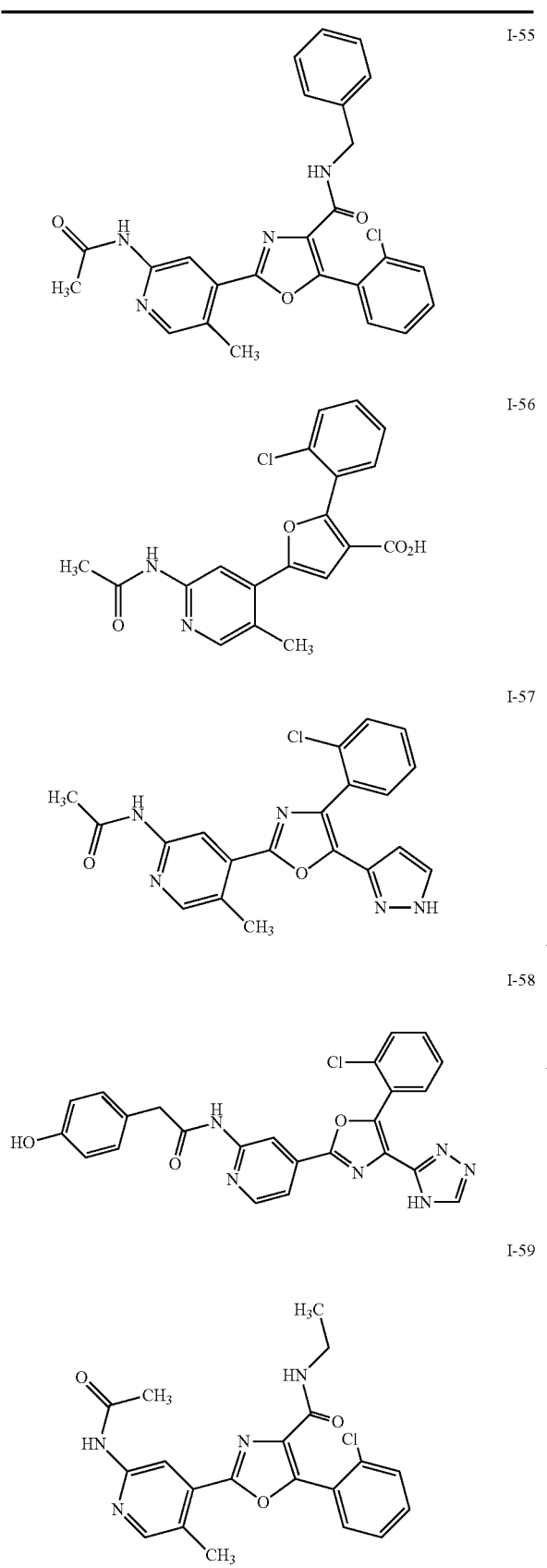
I-55
I-56
I-57
I-58
I-59
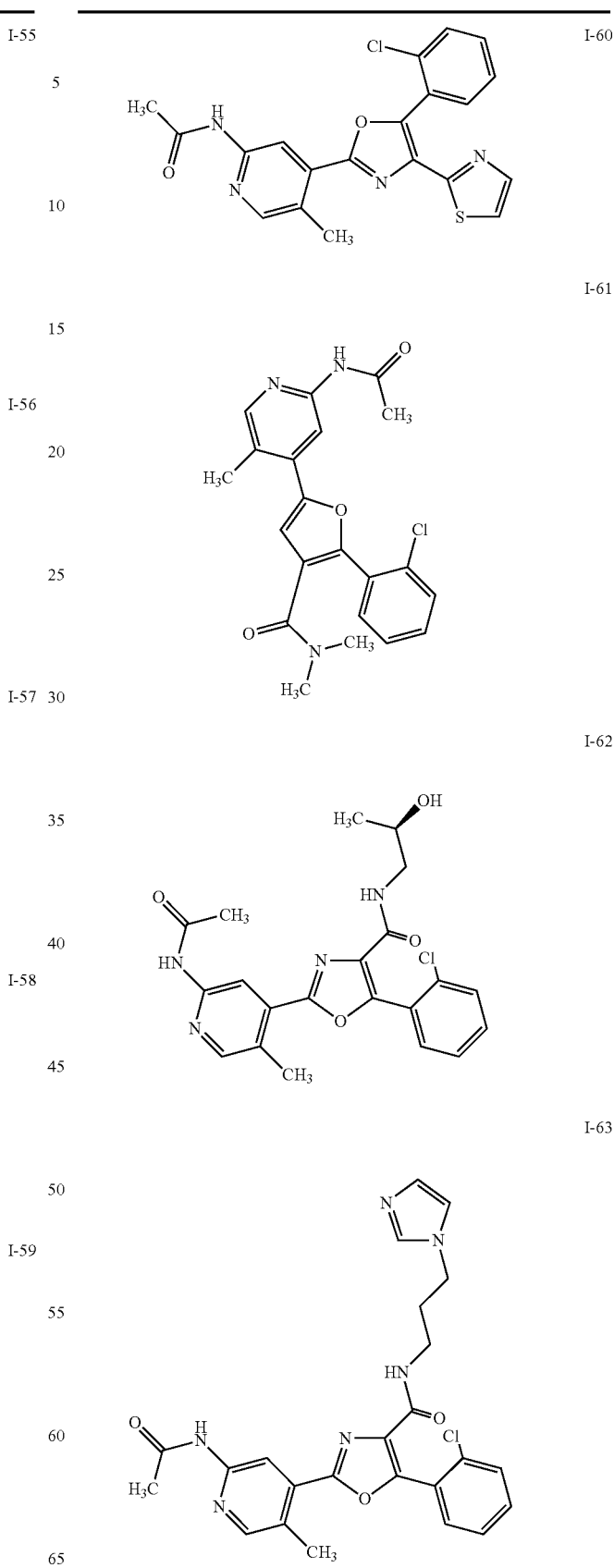
I-60
I-61
I-62
I-63

TABLE 1-continued
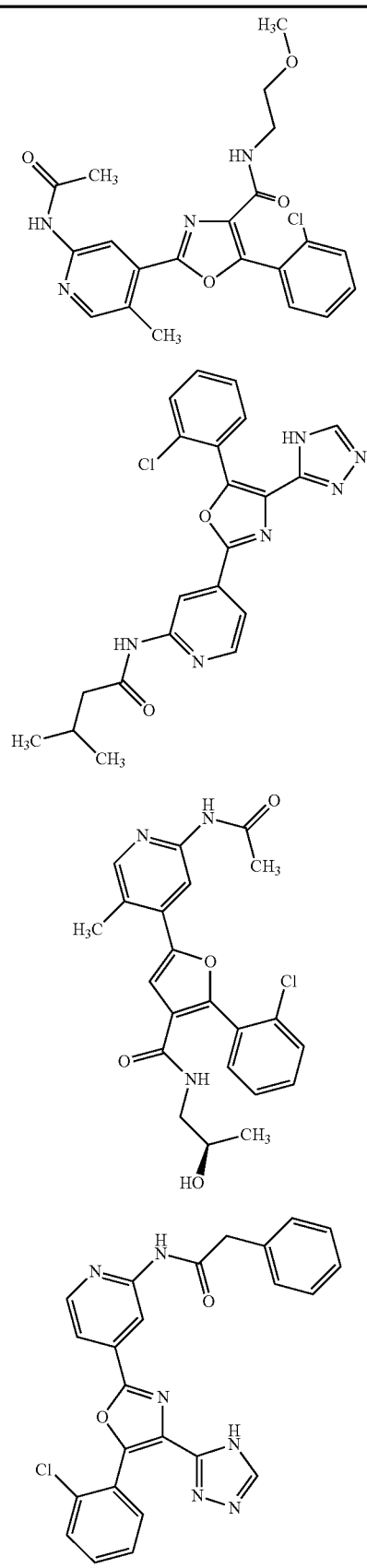
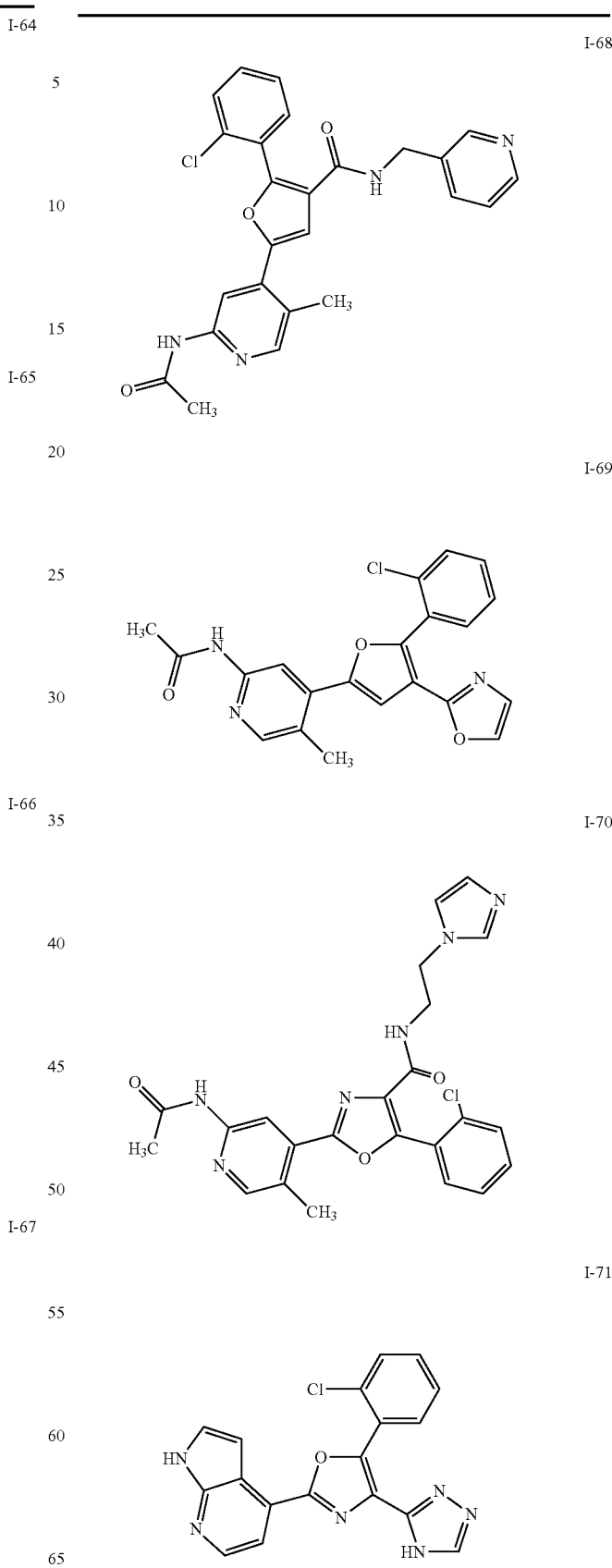

TABLE 1-continued
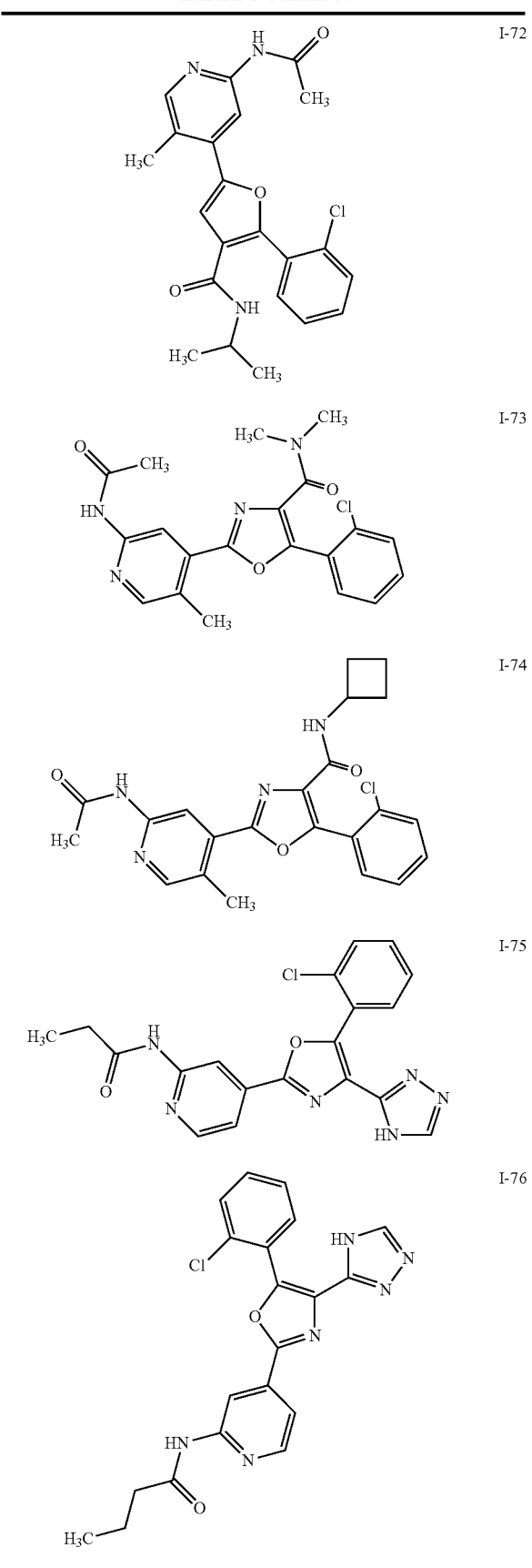
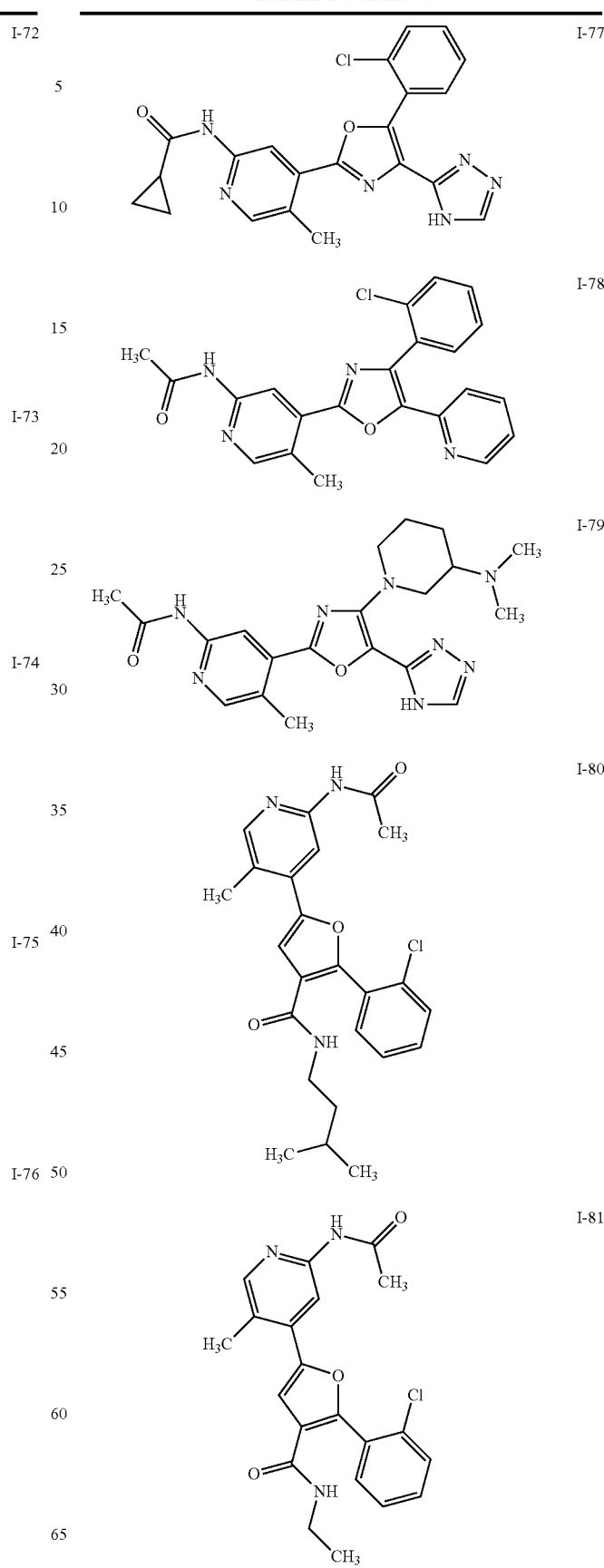

TABLE 1-continued
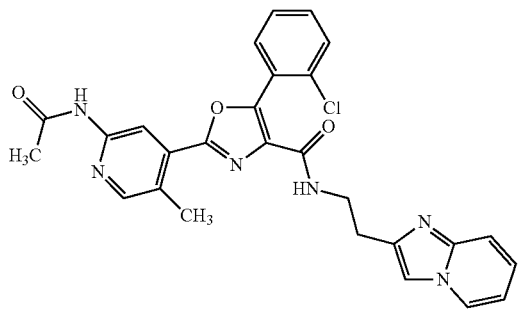 [SMILES: CC(=O)Nc1cc(-c2nc(C(=O)NCCc3cn4ccccc4n3)c(-c3ccccc3Cl)o2)c(C)cn1]
I-82
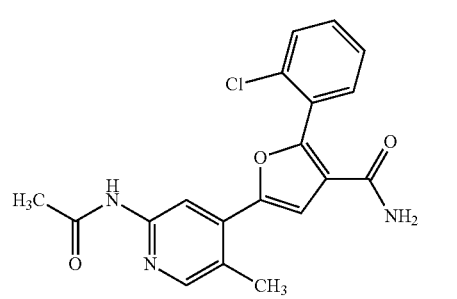 [SMILES: CC(=O)Nc1cc(-c2cc(C(N)=O)c(-c3ccccc3Cl)o2)c(C)cn1]
I-83
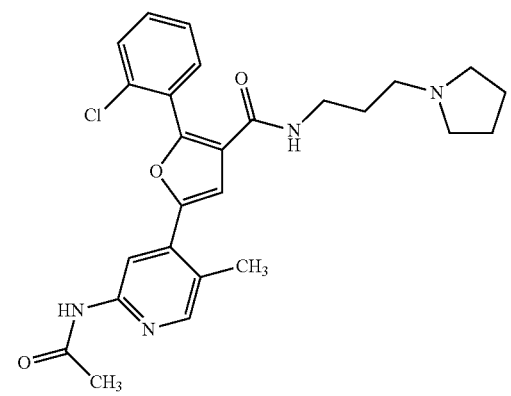 [SMILES: CC(=O)Nc1cc(-c2cc(C(=O)NCCCN3CCCC3)c(-c3ccccc3Cl)o2)c(C)cn1]
I-84
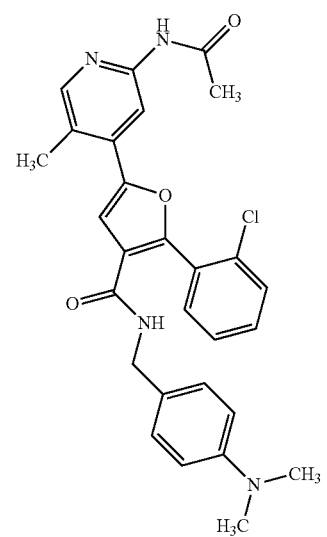
I-85
TABLE 1-continued
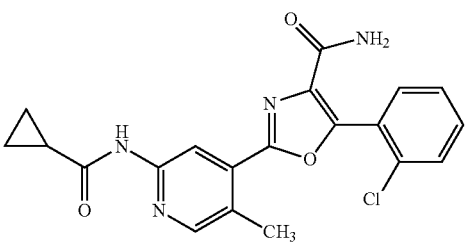 [SMILES: Cc1cnc(NC(=O)C2CC2)cc1-c1nc(C(N)=O)c(-c2ccccc2Cl)o1]
I-86
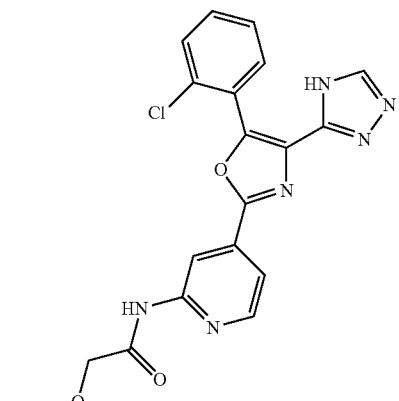
I-87
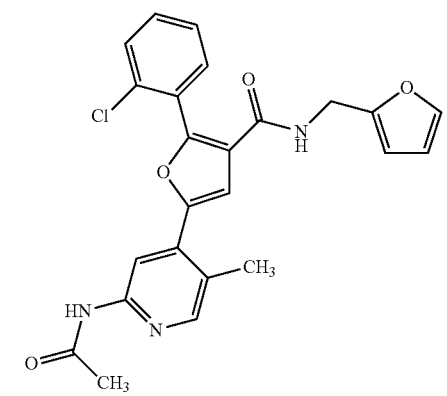
I-88
Table 2 below depicts the IUPAC names of certain compounds represented by compounds of general formula IA and IB.

TABLE 2

| Index | IUPAC name |
|---|---|
| I-1 | 5-[2-(acetylamino)pyridin-4-yl]-2-(2-chlorophenyl)-3-furamide |
| I-2 | 5-[2-(acetylamino)pyridin-4-yl]-2-(2-chlorophenyl)-3-furoic acid |
| I-3 | 2-[2-(acetylamino)-5-methylpyridin-4-yl]-5-(2-chlorophenyl)-1,3-oxazole-4-carboxamide |
| I-4 | N-{4-[5-(2-chlorophenyl)-4-(4H-1,2,4-triazol-3-yl)-1,3-oxazol-2-yl]-5-methylpyridin-2-yl}acetamide |
| I-5 | 2-[2-(acetylamino)-5-methylpyridin-4-yl]-4-(2-chlorophenyl)-1,3-oxazole-5-carboxamide |
| I-6 | 2-[2-(acetylamino)-5-methylpyridin-4-yl]-5-(2-chlorophenyl)-1,3-oxazole-4-carboxylic acid |
| I-7 | N-{4-[5-{2-chloro-5-[(dimethylamino)methyl]phenyl}-4-(4H-1,2,4-triazol-3-yl)-2-furyl]-5-methylpyridin-2-yl}acetamide |
| I-8 | N-{4-[5-(2-chlorophenyl)-4-(4H-1,2,4-triazol-3-yl)-1,3-oxazol-2-yl]phenyl}acetamide |
| I-9 | 2-(2-acetamido-5-methylpyridin-4-yl)-5-(2-chlorophenyl)-N-(2-furylmethyl)-1,3-oxazole-4-carboxamide |
| I-10 | N-{4-[5'-(2-chlorophenyl)-2,4'-bi-1,3-oxazol-2'-yl]-5-methylpyridin-2-yl}acetamide |
| I-11 | 2-(2-acetamido-5-methylpyridin-4-yl)-5-(2-chlorophenyl)-N-(3-methylbutyl)-1,3-oxazole-4-carboxamide |
| I-12 | 5-(2-acetamido-5-methylpyridin-4-yl)-2-(2-chlorophenyl)-N-[2-(1H-imidazol-1-yl)ethyl]-3-furamide |
| I-13 | 2-(2-acetamido-5-methylpyridin-4-yl)-5-(2-chlorophenyl)-N-(4-hydroxybutyl)-1,3-oxazole-4-carboxamide |
| I-14 | 5-(2-acetamido-5-methylpyridin-4-yl)-2-(2-chlorophenyl)-N-cyclobutyl-3-furamide |
| I-15 | 5-(2-acetamido-5-methylpyridin-4-yl)-2-(2-chlorophenyl)-N-(1,3-thiazol-2-yl)-3-furamide |
| I-16 | N-(4-{4-[2-chloro-5-(pyrrolidin-1-ylmethyl)phenyl]-5-(4H-1,2,4-triazol-3-yl)-1,3-oxazol-2-yl}-5-methylpyridin-2-yl)acetamide |
| I-17 | N-{4-[5-(1,1-dioxidoisothiazolidin-2-yl)-4-(4H-1,2,4-triazol-3-yl)-2-furyl]-5-methylpyridin-2-yl}acetamide |
| I-18 | N-{4-[5-(2-chlorophenyl)-4-(4H-1,2,4-triazol-3-yl)-1,3-oxazol-2-yl]pyridin-2-yl}cyclopropanecarboxamide |
| I-19 | 5-(2-acetamido-5-methylpyridin-4-yl)-2-(2-chlorophenyl)-N-phenyl-3-furamide |
| I-20 | 2-(2-acetamido-5-methylpyridin-4-yl)-5-(2-chlorophenyl)-N-(pyridin-2-ylmethyl)-1,3-oxazole-4-carboxamide |
| I-21 | 2-(2-acetamido-5-methylpyridin-4-yl)-5-(2-chlorophenyl)-N-isopropyl-1,3-oxazole-4-carboxamide |
| I-22 | 5-(2-acetamido-5-methylpyridin-4-yl)-2-(2-chlorophenyl)-N-(2,2-dimethoxyethyl)-3-furamide |
| I-23 | N-{4-[5-(2-chlorophenyl)-4-(4H-1,2,4-triazol-3-yl)-2-furyl]-5-methylpyridin-2-yl}acetamide |
| I-24 | 5-(2-acetamido-5-methylpyridin-4-yl)-2-(2-chlorophenyl)-N-[3-(1H-imidazol-1-yl)propyl]-3-furamide |
| I-25 | 2-(2-acetamido-5-methylpyridin-4-yl)-5-(2-chlorophenyl)-N-[2-(2-hydroxyethoxy)ethyl]-1,3-oxazole-4-carboxamide |
| I-26 | N-(4-{5-[3-(dimethylamino)piperidin-1-yl]-4-(4H-1,2,4-triazol-3-yl)-2-furyl}-5-methylpyridin-2-yl)acetamide |
| I-27 | N-{4-[4-acetyl-5-(2-chlorophenyl)-2-furyl]-5-methylpyridin-2-yl}acetamide |
| I-28 | 2-(2-acetamido-5-methylpyridin-4-yl)-4-[2-chloro-5-(pyrrolidin-1-ylmethyl)phenyl]-1,3-oxazole-5-carboxamide |
| I-29 | 5-(2-acetamido-5-methylpyridin-4-yl)-2-(2-chlorophenyl)-N-(2-methoxyethyl)-3-furamide |
| I-30 | N-{4-[5-(2-chlorophenyl)-4-(1H-pyrazol-3-yl)-1,3-oxazol-2-yl]-5-methylpyridin-2-yl}acetamide |
| I-31 | 2-(2-acetamido-5-methylpyridin-4-yl)-5-(2-chlorophenyl)-N-(pyrazin-2-yl)-1,3-oxazole-4-carboxamide |
| I-32 | 4-[5-(2-chlorophenyl)-4-(4H-1,2,4-triazol-3-yl)-1,3-oxazol-2-yl]pyridin-2-amine |
| I-33 | N-{4-[4'-(2-chlorophenyl)-2,5'-bi-1,3-oxazol-2'-yl]-5-methylpyridin-2-yl}acetamide |
| I-34 | 5-(2-acetamido-5-methylpyridin-4-yl)-2-(2-chlorophenyl)-N-[2-(2-hydroxyethoxy)ethyl]-3-furamide |
| I-35 | methyl {4-[5-(2-chlorophenyl)-4-(4H-1,2,4-triazol-3-yl)-1,3-oxazol-2-yl]-5-methylpyridin-2-yl}carbamate |
| I-36 | N-(4-{5-[2-chloro-5-(pyrrolidin-1-ylmethyl)phenyl]-4-(4H-1,2,4-triazol-3-yl)-2-furyl}-5-methylpyridin-2-yl)acetamide |
| I-37 | N-{4-[5-(2-chlorophenyl)-4-(4H-1,2,4-triazol-3-yl)-1,3-oxazol-2-yl]pyridin-2-yl}-2-(1H-pyrazol-1-yl)acetamide |
| I-38 | 2-(2-acetamido-5-methylpyridin-4-yl)-5-(2-chlorophenyl)-N-(2-thienylmethyl)-1,3-oxazole-4-carboxamide |
| I-39 | N-{4-[4-(2-chlorophenyl)-5-(4H-1,2,4-triazol-3-yl)-1,3-oxazol-2-yl]-5-methylpyridin-2-yl}acetamide |
| I-40 | N-{4-{4-{2-chloro-5-[(dimethylamino)methyl]phenyl}-5-(4H-1,2,4-triazol-3-yl)-1,3-oxazol-2-yl]-5-methylpyridin-2-yl}acetamide |
| I-41 | 5-(2-acetamido-5-methylpyridin-4-yl)-2-(2-chlorophenyl)-N-[2-(imidazo[1,2-a]pyridin-2-yl)ethyl]-3-furamide |
| I-42 | 5-(2-acetamido-5-methylpyridin-4-yl)-2-(2-chlorophenyl)-N-(2-thienylmethyl)-3-furamide |
| I-43 | N-{4-[5-(2-chlorophenyl)-4-(4H-1,2,4-triazol-3-yl)-1,3-oxazol-2-yl]pyridin-2-yl}pent-4-enamide |

TABLE 2-continued

| Index | IUPAC name |
|---|---|
| I-44 | 5-(2-acetamido-5-methylpyridin-4-yl)-2-(2-chlorophenyl)-N-(pyridin-2-ylmethyl)-3-furamide |
| I-45 | N-{4-[5-(2-chlorophenyl)-4-(4H-1,2,4-triazol-3-yl)-1,3-oxazol-2-yl]pyridin-2-yl}-3-methoxypropanamide |
| I-46 | 5-(2-acetamido-5-methylpyridin-4-yl)-2-(2-chlorophenyl)-N-methoxy-N-methyl-3-furamide |
| I-47 | 2-(2-acetamido-5-methylpyridin-4-yl)-5-(2-chlorophenyl)-N-(pyridin-3-ylmethyl)-1,3-oxazole-4-carboxamide |
| I-48 | N-{4-[5-(2-chlorophenyl)-4-(1H-pyrazol-3-yl)-2-furyl]-5-methylpyridin-2-yl}acetamide |
| I-49 | 4-[5-(2-chlorophenyl)-4-(4H-1,2,4-triazol-3-yl)-1,3-oxazol-2-yl]pyridine |
| I-50 | N-{4-[4-(1,1-dioxidoisothiazolidin-2-yl)-5-(4H-1,2,4-triazol-3-yl)-1,3-oxazol-2-yl]-5-methylpyridin-2-yl}acetamide |
| I-51 | 2-(2-acetamido-5-methylpyridin-4-yl)-4-[2-chloro-5-(pyrrolidin-1-ylmethyl)phenyl]-1,3-oxazole-5-carboxylic acid |
| I-52 | 2-(2-acetamido-5-methylpyridin-4-yl)-5-(2-chlorophenyl)-N-methyl-1,3-oxazole-4-carboxamide |
| I-53 | 5-(2-acetamido-5-methylpyridin-4-yl)-N-benzyl-2-(2-chlorophenyl)-3-furamide |
| I-54 | 5-(2-acetamido-5-methylpyridin-4-yl)-2-(2-chlorophenyl)-N-methyl-3-furamide |
| I-55 | 2-(2-acetamido-5-methylpyridin-4-yl)-N-benzyl-5-(2-chlorophenyl)-1,3-oxazole-4-carboxamide |
| I-56 | 5-(2-acetamido-5-methylpyridin-4-yl)-2-(2-chlorophenyl)-3-furoic acid |
| I-57 | N-{4-[4-(2-chlorophenyl)-5-(1H-pyrazol-3-yl)-1,3-oxazol-2-yl]-5-methylpyridin-2-yl}acetamide |
| I-58 | N-{4-[5-(2-chlorophenyl)-4-(4H-1,2,4-triazol-3-yl)-1,3-oxazol-2-yl]pyridin-2-yl}-2-(4-hydroxyphenyl)acetamide |
| I-59 | 2-(2-acetamido-5-methylpyridin-4-yl)-5-(2-chlorophenyl)-N-ethyl-1,3-oxazole-4-carboxamide |
| I-60 | N-{4-[5-(2-chlorophenyl)-4-(1,3-thiazol-2-yl)-1,3-oxazol-2-yl]-5-methylpyridin-2-yl}acetamide |
| I-61 | 5-(2-acetamido-5-methylpyridin-4-yl)-2-(2-chlorophenyl)-N,N-dimethyl-3-furamide |
| I-62 | 2-(2-acetamido-5-methylpyridin-4-yl)-5-(2-chlorophenyl)-N-(2-hydroxypropyl)-1,3-oxazole-4-carboxamide |
| I-63 | 2-(2-acetamido-5-methylpyridin-4-yl)-5-(2-chlorophenyl)-N-[3-(1H-imidazol-1-yl)propyl]-1,3-oxazole-4-carboxamide |
| I-64 | 2-(2-acetamido-5-methylpyridin-4-yl)-5-(2-chlorophenyl)-N-(2-methoxyethyl)-1,3-oxazole-4-carboxamide |
| I-65 | N-{4-[5-(2-chlorophenyl)-4-(4H-1,2,4-triazol-3-yl)-1,3-oxazol-2-yl]pyridin-2-yl}-3-methylbutanamide |
| I-66 | 5-(2-acetamido-5-methylpyridin-4-yl)-2-(2-chlorophenyl)-N-(2-hydroxypropyl)-3-furamide |
| I-67 | N-{4-[5-(2-chlorophenyl)-4-(4H-1,2,4-triazol-3-yl)-1,3-oxazol-2-yl]pyridin-2-yl}-2-phenylacetamide |
| I-68 | 5-(2-acetamido-5-methylpyridin-4-yl)-2-(2-chlorophenyl)-N-(pyridin-3-ylmethyl)-3-furamide |
| I-69 | N-{4-[5-(2-chlorophenyl)-4-(1,3-oxazol-2-yl)-2-furyl]-5-methylpyridin-2-yl}acetamide |
| I-70 | 2-(2-acetamido-5-methylpyridin-4-yl)-5-(2-chlorophenyl)-N-[2-(1H-imidazol-1-yl)ethyl]-1,3-oxazole-4-carboxamide |
| I-71 | 4-[5-(2-chlorophenyl)-4-(4H-1,2,4-triazol-3-yl)-1,3-oxazol-2-yl]-1H-pyrrolo[2,3-b]pyridine |
| I-72 | 5-(2-acetamido-5-methylpyridin-4-yl)-2-(2-chlorophenyl)-N-isopropyl-3-furamide |
| I-73 | 2-(2-acetamido-5-methylpyridin-4-yl)-5-(2-chlorophenyl)-N,N-dimethyl-1,3-oxazole-4-carboxamide |
| I-74 | 2-(2-acetamido-5-methylpyridin-4-yl)-5-(2-chlorophenyl)-N-cyclobutyl-1,3-oxazole-4-carboxamide |
| I-75 | N-{4-[5-(2-chlorophenyl)-4-(4H-1,2,4-triazol-3-yl)-1,3-oxazol-2-yl]pyridin-2-yl}propanamide |
| I-76 | N-{4-[5-(2-chlorophenyl)-4-(4H-1,2,4-triazol-3-yl)-1,3-oxazol-2-yl]pyridin-2-yl}butanamide |
| I-77 | N-{4-[5-(2-chlorophenyl)-4-(4H-1,2,4-triazol-3-yl)-1,3-oxazol-2-yl]-5-methylpyridin-2-yl}cyclopropanecarboxamide |
| I-78 | N-{4-[4-(2-chlorophenyl)-5-(pyridin-2-yl)-1,3-oxazol-2-yl]-5-methylpyridin-2-yl}acetamide |
| I-79 | N-(4-{4-[3-(dimethylamino)piperidin-1-yl]-5-(4H-1,2,4-triazol-3-yl)-1,3-oxazol-2-yl}-5-methylpyridin-2-yl)acetamide |
| I-80 | 5-(2-acetamido-5-methylpyridin-4-yl)-2-(2-chlorophenyl)-N-(3-methylbutyl)-3-furamide |
| I-81 | 5-(2-acetamido-5-methylpyridin-4-yl)-2-(2-chlorophenyl)-N-ethyl-3-furamide |
| I-82 | 2-(2-acetamido-5-methylpyridin-4-yl)-5-(2-chlorophenyl)-N-[2-(imidazo[1,2-a]pyridin-2-yl)ethyl]-1,3-oxazole-4-carboxamide |
| I-83 | 5-(2-acetamido-5-methylpyridin-4-yl)-2-(2-chlorophenyl)-3-furamide |
| I-84 | 5-(2-acetamido-5-methylpyridin-4-yl)-2-(2-chlorophenyl)-N-[3-(pyrrolidin-1-yl)propyl]-3-furamide |
| I-85 | 5-(2-acetamido-5-methylpyridin-4-yl)-2-(2-chlorophenyl)-N-[4-(dimethylamino)benzyl]-3-furamide |
| I-86 | 5-(2-chlorophenyl)-2-{2-[(cyclopropylcarbonyl)amino]-5-methylpyridin-4-yl}-1,3-oxazole-4-carboxamide |

TABLE 2-continued

| Index | IUPAC name |
|---|---|
| I-87 | N-{4-[5-(2-chlorophenyl)-4-(4H-1,2,4-triazol-3-yl)-1,3-oxazol-2-yl]pyridin-2-yl}-2-methoxyacetamide |
| I-88 | 5-(2-acetamido-5-methylpyridin-4-yl)-2-(2-chlorophenyl)-N-(2-furylmethyl)-3-furamide |

| Definitions | |
|---|---|
| ACN | acetonitrile |
| AcOH | acetic acid |
| C. | celsius |
| CDI | 1,1'-carbonyldiimidazole |
| Dba | dibenzylideneacetone |
| DCM | dichloromethane |
| DIEA | diisopropylethylamine |
| DMAP | 4-dimethylaminopyridine |
| DMF | dimethylformamide |
| DMF-DMA | dimethylformamide dimethylacetal |
| DMPU | 1,3-dimethyltetrahydropyrimidin-2(1H)-one |
| DMSO | dimethylsulfoxide |
| dppf | 1,1'-bis(diphenylphosphino) ferrocene |
| EDCI | 1-ethyl-3-(3-dimethylaminopropyl) carbodiimide |
| EtOAc | ethyl acetate |
| HATU | N,N,N',N'-tetramethyl-O-(7-azabenzotriazol-1-yl) uronium hexafluorophosphate |
| HMDS | hexamethyldisilazane |
| HOBt | hydroxybenzotriazole |
| h | hours |
| $IC_{50}$ | inhibitory concentration 50% |
| LCMS | liquid chromatography mass spectrometry |
| LDA | lithium diisopropylamide |
| m/z | mass to charge |
| MeOH | methanol |
| min | minutes |
| MS | mass spectrum |
| psi | pounds per square inch |
| rt | room temperature |
| SEM | 2-(trimethylsilyl)ethoxy methyl |
| STAB | sodium triacetoxyborohydride |
| TBAF | tetra-n-butylammonium fluoride |
| TEA | triethylamine |
| TFA | trifluoroacetic acid |
| THF | tetrahydrofuran |
| TBTU | O-(benzotriazol-1-yl)-N,N,N',N',-tetramethyluronium tetrafluoroborate |
| Xantphos | 4,5-bis(diphenylphosphino)-9,9-dimethylxanthene |

AcOH acetic acid
C celsius
CDI 1,1'-carbonyldiimidazole
Dba dibenzylideneacetone
DCM dichloromethane
DIEA diisopropylethylamine
DMAP 4-dimethylaminopyridine
DMF dimethylformamide
DMF-DMA dimethylformamide dimethylacetal
DMPU 1,3-dimethyltetrahydropyrimidin-2(1H)-one
DMSO dimethylsulfoxide
dppf 1,1'-bis(diphenylphosphino)ferrocene
EDCI 1-ethyl-3-(3-dimethylaminopropyl) carbodiimide
EtOAc ethyl acetate
HATU N,N,N',N'-tetramethyl-O-(7-azabenzotriazol-1-yl) uronium hexafluorophosphate
HMDS hexamethyldisilazane
HOBt hydroxybenzotriazole
h hours
$IC_{50}$ inhibitory concentration 50%
LCMS liquid chromatography mass spectrometry
LDA lithium diisopropylamide
m/z mass to charge
MeOH methanol
min minutes
MS mass spectrum
psi pounds per square inch
rt room temperature
SEM 2-(trimethylsilyl)ethoxy methyl
STAB sodium triacetoxyborohydride
TBAF tetra-n-butylammonium fluoride
TEA triethylamine
TFA trifluoroacetic acid
THF tetrahydrofuran
TBTU O-(benzotriazol-1-yl)-N,N,N',N'-tetramethyluronium tetrafluoroborate
Xantphos 4,5-bis(diphenylphosphino)-9,9-dimethylxan-thene Analytical LC-MS Methods LCMS spectra were recorded on a Hewlett-Packard HP1100 or Agilent 1100 Series LC system connected to a Micromass mass spectrometer using reverse phase C18 columns. Various gradients and run times were selected in order to best characterize the compounds. Mobile phases were based on ACN/water gradients and contained either 0.1% formic acid (methods indicated FA) or 10 mM ammonium acetate (methods indicated AA). One example of a solvent gradient that was used was 100% mobile phase A (mobile phase A=99% water+1% ACN+0.1% formic acid) to 100% mobile phase B (mobile phase B=95% ACN+5% water+0.1% formic acid) at a flow rate of 1 mL/min for a 16.5 min run.

One of ordinary skill in the art will recognize that modifications of the gradient, column length, and flow rate are possible and that some conditions may be more suitable for compound characterization than others, depending on the chemical species being analyzed.

Example 1

Synthesis of Intermediate Stannanes and Boronic Esters

N-[4-(4,4,5,5-tetramethyl-1,3,2-dioxaborolan-2-yl)pyridin-2-yl]acetamide

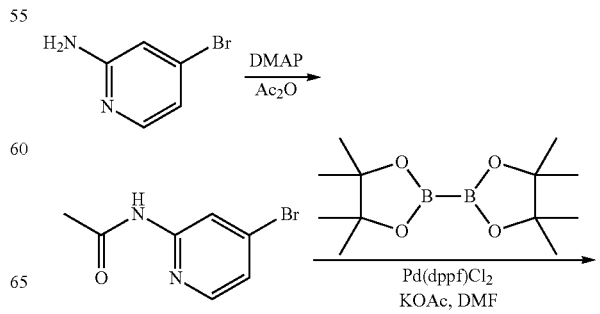

-continued

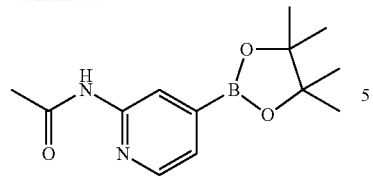

Step 1: N-(4-bromopyridin-2-yl)acetamide

To a solution of 4-bromopyridin-2-amine (12.0 g, 69.4 mmol) in acetic anhydride (240 mL) was added DMAP (0.0847 g, 0.694 mmol). The reaction mixture was allowed to stir at 140° C. for 3 h and then allowed to cool to rt. Ice water was added and the pH of the mixture was adjusted to 8.5 by the addition of concentrated NH$_4$OH. The solid which precipitated was filtered, washed with cold water and hexanes, and dried to give N-(4-bromopyridin-2-yl)acetamide (13.3 g) as a white solid.

Step 2: N-[4-(4,4,5,5-tetramethyl-1,3,2-dioxaborolan-2-yl)pyridin-2-yl]acetamide To a mixture of N-(4-bromopyridin-2-yl)acetamide (17.2 g, 80 mmol), 4,4,4',4',5,5,5',5'-octamethyl-2,2'-bi-1,3,2-dioxaborolane (26.4 g, 104 mmol), Pd(dppf)Cl$_2$ (11.7 g, 16 mmol) and KOAc (23.6 g, 240 mmol) under an atmosphere of nitrogen was added anhydrous DMF (1500 mL). The mixture was allowed to stir at 80° C. for 3.5 h. The solvent was removed and the residue was diluted with EtOAc (1000 mL). Activated carbon (100 g) was added. The slurry was heated at reflux for 5 min and then filtered. The organic solution was concentrated and the residue was recrystallized from EtOAc to give N-[4-(4,4,5,5-tetramethyl-1,3,2-dioxaborolan-2-yl)pyridin-2-yl]acetamide (6.1 g, 29%) as a white solid. $^1$H NMR (400 MHz, DMSO-d$_6$): δ 10.47 (br s, 1H), 8.30-8.33 (m, 2H), 7.24 (dd, J=6.0, 1.2 Hz, 1H), 2.09 (s, 3H) and 1.29 (s, 12H).

N-[5-methyl-4-(trimethylstannyl)pyridin-2-yl]acetamide

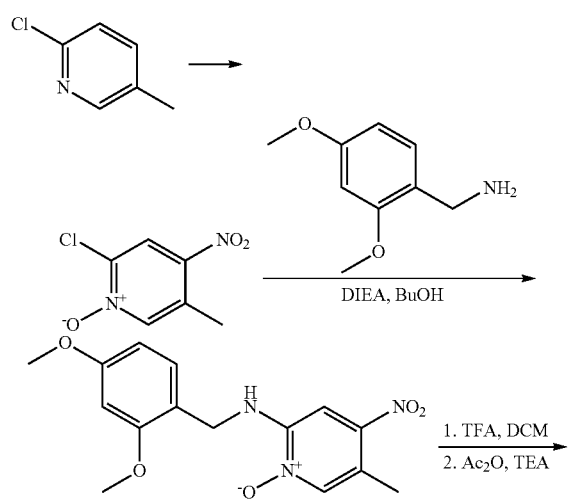

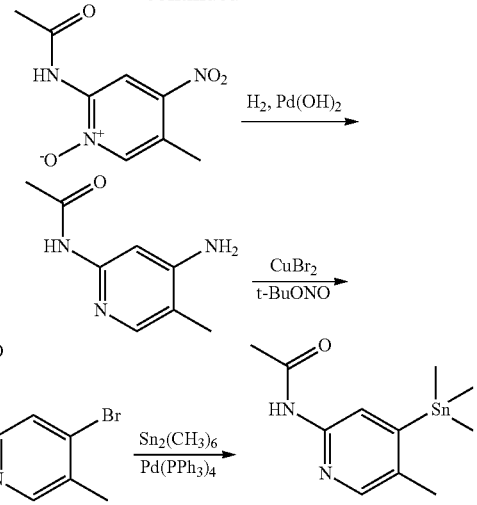

Step 1: 2-chloro-5-methyl-4-nitropyridine 1-oxide

Hydrogen peroxide (17 mL) was added via addition funnel over 10 minutes to a solution of 2-chloro-5-methylpyridine (5.5 mL, 50 mmol) in acetic anhydride (17 mL). The reaction mixture was allowed to stir at rt overnight and then to stir at 60° C. for 30 h. Excess AcOH was removed by evaporation and then the residue was added in small portions to concentrated sulfuric acid (10.3 mL). The resulting solution was added to a mixture of concentrated sulfuric acid (10.3 mL) and fuming nitric acid (17.2 mL) and allowed to stir at 100° C. After 1.5 h, the reaction mixture was poured onto ice. The solution was basified by the addition of solid ammonium carbonate until gas evolution ceased and a precipitate formed. The mixture was further basified with concentrated NH$_4$OH to a final pH of 11. After stirring for 1 h at rt, the mixture was filtered and 2-chloro-5-methyl-4-nitropyridine 1-oxide (6.25 g, 66%) was isolated as a yellow solid. LCMS (FA): m/z=189 (M+H).

Step 2: N-(2,4-dimethoxybenzyl)-5-methyl-4-nitropyridin-2-amine 1-oxide

A mixture of 2-chloro-5-methyl-4-nitropyridine 1-oxide (1.1 g, 5.8 mmol), 1-(2,4-dimethoxyphenyl)methanamine (1.1 mL, 7.0 mmol), DIEA (2.0 mL, 11.6 mmol), and 1-butanol (9 mL) was subjected to microwave irradiation at 120° C. for 8 h. The reaction mixture was allowed to cool to rt and was filtered. The resulting solid was washed with water (20 mL) and dried to give N-(2,4-dimethoxybenzyl)-5-methyl-4-nitropyridin-2-amine 1-oxide (1.2 g, 67%), which was used in the next step without further purification.

Step 3: N-(5-methyl-4-nitro-1-oxidopyridin-2-yl)acetamide

A solution of N-(2,4-dimethoxybenzyl)-5-methyl-4-nitropyridin-2-amine 1-oxide (1.1 g, 3.5 mmol) in DCM (20 mL) and TFA (3 mL) was allowed to stir at rt for 4 h. The reaction mixture was concentrated and the residue was dissolved in DCM (20 mL). To this solution were added TEA (2.5 mL, 17.7 mmol) and acetic anhydride (0.4 g, 4.3 mmol). The reaction mixture was allowed to stir at rt overnight and then filtered to give N-(5-methyl-4-nitro-1-oxidopyridin-2-yl)acetamide (0.73 g, 98%) which was used without further purification.

Step 4: N-(4-amino-5-methylpyridin-2-yl)acetamide

A mixture of N-(5-methyl-4-nitro-1-oxidopyridin-2-yl)acetamide (3.1 g, 14.7 mmol) and Pd(OH)$_2$ (20% on carbon, 1.6 g) in MeOH (80 mL) was allowed to stir under 40 psi of hydrogen at rt for 6 days. The reaction mixture was then filtered over celite and the filter cake was washed with DCM. The filtrate was concentrated to give N-(4-amino-5-methylpyridin-2-yl)acetamide (2.1 g, 86%) which was used without further purification.

Step 5: N-(4-bromo-5-methylpyridin-2-yl)acetamide

Copper(II) bromide (8.8 g, 39.5 mmol) was dissolved in acetonitrile (85 mL). To this solution was added tert-butyl nitrite (4.1 mL, 34.2 mmol). The mixture was allowed to stir at 65° C. for 15 min, and then N-(4-amino-5-methylpyridin-2-yl)acetamide (4.4 g, 26.3 mmol) in acetonitrile (40 mL) was added. The reaction mixture was allowed to continue to stir at 65° C. for 35 min. The reaction mixture was concentrated and 15% aqueous NH$_4$OH was added to the residue. The solution was extracted with EtOAc. The organic solutions were combined and concentrated. The residue was purified by column chromatography to give N-(4-bromo-5-methylpyridin-2-yl)acetamide (2.56 g, 42%).

Step 6: N-[5-methyl-4-(trimethylstannyl)pyridin-2-yl]acetamide

A mixture of N-(4-bromo-5-methylpyridin-2-yl)acetamide (2.56 g, 11.2 mmol), hexamethylditin (3.0 mL, 14.5 mmol) and tetrakis(triphenylphosphine) palladium(0) (0.65 g, 0.56 mmol) in 1,4-dioxane (42 mL) was allowed to stir at 95° C. for 4 h. The reaction mixture was allowed to cool to rt and then filtered through celite. The filtrate was concentrated and the residue was purified by column chromatography to give N-[5-methyl-4-(trimethylstannyl)pyridin-2-yl]acetamide (3.0 g, 86%). LCMS (FA): m/z=315.2 (M+H).

N-[5-methyl-4-(4,4,5,5-tetramethyl-1,3,2-dioxaborolan-2-yl)pyridin-2-yl]acetamide

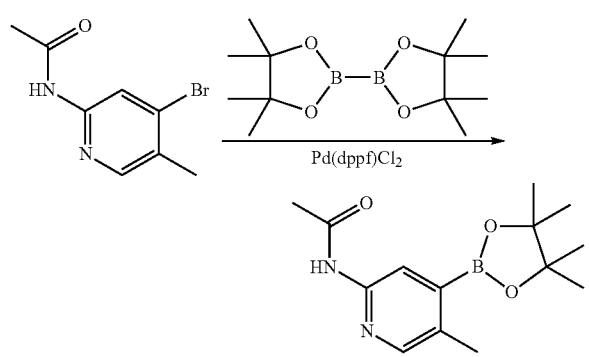

A mixture of N-(4-bromo-5-methylpyridin-2-yl)acetamide (30 g, 131 mmol), 4,4,4',4',5,5,5',5'-octamethyl-2,2'-bi-1,3,2-dioxaborolane (40 g, 157 mmol), potassium acetate (45.2 g, 459 mmol) and Pd(dppf)Cl$_2$ (10.6 g, 13 mmol) in 1,4-dioxane (900 mL) was allowed to stir under an atmosphere of nitrogen at 90° C. for 18 h. The reaction mixture was diluted with EtOAc and filtered while hot. The filtrate was concentrated to give N-[5-methyl-4-(4,4,5,5-tetramethyl-1,3,2-dioxaborolan-2-yl)pyridin-2-yl]acetamide (18.3 g, 51%).

N-[5-methyl-4-(trimethylstannyl)pyridin-2-yl]cyclopropanecarboxamide

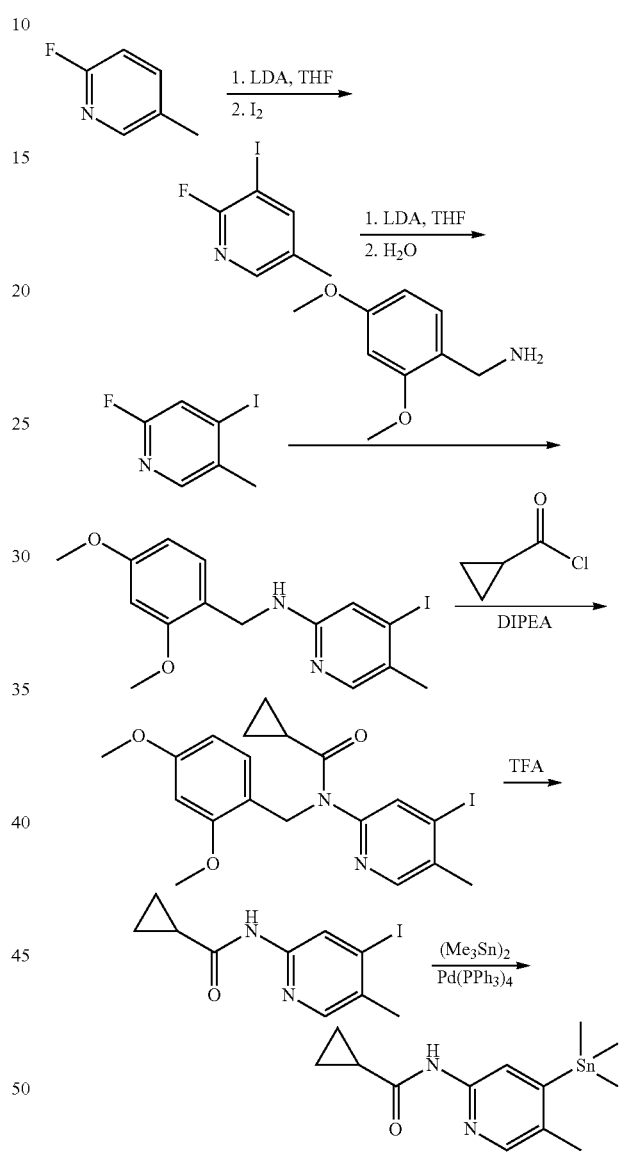

Step 1: 2-fluoro-3-iodo-5-methylpyridine

A solution of 2M LDA in THF (371 mL, 742 mmol) was added to THF (1400 mL) at −78° C. under an atmosphere of nitrogen. To this stirred, cooled solution was added 2-fluoro-5-methylpyridine (75.0 g, 67.6 mmol) in THF (280 mL) dropwise. The reaction mixture was allowed to stir at −78° C. for 2 h and then a solution of iodine (171.5 g, 67.6 mmol) in THF (560 mL) was added dropwise. The reaction mixture was allowed to stir at −78 for 2 h and then diluted with water (875 mL). The mixture was allowed to warm to rt and was then extracted with EtOAc. The organic solutions were combined, washed with brine, dried over Na$_2$SO$_4$, filtered and concentrated. The residue was purified by column chromatography to give 2-fluoro-3-iodo-5-methylpyridine (80 g, 50%).

Step 2: 2-fluoro-4-iodo-5-methylpyridine

A solution of 2M LDA in THF (186 mL, 373 mmoL) was added to THF (680 mL) at −78° C. under an atmosphere of nitrogen. To this stirred, cooled solution was added 2-fluoro-3-iodo-5-methylpyridine (80.0 g, 339 mmol) in THF (132 mL) dropwise. The reaction mixture was allowed to stir at −78° C. for 1 h and then water (6.1 mL) was added. The mixture was allowed to stir and warm to rt over 1 h and then additional water (300 mL) was added. The mixture was extracted with EtOAc and the organic solutions were combined, washed with brine, dried over Na$_2$SO$_4$, filtered and concentrated. The residue was purified by column chromatography to give 2-fluoro-4-iodo-5-methylpyridine (60 g, 75%).

Step 3: N-(2,4-dimethoxybenzyl)-4-iodo-5-methylpyridin-2-amine

A mixture of 2-fluoro-4-iodo-5-methylpyridine (60 g, 253 mmol) and 1-(2,4-dimethoxyphenyl)methanamine (190.6 mL, 1270 mmol) was allowed to stir at 110° C. overnight. The mixture was allowed to cool to rt and was then diluted with EtOAc (190 mL). The resulting solid was filtered and washed with EtOAc and then purified by column chromatography to give N-(2,4-dimethoxybenzyl)-4-iodo-5-methylpyridin-2-amine (55.0 g, 57%).

Step 4: N-(2,4-dimethoxybenzyl)-N-(4-iodo-5-methylpyridin-2-yl)cyclopropanecarboxamide To a solution of DIEA (1.8 mL, 10.4 mmol) in DCM (50 mL) at 0° C. was added N-(2,4-dimethoxybenzyl)-4-iodo-5-methylpyridin-2-amine (2.0 g, 5.2 mmol) and cyclopropanecarbonyl chloride (0.66 mL, 7.3 mmol). The reaction mixture was allowed to stir at 0° C. for 2 h and then diluted with DCM and aqueous ammonium chloride. The aqueous solution was removed and the organic solution was dried over Na$_2$SO$_4$, filtered, and concentrated. The residue was purified by column chromatography to give N-(2,4-dimethoxybenzyl)-N-(4-iodo-5-methylpyridin-2-yl)cyclopropanecarboxamide (1.8 g, 78%).

Step 5: N-(4-iodo-5-methylpyridin-2-yl)cyclopropanecarboxamide

To a solution of N-(2,4-dimethoxybenzyl)-N-(4-iodo-5-methylpyridin-2-yl)cyclopropanecarboxamide (1.8 g, 3.95 mmol) in DCM (23 mL) was added TFA. The reaction mixture was allowed to stir at rt overnight and then concentrated. The residue was diluted with DCM and aqueous saturated NaHCO$_3$ and the mixture was extracted with DCM. The organic solutions were combined, dried over Na$_2$SO$_4$, filtered and concentrated. The residue was purified by column chromatography to give N-(4-iodo-5-methylpyridin-2-yl)cyclopropanecarboxamide (1.0 g, 75%).

Step 6: N-[5-methyl-4-(trimethylstannyl)pyridin-2-yl]cyclopropanecarboxamide

A mixture of N-(4-iodo-5-methylpyridin-2-yl)cyclopropanecarboxamide (6.0 g, 19.8 mmol), hexamethyldistannane (5.4 mL, 25.8 mmol) and Pd(PPh$_3$)$_4$ in 1,4-dioxane (120 mL) was allowed to stir at 95° C. under an atmosphere of nitrogen overnight. The reaction mixture was filtered through celite and the filtrate was concentrated. The residue was purified by column chromatography to give N-[5-methyl-4-(trimethylstannyl)pyridin-2-yl]cyclopropanecarboxamide (4.1 g, 61%).

methyl[5-methyl-4-(trimethylstannyl)pyridin-2-yl] carbamate

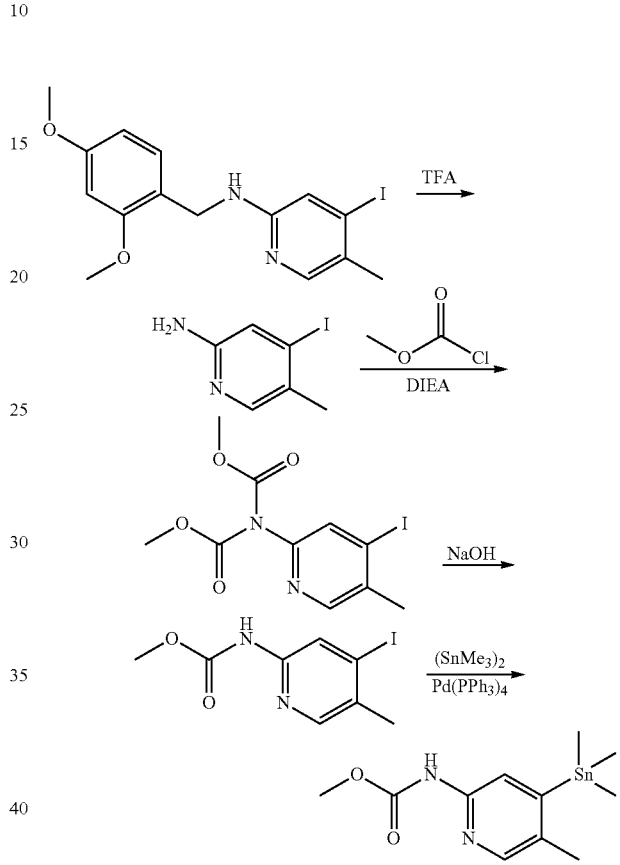

Step 1: 4-iodo-5-methylpyridin-2-amine

To a solution of N-(2,4-dimethoxybenzyl)-4-iodo-5-methylpyridin-2-amine (118 g, 310 mmol) in DCM (1900 mL) was added TFA (360 mL, 4830 mmol). The reaction mixture was allowed to stir at rt for 2 h and was then concentrated. The residue was dissolved in EtOAc and diluted with saturated aqueous NaHCO$_3$. The mixture was extracted with EtOAc. The organic solutions were combined, washed with brine, dried over Na$_2$SO$_4$, filtered and concentrated to give 4-iodo-5-methylpyridin-2-amine (53 g, 75%) which was used in the next step without purification.

Step 2: dimethyl(4-iodo-5-methylpyridin-2-yl)imidodicarbonate

To a solution of 4-iodo-5-methylpyridin-2-amine (90 g, 380 mmol) in DCM (3800 mL) were added DIEA (192 mL, 930 mmol) and methyl carbonochloridate (58.8 mL, 760 mmol) at 0° C. The reaction mixture was allowed to stir at 0° C. for 1 h and was then diluted with aqueous saturated NH$_4$Cl. The organic solvent was separated and the aqueous solution was extracted with DCM. The organic solutions were combined, washed with brine and concentrated to give dimethyl (4-iodo-5-methylpyridin-2-yl)imidodicarbonate (110 g, 80%) which was used in the next step without purification.

Step 3: methyl(4-iodo-5-methylpyridin-2-yl)carbamate

Dimethyl(4-iodo-5-methylpyridin-2-yl)imidodicarbonate (110 g, 310 mmol) was added to a mixture of MeOH (1500 mL) and 1M NaOH (620 mL). The reaction mixture was allowed to stir at rt for 1.5 h and was then concentrated. EtOAc and water were added to the residue and the solution was extracted with EtOAc. The organic solutions were combined, washed with brine, dried over $Na_2SO_4$, filtered and concentrated to give methyl(4-iodo-5-methylpyridin-2-yl)carbamate (68 g, 60%) which was used in the next step without purification.

Step 4: methyl[5-methyl-4-(trimethylstannyl)pyridin-2-yl]carbamate

A mixture of methyl(4-iodo-5-methylpyridin-2-yl)carbamate (68 g, 230 mmol), hexamethylditin (60 mL, 280 mmol) and palladium tetrakistriphenylphosphine (6.8 g, 5.9 mmol) in 1,4-dioxane (1400 mL) was allowed to stir under an atmosphere of nitrogen at 100° C. for 10 h. The reaction mixture was filtered and then concentrated. The residue was purified by column chromatography to give methyl[5-methyl-4-(trimethylstannyl)pyridin-2-yl]carbamate (15 g, 20%).

[2-chloro-5-(pyrrolidin-1-ylmethyl)phenyl]boronic acid

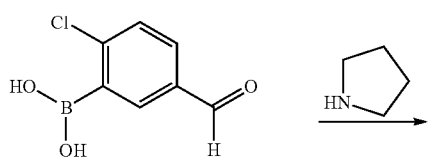

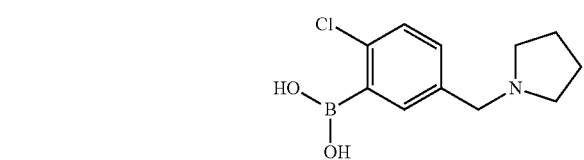

To a solution of (2-chloro-5-formylphenyl)boronic acid (1.00 g, 5.42 mmol) in DCM (30 mL) were added pyrrolidine (0.45 mL, 5.42 mmol) and sodium triacetoxyborohydride (2.39 g, 11.3 mmol). The reaction mixture was allowed to stir at rt for 2.5 h and then diluted with brine. The mixture was extracted with DCM. The organic solutions were combined, dried over $Na_2SO_4$, filtered and concentrated to give [2-chloro-5-(pyrrolidin-1-ylmethyl)phenyl]boronic acid.

Example 2

5-[2-(acetylamino)pyridin-4-yl]-2-(2-chlorophenyl)-3-furamide (Compound I-1)

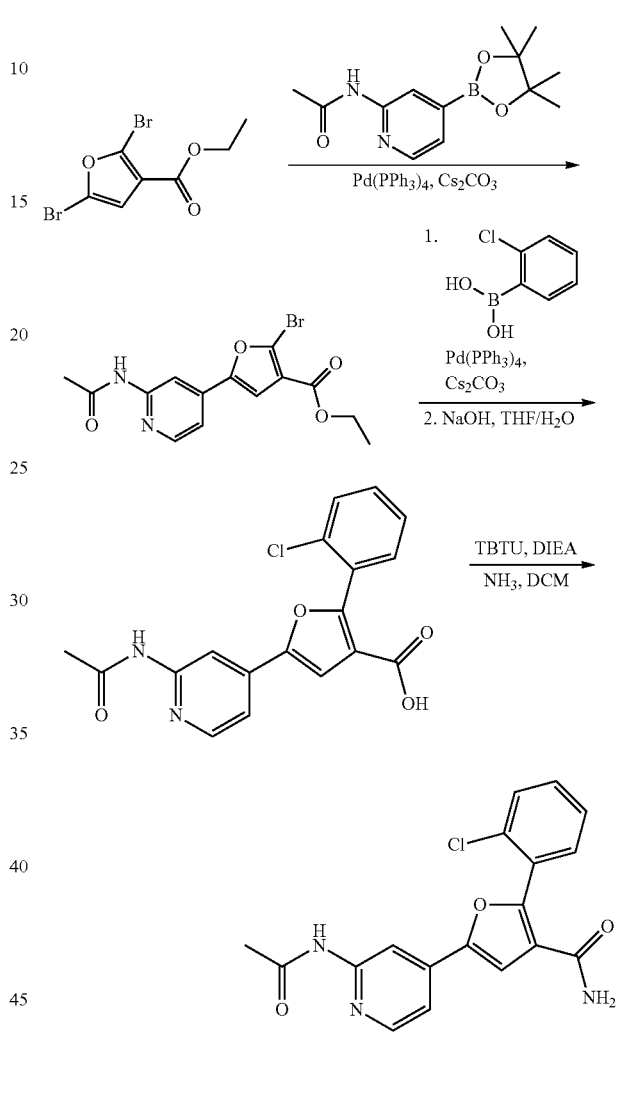

Step 1: ethyl 5-[2-(acetylamino)pyridin-4-yl]-2-bromo-3-furoate

To a solution of ethyl 2,5-dibromo-3-furoate (0.21 g, 0.722 mmol) in 1,4-dioxane (2.2 mL) and water (0.50 mL) were added tetrakis(triphenylphosphine) palladium(0) (0.08 g, 0.07 mmol), N-[4-(4,4,5,5-tetramethyl-1,3,2-dioxaborolan-2-yl)pyridin-2-yl]acetamide (0.19 g, 0.72 mmol) and cesium carbonate (0.71 g, 2.2 mmol). The reaction mixture was subjected to microwave irradiation at 95° C. for 15 min. The reaction mixture was diluted with water (10 mL) and extracted with EtOAc. The organic solutions were combined, washed with brine, dried over $Na_2SO_4$, filtered and concentrated. The residue was purified by column chromatography to give ethyl 5-[2-(acetylamino)pyridin-4-yl]-2-bromo-3-furoate (0.035 g, 14%) as a white solid. LCMS (FA): m/z=339.1 (M+H).

Step 2: 5-[2-(acetylamino)pyridin-4-yl]-2-(2-chlorophenyl)-3-furoic acid Compound I-2

To a solution of ethyl 5-[2-(acetylamino)pyridin-4-yl]-2-bromo-3-furoate (0.030 g, 0.09 mmol) in 1,4-dioxane (0.5 mL) and water (0.1 mL) were added tetrakis(triphenylphosphine)palladium(0) (0.010 g, 0.0088 mmol), (2-chlorophenyl)boronic acid (0.018 g, 0.11 mmol), and cesium carbonate (0.087 g, 0.27 mmol). The reaction mixture was subjected to microwave irradiation at 130° C. for 20 min. The reaction mixture was then diluted with water (2 mL) and 1N aqueous sodium hydroxide (0.25 mL) was added. The mixture was allowed to stir at rt overnight. The reaction mixture was extracted with EtOAc and the organic solutions were combined and concentrated. The residue was purified by column chromatography to give 5-[2-(acetylamino)pyridin-4-yl]-2-(2-chlorophenyl)-3-furoic acid (0.015 g, 50%) as a white solid. LCMS (FA): m/z=357.4 (M+H).

Step 3: 5-[2-(acetylamino)pyridin-4-yl]-2-(2-chlorophenyl)-3-furamide

To a solution of 5-[2-(acetylamino)pyridin-4-yl]-2-(2-chlorophenyl)-3-furoic acid (0.10 g, 0.28 mmol) in DCM (15 mL) was added ammonia (0.5 M in 1,4-dioxane, 4.5 mL), TBTU (0.18 g, 0.56 mmol) and DMA (0.49 mL, 2.8 mmol). The mixture was allowed to stir at rt overnight. The reaction mixture was diluted with water and extracted with DCM. The organic solutions were combined, washed with brine, dried over Na₂SO₄, filtered and concentrated. The residue was purified by column chromatography to give 5-[2-(acetylamino)pyridin-4-yl]-2-(2-chlorophenyl)-3-furamide (0.062 g, 62%) as a white solid. LCMS (FA): m/z=356.5 (M+H).

Compounds in the following table were prepared from the appropriate starting materials using the procedures described above:

| | |
|---|---|
| I-83 | LCMS (FA): m/z = 370.4 (M + H). |
| I-56 | LCMS (FA): m/z = 371.5 (M + H). |
| I-66 | LCMS (FA): m/z = 428.4 (M + H). |
| I-54 | LCMS (FA): m/z = 384.4 (M + H). |
| I-41 | LCMS (FA): m/z = 514.5 (M + H). |
| I-42 | LCMS (FA): m/z = 466.5 (M + H). |
| I-53 | LCMS (FA): m/z = 460.5 (M + H). |
| I-88 | LCMS (FA): m/z = 450.5 (M + H). |
| I-44 | LCMS (FA): m/z = 461.6 (M + H). |
| I-68 | LCMS (FA): m/z = 461.5 (M + H). |
| I-15 | LCMS (FA): m/z = 453.5 (M + H). |
| I-61 | LCMS (FA): m/z = 398.6 (M + H). |
| I-24 | LCMS (FA): m/z = 478.6 (M + H). |
| I-81 | LCMS (FA): m/z = 398.5 (M + H). |
| I-72 | LCMS (FA): m/z = 412.6 (M + H). |
| I-19 | LCMS (FA): m/z = 446.6 (M + H). |
| I-80 | LCMS (FA): m/z = 440.6 (M + H). |
| I-12 | LCMS (FA): m/z = 464.6 (M + H). |
| I-29 | LCMS (FA): m/z = 428.6 (M + H). |
| I-34 | LCMS (FA): m/z = 458.6 (M + H). |
| I-14 | LCMS (FA): m/z = 424.6 (M + H). |
| I-85 | LCMS (FA): m/z = 503.6 (M + H). |
| I-84 | LCMS (FA): m/z = 481.6 (M + H). |

Example 3

N-{4-[5-(2-chlorophenyl)-4-(4H-1,2,4-triazol-3-yl)-(3-oxazol-2-yl]-5-methylpyridin-2-yl}acetamide (Compound I-4)

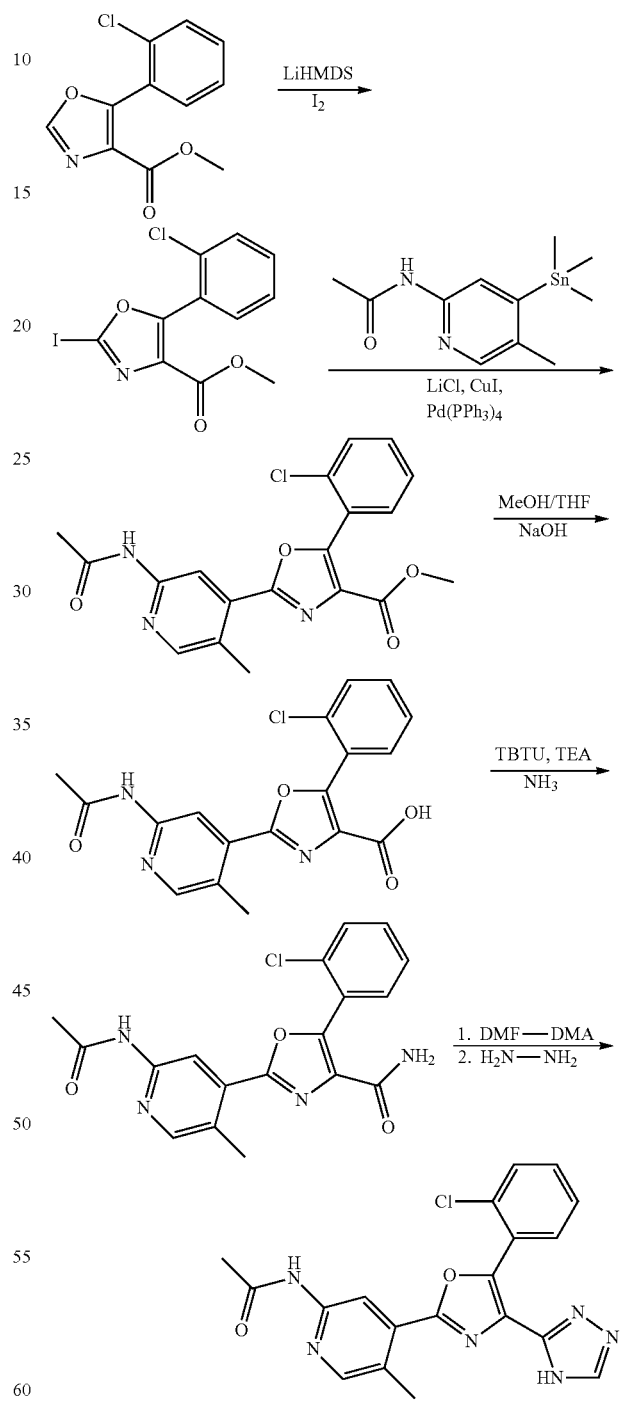

Step 1: methyl 5-(2-chlorophenyl)-2-iodo-1,3-oxazole-4-carboxylate

To a round bottom flask were added methyl 5-(2-chlorophenyl)-1,3-oxazole-4-carboxylate (2.25 g, 9.5 mmol) and THF (50 mL). The mixture was cooled to −78° C. LiHMDS (1M in hexane, 12.3 mL, 12.3 mmol) was added dropwise. The mixture was allowed to stir at −78° C. for 1 h. Iodine (3.60 g, 14.2 mmol) was added and the mixture was allowed to stir at −78° C. for 20 min. The mixture was allowed to warm to rt and stir overnight. The reaction mixture was poured into 10% sodium thiosulfate (100 mL) and was extracted with EtOAc. The organic solutions were combined, washed with brine, dried over MgSO$_4$, filtered, and concentrated to give methyl 5-(2-chlorophenyl)-2-iodo-1,3-oxazole-4-carboxylate (3.0 g, 87%) which was used without further purification.

Step 2: methyl 2-[2-(acetylamino)-5-methylpyridin-4-yl]-5-(2-chlorophenyl)-1,3-oxazole-4-carboxylate A mixture of methyl 5-(2-chlorophenyl)-2-iodo-1,3-oxazole-4-carboxylate (3.0 g, 8.3 mmol), N-[5-methyl-4-(trimethylstannyl)pyridine-2-yl]acetamide (2.8 g, 9.1 mmol), tetrakis(triphenylphosphine)palladium(0) (0.48 g, 0.41 mmol), copper(I) iodide (0.47 g, 2.5 mmol) and lithium chloride (1.1 g, 24.8 mmol) in 1,4-dioxane (80 mL) was degassed with argon three times. The mixture was allowed to stir at 100° C. under an atmosphere of argon for 2 h and then filtered while hot. The reaction mixture was concentrated to a small volume and then 10% aqueous ammonia (150 mL) was added. The mixture was filtered and the solid was washed with diethyl ether to give methyl 2-[2-(acetylamino)-5-methylpyridin-4-yl]-5-(2-chlorophenyl)-1,3-oxazole-4-carboxylate (2.3 g, 72%) which was used without further purification.

Step 3: 2-[2-(acetylamino)-5-methylpyridin-4-yl]-5-(2-chlorophenyl)-1,3-oxazole-4-carboxylic acid (Compound I-6)

To a round bottom flask was added methyl 2-[2-(acetylamino)-5-methylpyridin-4-yl]-5-(2-chlorophenyl)-1,3-oxazole-4-carboxylate (2.30 g, 6.0 mmol), THF (20 mL), MeOH (30 mL), and 1M aqueous NaOH (25 mL). The reaction mixture was allowed to stir at rt overnight. The mixture was concentrated and 1M aqueous HCl was added until the solution became acidic. The mixture was filtered and the solid was dried to give 2-[2-(acetylamino)-5-methylpyridin-4-yl]-5-(2-chlorophenyl)-1,3-oxazole-4-carboxylic acid (Compound I-6) (1.4 g, 64%). LCMS (FA): m/z=372.2 (M+H).

Step 4: 2-[2-(acetylamino)-5-methylpyridin-4-yl]-5-(2-chlorophenyl)-1,3-oxazole-4-carboxamide Compound I-3)

To a round bottom flask was added 2-[2-(acetylamino)-5-methylpyridin-4-yl]-5-(2-chlorophenyl)-1,3-oxazole-4-carboxylic acid (1.1 g, 2.8 mmol), DCM (35 mL), TBTU (3.6 g, 11.3 mmol), and TEA (3.0 mL, 21.5 mmol). The mixture was allowed to stir for 5 min at rt and then ammonia (0.5M in dioxane, 32 mL) was added. The resulting mixture was allowed to stir at rt overnight. The mixture was concentrated and the residue was washed with water to give 2-[2-(acetylamino)-5-methylpyridin-4-yl]-5-(2-chlorophenyl)-1,3-oxazole-4-carboxamide (0.96 g, 92%). LCMS (FA): m/z=371.0 (M+H).

Step 5: N-{4-[5-(2-chlorophenyl)-4-(4H-1,2,4-triazol-3-yl)-1,3-oxazol-2-yl]-5-methylpyridin-2-yl}acetamide A suspension of 2-[2-(acetylamino)-5-methylpyridin-4-yl]-5-(2-chlorophenyl)-1,3-oxazole-4-carboxamide (0.48 g, 1.3 mmol) in dry toluene (7 mL) was sonicated for 15 min. DMF-DMA (0.51 mL, 3.8 mmol) was added and the mixture was allowed to stir at 50° C. for 2 h. The suspension was cooled to rt and was concentrated. The resulting solid was suspended in AcOH (5 mL) at rt. Hydrazine (0.20 mL, 6.4 mmol) was added dropwise. The reaction mixture was allowed to stir at 40° C. for 3 h. Saturated NaHCO$_3$ was added until the mixture became neutral. The solid was filtered, washed with water, and purified by column chromatography to give N-{4-[5-(2-chlorophenyl)-4-(4H-1,2,4-triazol-3-yl)-1,3-oxazol-2-yl]-5-methylpyridin-2-yl}acetamide (0.23 g, 45%). LCMS (FA): m/z=395.3 (M+H).

Compounds in the following table were prepared from the appropriate starting materials using the procedures described above:

| | |
|---|---|
| I-70 | LCMS (FA): m/z = 465.5 (M + H). |
| I-11 | LCMS (FA): m/z = 441.5 (M + H). |
| I-21 | LCMS (FA): m/z = 413.5 (M + H). |
| I-13 | LCMS (FA): m/z = 443.5 (M + H). |
| I-59 | LCMS (FA): m/z = 399.4 (M + H). |
| I-63 | LCMS (FA): m/z = 479.5 (M + H). |
| I-73 | LCMS (FA): m/z = 399.4 (M + H). |
| I-47 | LCMS (FA): m/z = 462.5 (M + H). |
| I-20 | LCMS (FA): m/z = 462.4 (M + H). |
| I-55 | LCMS (FA): m/z = 461.4 (M + H). |
| I-38 | LCMS (FA): m/z = 467.4 (M + H). |
| I-31 | LCMS (FA): m/z = 449.4 (M + H). |
| I-82 | LCMS (FA): m/z = 515.4 (M + H). |
| I-52 | LCMS (FA): m/z = 385.4 (M + H). |
| I-9 | LCMS (FA): m/z = 451.4 (M + H). |
| I-74 | LCMS (FA): m/z = 425.4 (M + H). |
| I-25 | LCMS (FA): m/z = 459.3 (M + H). |
| I-64 | LCMS (FA): m/z = 429.3 (M + H). |
| I-62 | LCMS (FA): m/z = 429.3 (M + H). |

Example 4

2-[2-(acetylamino)-5-methylpyridin-4-yl]-4-(2-chlorophenyl)-1,3-oxazole-5-carboxamide (Compound I-5)

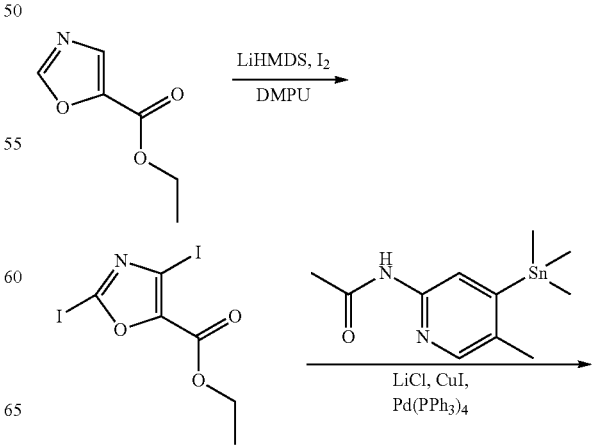

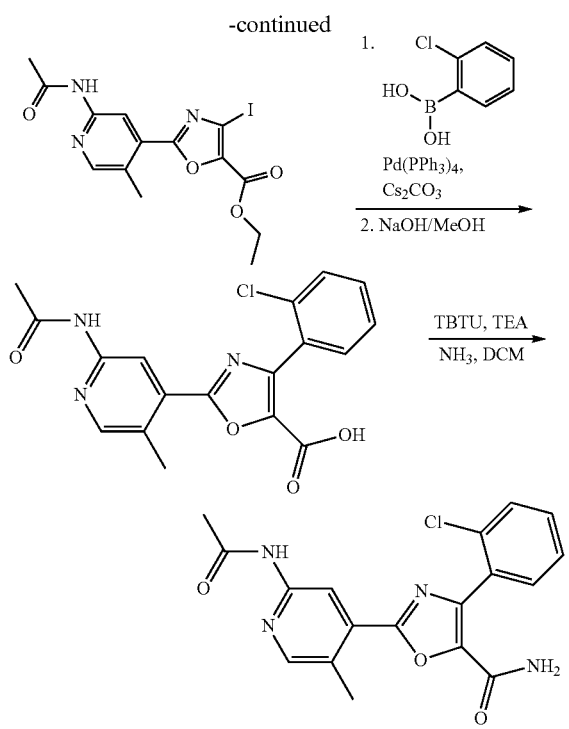

Step 1: ethyl 2,4-diiodo-1,3-oxazole-5-carboxylate

To a round bottom flask was added ethyl 1,3-oxazole-5-carboxylate (1.0 g, 7.2 mmol), THF (12 mL), and DMPU (10 mL). The mixture was cooled to −50° C. LiHMDS (1M in hexane, 9.0 mL) was added dropwise. The resulting mixture was allowed to stir for 30 min at −50° C. Iodine (2.1 g, 8.3 mmol) in THF (15 mL) was added dropwise at −50° C. After addition was complete, the mixture was cooled to −78° C. and was allowed to stir at that temperature for 1 h. The mixture was then poured into 150 mL of 10% sodium thiosulfate solution. The mixture was extracted with EtOAc and the organic solution was concentrated. The residue was purified by column chromatography to give ethyl 2,4-diiodo-1,3-oxazole-5-carboxylate (0.36 g, 13%).

Step 2: ethyl 2-[2-(acetylamino)-5-methylpyridin-4-yl]-4-iodo-1,3-oxazole-5-carboxylate A mixture of ethyl 2,4-diiodo-1,3-oxazole-5-carboxylate (0.37 g, 0.93 mmol), N-[5-methyl-4-(trimethylstannyl)pyridine-2-yl]acetamide (0.32 g, 1.0 mmol), tetrakis(triphenylphosphine)palladium(0) (0.054 g, 0.047 mmol), copper (I) iodide (0.053 g, 0.28 mmol) and lithium chloride (0.12 g, 2.8 mmol) in 1,4-dioxane (9 mL) was degassed with argon three times. The mixture was allowed to stir at 100° C. for 2 h under an atmosphere of argon and was then filtered while hot. The reaction mixture was concentrated and the residue was purified by column chromatography to give ethyl 2-[2-(acetylamino)-5-methylpyridin-4-yl]-4-iodo-1,3-oxazole-5-carboxylate (0.16 g, 42%).

Step 3: 2-[2-(acetylamino)-5-methylpyridin-4-yl]-4-(2-chlorophenyl)-1,3-oxazole-5-carboxylic acid A mixture of ethyl 2-[2-(acetylamino)-5-methylpyridin-4-yl]-4-iodo-1,3-oxazole-5-carboxylate (0.14 g, 0.33 mmol), (2-chlorophenyl)boronic acid (0.076 g, 0.49 mmol), tetrakis(triphenylphosphine)palladium(0) (0.038 g, 0.032 mmol), and cesium carbonate (0.53 g, 1.62 mmol) in 1,4-dioxane (4.5 mL) and water (0.2 mL) was subjected to microwave irradiation at 150° C. for 20 min. The reaction mixture was filtered and the filtrate was concentrated. To the residue were added MeOH (10 mL) and aqueous NaOH (0.5 M, 1.5 mL). The mixture was allowed to stir at rt for 8 h and then concentrated to give 2-[2-(acetylamino)-5-methylpyridin-4-yl]-4-(2-chlorophenyl)-1,3-oxazole-5-carboxylic acid which was used in next step without further purification.

Step 4: 2-[2-(acetylamino)-5-methylpyridin-4-yl]-4-(2-chlorophenyl)-1,3-oxazole-5-carboxamide To a round bottom flask was added 2-[2-(acetylamino)-5-methylpyridin-4-yl]-4-(2-chlorophenyl)-1,3-oxazole-5-carboxylic acid (0.12 g, 0.33 mmol), DCM (4 mL), TBTU (0.42 g, 1.3 mmol), and TEA (0.35 mL, 2.5 mmol). The mixture was allowed to stir for 5 min at rt, and then ammonia (0.5M in dioxane, 32 mL) was added. The resulting mixture was allowed to stir at rt overnight and then concentrated. DCM and water were added. The organic solution was separated, dried over $MgSO_4$, filtered and concentrated. The residue was purified by column chromatography to give 2-[2-(acetylamino)-5-methylpyridin-4-yl]-4-(2-chlorophenyl)-1,3-oxazole-5-carboxamide (0.018 g, 15%). LCMS (FA): m/z=371.4 (M+H).

Compounds in the following table were prepared from the appropriate starting materials using the procedures described above:

| | |
|---|---|
| I-28 | LCMS (AA): m/z = 454.3 (M + H). |
| I-51 | LCMS (AA): m/z = 455.0 (M + H). |

Example 5

N-{4-[5-(2-chlorophenyl)-4-(1H-1,2,4-triazol-3-yl)-1,3-oxazol-2-yl]phenyl}acetamide (Compound I-8)

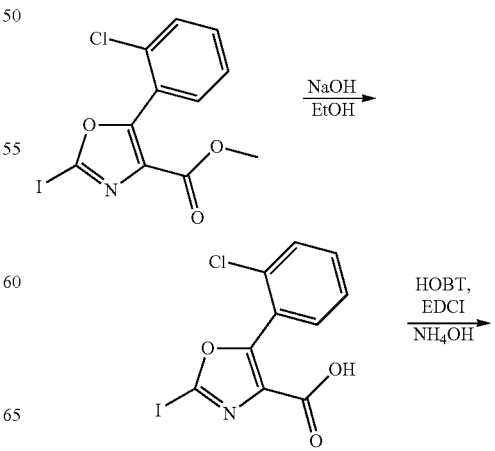

81

-continued

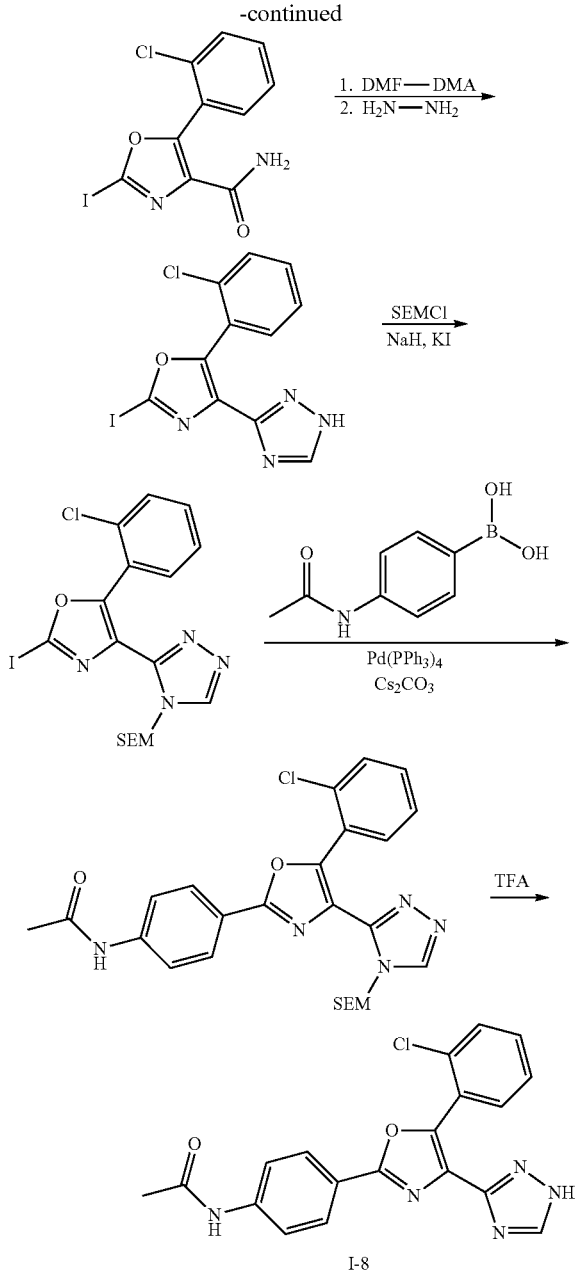

Step 1:
5-(2-chlorophenyl)-2-iodo-1,3-oxazole-4-carboxylic acid

To a stirred solution of methyl 5-(2-chlorophenyl)-2-iodo-1,3-oxazole-4-carboxylate (20.0 g, 55.2 mmol) in EtOH (300 mL) was added a solution of NaOH (3.3 g, 82.8 mmol) in water (100 mL). The reaction mixture was allowed to stir at rt overnight and was then acidified by the addition of 1M HCl. The solution was concentrated to a small volume and then extracted with EtOAc. The organic solutions were combined, dried over Na₂SO₄, filtered and concentrated to give 5-(2-chlorophenyl)-2-iodo-1,3-oxazole-4-carboxylic acid (12.0 g, 60%).

82

Step 2: 5-(2-chlorophenyl)-2-iodo-1,3-oxazole-4-carboxamide

To a solution of 5-(2-chlorophenyl)-2-iodo-1,3-oxazole-4-carboxylic acid (20.0 g, 57.3 mmol) in DCM (400 mL) and DMF (200 mL) were added HOBt (8.0 g, 60.0 mmol) and EDCI (15.0 g, 80.0 mmol). The reaction mixture was allowed to stir at rt for 2 h and then NH₄OH (20 mL) in 1,4-dioxane (400 mL) was added. The reaction mixture was allowed to stir at rt overnight and then was diluted with EtOAc and washed with brine. The organic solution was dried over MgSO₄, filtered and concentrated. The residue was purified by column chromatography to give 5-(2-chlorophenyl)-2-iodo-1,3-oxazole-4-carboxamide (18.0 g, 85%).

Step 3: 3-[5-(2-chlorophenyl)-2-iodo-1,3-oxazol-4-yl]-1H-1,2,4-triazole

To a mixture of 5-(2-chlorophenyl)-2-iodo-1,3-oxazole-4-carboxamide (18.0 g, 51.7 mmol) in toluene (400 mL) was added DMF-DMA (8.5 g, 70.0 mmol). The reaction mixture was allowed to stir at 70° C. for 4 h and was then concentrated. The residue was redissolved in AcOH (400 mL) and hydrazine (40 mL) was added. The reaction mixture was allowed to stir at 70° C. for 5 h and then to cool to rt. Saturated NaHCO₃ was added until the mixture became neutral. The solid was filtered, washed with water, and purified by column chromatography to give 3-[5-(2-chlorophenyl)-2-iodo-1,3-oxazol-4-yl]-1H-1,2,4-triazole (16.0 g, 86.5%).

Step 4: 3-[5-(2-chlorophenyl)-2-iodo-1,3-oxazol-4-yl]-4-{[2-(trimethylsilyl)-ethoxy]methyl}-4H-1,2,4-triazole To a mixture of 3-[5-(2-chlorophenyl)-2-iodo-1,3-oxazol-4-yl]-1H-1,2,4-triazole (26.0 g, 70.0 mmol), SEM-Cl (16.6 g, 100.0 mmol) and potassium iodide (1.6 g, 10.0 mmol) in DMF (400 mL) was added NaH (4.0 g, 100 mmol). The reaction mixture was allowed to stir at rt until the reaction was complete (as judged by TLC analysis). The reaction mixture was poured into water and extracted with EtOAc. The organic solutions were combined, dried over MgSO₄, filtered and concentrated. The residue was purified by column chromatography to give 3-[5-(2-chlorophenyl)-2-iodo-1,3-oxazol-4-yl]-4-{[2-(trimethylsilyl)-ethoxy]methyl}-4H-1,2,4-triazole (3.9 g, 11%) plus two other SEM regioisomers (9.39 g, 26.2%). All three isomers could be separated and could be used for the following steps.

Step 5: N-{4-[5-(2-chlorophenyl)-4-(4-{[2-(trimethylsilyl)ethoxy]methyl}-4H-1,2,4-triazol-3-yl)-1,3-oxazol-2-yl]phenyl}acetamide A mixture of 3-[5-(2-chlorophenyl)-2-iodo-1,3-oxazol-4-yl]-4-{[2-(trimethylsilyl)-ethoxy]methyl}-4H-1,2,4-triazole (0.11 g, 0.22 mmol), tetrakis(triphenylphosphine)palladium (0) (0.050 g, 0.043 mmol), (4-acetamidophenyl)boronic acid (0.115 g, 0.64 mmol) and cesium carbonate (0.46 g, 1.40 mmol) in 1,4-dioxane (2 mL) and water (0.2 mL) was sealed in a tube and subjected to microwave irradiation at 150° C. for 60 min. The reaction mixture was concentrated and the residue was purified by column chromatography to give N-{4-[5-(2-chlorophenyl)-4-(4-{[2-(trimethylsilyl)ethoxy]methyl}-4H-1,2,4-triazol-3-yl)-1,3-oxazol-2-yl]phenyl}acetamide (0.100 g, 91%). LCMS (AA): m/z=510 (M+H).

Step 6: N-{4-[5-(2-chlorophenyl)-4-(1H-1,2,4-triazol-3-yl)-1,3-oxazol-2-yl]phenyl}acetamide (Compound I-8)

TFA (0.6 mL) was added to a solution of N-{4-[5-(2-chlorophenyl)-4-(4-{[2-(trimethylsilyl)ethoxy]methyl}-4H-1,2,4-triazol-3-yl)-1,3-oxazol-2-yl]phenyl}acetamide (0.10 g, 0.20 mmol) in DCM (3 mL). The reaction mixture was allowed to stir at rt overnight and then concentrated. The residue was purified by column chromatography to give N-{4-[5-(2-chlorophenyl)-4-(1H-1,2,4-triazol-3-yl)-1,3-oxazol-2-yl]phenyl}acetamide (Compound I-8) (0.026 g, 32%). LCMS (FA): m/z=380 (M+H).

Compounds in the following table were prepared from the appropriate starting materials using the procedures described above:

| | |
|---|---|
| I-35 | LCMS (AA): m/z = 411 (M + H). |
| I-32 | LCMS (AA): m/z = 339 (M + H). |
| I-77 | LCMS (AA): m/z = 421 (M + H). |
| I-49 | LCMS (AA): m/z = 324 (M + H). |
| I-71 | LCMS (AA): m/z = 363 (M + H). |

Example 6

5-(2-chlorophenyl)-2-{2-[(cyclopropylcarbonyl)amino]-5-methylpyridin-4-yl}-1,3-oxazole-4-carboxamide (Compound I-86)

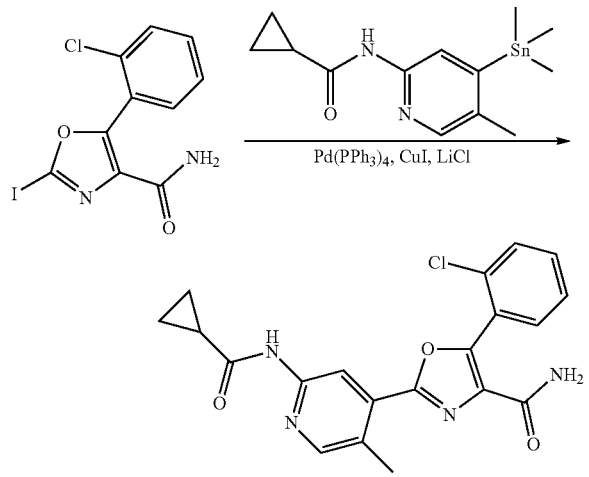

A mixture of 5-(2-chlorophenyl)-2-iodo-1,3-oxazole-4-carboxamide (0.051 g, 0.14 mmol), N-[5-methyl-4-(trimethylstannyl)pyridine-2-yl]cyclopropanecarboxamide (0.064 g, 0.19 mmol), tetrakis(triphenylphosphine)palladium(0) (0.008 g, 0.007 mmol), copper(I) iodide (0.008 g, 0.043 mmol), and lithium chloride (0.018 g, 0.43 mmol) in 1,4-dioxane (1.5 mL) was degassed with argon three times and then allowed to stir at 100° C. under an atmosphere of argon for 5 h. The reaction mixture was filtered while hot and the filtrate was concentrated. The residue was purified by column chromatography to give 5-(2-chlorophenyl)-2-{2-[(cyclopropylcarbonyl)amino]-5-methylpyridin-4-yl}-1,3-oxazole-4-carboxamide (Compound I-86) (0.036 g, 62%). LCMS (AA): m/z=397 (M+H).

Example 7

N-{4-[5-(2-chlorophenyl)-4-(1H-pyrazol-3-yl)-1,3-oxazol-2-yl]-5-methylpyridin-2-yl}acetamide (Compound I-30)

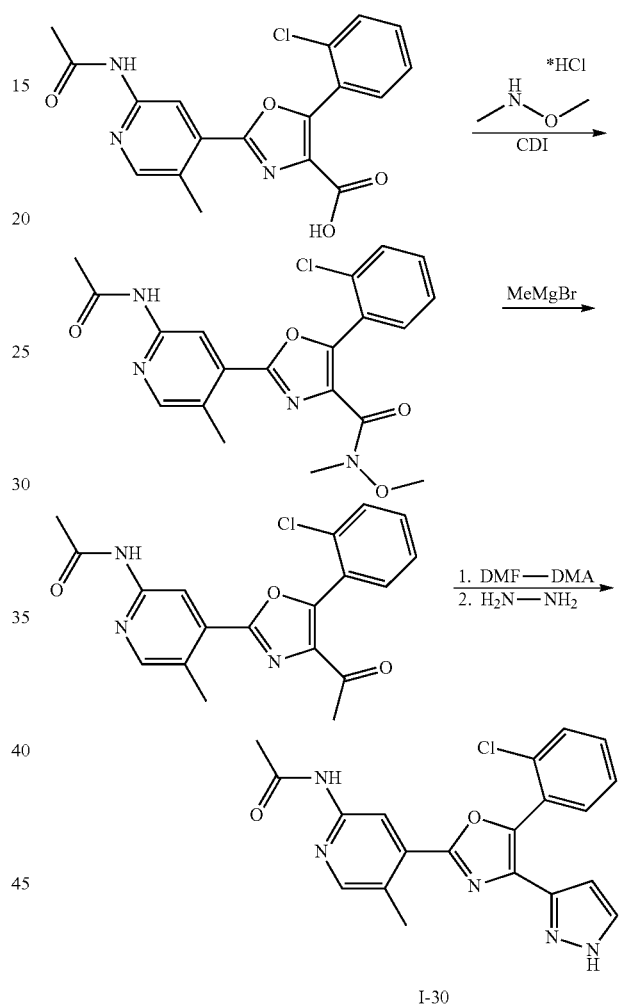

Step 1: 2-(2-acetamido-5-methylpyridin-4-yl)-5-(2-chlorophenyl)-N-methoxy-N-methyl-1,3-oxazole-4-carboxamide To a solution of 2-(2-acetamido-5-methylpyridin-4-yl)-5-(2-chlorophenyl)-1,3-oxazole-4-carboxylic acid (0.303 g, 0.815 mmol) in DCM (2 mL) was added CDI (0.14 g, 0.87 mmol). The reaction mixture was allowed to stir at rt for 30 min, then at reflux for 30 min. The reaction mixture was allowed to cool to rt and TEA (0.125 mL, 0.896 mmol) and N-methoxymethanamine hydrochloride (0.835 g, 0.856 mmol) were added. The reaction mixture was allowed to stir at rt overnight and then diluted with water. The aqueous solution was separated and extracted with DCM. The organic solutions were combined, washed sequentially with 10% citric acid, saturated aq. NaHCO₃ (50 mL) and brine, dried over Na₂SO₄, filtered and concentrated to give 2-(2-acetamido-5-methylpyridin-4-yl)-5-(2-chlorophenyl)-N-methoxy-N-methyl-1,3-oxazole-4-carboxamide (0.187 g, 55%), which was used without purification in the next step. LCMS (FA): m/z=415.4 (M+H).

Step 2: N-{4-[4-acetyl-5-(2-chlorophenyl)-1,3-oxazol-2-yl]-5-methylpyridin-2-yl}acetamide Methylmagnesium bromide (3.0 M in diethyl ether, 0.18 mL, 0.53 mmol) was added to 2-(2-acetamido-5-methylpyridin-4-yl)-5-(2-chlorophenyl)-N-methoxy-N-methyl-1,3-oxazole-4-carboxamide (0.19 g, 0.45 mmol) in THY (1 mL) under an atmosphere of argon at 0° C. The reaction mixture was allowed to warm to rt and stir overnight and then additional methylmagnesium bromide (3.0 M in diethyl ether, 0.30 mL, 0.90 mmol) was added. The reaction mixture was then allowed to stir for 24 hr. Aqueous HCl was added and then the mixture was basified with NaHCO₃ and washed with EtOAc. The organic solutions were combined, dried over MgSO₄, filtered and concentrated. The residue was purified by column chromatography to give N-{4-[4-acetyl-5-(2-chlorophenyl)-1,3-oxazol-2-yl]-5-methylpyridin-2-yl}acetamide (0.12 g, 54%). LCMS (FA): m/z=370.0 (M+H).

Step 3: N-{4-[5-(2-chlorophenyl)-4-(1H-pyrazol-3-yl)-1,3-oxazol-2-yl]-5-methylpyridin-2-yl}acetamide (Compound I-30)

A solution of N-{4-[4-acetyl-5-(2-chlorophenyl)-1,3-oxazol-2-yl]-5-methylpyridin-2-yl}acetamide (0.12 g, 0.24 mmol) and DMF-DMA (0.84 mL, 0.63 mmol) in toluene (0.5 mL) was allowed to stir at 100° C. for 5 days, during which time several additional portions of DMF-DMA were added. The reaction mixture was concentrated and the residue was redissolved in AcOH (2 mL). Hydrazine hydrate (0.13 mL, 2.63 mmol) was added and the reaction mixture was allowed to stir at 100° C. for 4 days. The reaction mixture was concentrated and the residue was purified by column chromatography to give N-{4-[5-(2-chlorophenyl)-4-(1H-pyrazol-3-yl)-1,3-oxazol-2-yl]-5-methylpyridin-2-yl}acetamide (Compound I-30) (0.34 g, 35%). LCMS (FA): m/z=394 (M+H).

Compounds in the following table were prepared from the appropriate starting materials using the procedures described above:

| | |
|---|---|
| I-57 | LCMS (FA): m/z = 394 (M + H). |
| I-46 | LCMS (FA): m/z = 414.0 (M + H). |
| I-27 | LCMS (FA): m/z = 369.0 (M + H). |
| I-48 | LCMS (FA): m/z = 393.5 (M + H). |

Example 8

N-{4-[5'-(2-chlorophenyl)-2,4'-bi-1,3-oxazol-2'-yl]-5-methylpyridin-2-yl}acetamide (Compound I-10)

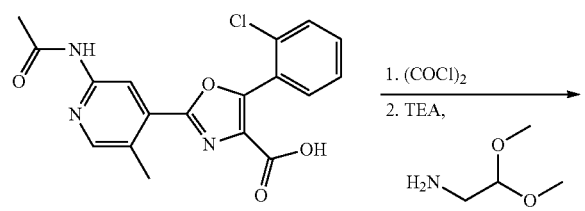

Step 1: 2-(2-acetamido-5-methylpyridin-4-yl)-5-(2-chlorophenyl)-N-(2,2-dimethoxyethyl)-1,3-oxazole-4-carboxamide A solution of 2-(2-acetamido-5-methylpyridin-4-yl)-5-(2-chlorophenyl)-1,3-oxazole-4-carboxylic acid (0.50 g, 1.34 mmol) in DCM (15 mL) and DMF (0.05 mL) was allowed to stir at 0° C. To this solution was added oxalyl chloride (0.23 mL, 2.69 mmol) dropwise. The reaction mixture was allowed to stir at 0° C. for 15 minutes and then allowed to warm to rt and stir for 2 hr. The reaction mixture was concentrated, and then DCM (15 mL) and TEA (0.38 mL, 2.69 mmol) were added. The reaction mixture was allowed to stir at 0° C. and a solution of 2,2-dimethoxyethanamine (0.29 mL, 2.69 mmol) in DCM (5 mL) was added dropwise. The reaction mixture was allowed to warm to rt and to stir overnight and then concentrated. The residue was redissolved in water and EtOAc. The organic solution was separated and the aqueous solution was further extracted with EtOAc. The organic solutions were combined, dried over MgSO₄, filtered and concentrated. The residue was purified by column chromatography to give 2-(2-acetamido-5-methylpyridin-4-yl)-5-(2-chlorophenyl)-N-(2,2-dimethoxyethyl)-1,3-oxazole-4-carboxamide (0.226 g, 37%). LCMS (FA): m/z=459 (M+H).

Step 2: N-{4-[5'-(2-chlorophenyl)-2,4'-bi-1,3-oxazol-2'-yl]-5-methylpyridin-2-yl}acetamide (Compound I-10)

A mixture of 2-(2-acetamido-5-methylpyridin-4-yl)-5-(2-chlorophenyl)-N-(2,2-dimethoxyethyl)-1,3-oxazole-4-carboxamide (0.226 g, 0.492 mmol) and Eaton's Reagent (7.7 wt % phosphorus pentoxide solution in methanesulfonic acid, 1.2 mL) was allowed to stir at 130° C. for 3 hr. Water was added to the reaction mixture and the solution was extracted with EtOAc. The organic solutions were combined, washed with brine and aqueous sat. NaHCO₃, dried over MgSO₄, filtered and concentrated. The residue was purified by column chromatography to give N-{4-[5'-(2-chlorophenyl)-2,4'-bi-1,3-oxazol-2'-yl]-5-methylpyridin-2-yl}acetamide (Compound I-10) (0.005 g, 2%). LCMS (FA): m/z=395 (M+H).

Compounds in the following table were prepared from the appropriate starting materials using the procedures described above:

| | |
|---|---|
| I-33 | LCMS (FA): m/z = 395 (M + H). |
| I-22 | LCMS (FA): m/z = 458.5 (M + H). |
| I-69 | LCMS (FA): m/z = 394.5 (M + H). |

Example 9

N-{4-[4-(2-chlorophenyl)-5-(pyridine-2-yl)-1,3-oxazol-2-yl]-5-methylpyridin-2-yl}acetamide (Compound I-78)

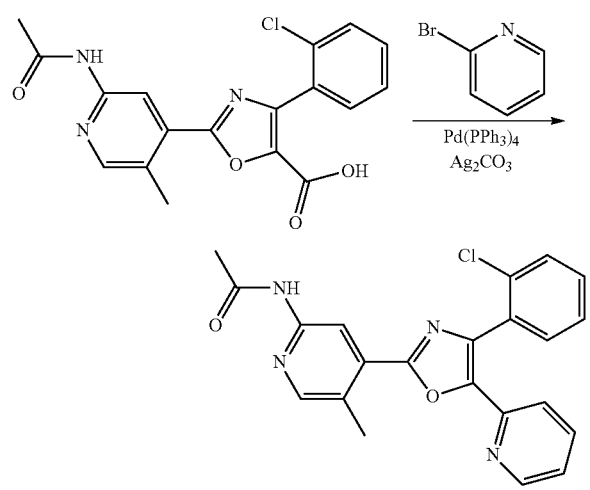

Step 1: N-{4-[4-(2-chlorophenyl)-5-(pyridine-2-yl)-1,3-oxazol-2-yl]-5-methylpyridin-2-yl}acetamide (Compound I-78)

A mixture of N-{4-[4-(2-chlorophenyl)-5-(pyridine-2-yl)-1,3-oxazol-2-yl]-5-methylpyridin-2-yl}acetamide (0.25 g, 0.672 mmol), 2-bromopyridine (0.13 mL, 1.3 mmol), tetrakis(triphenylphosphine)palladium(0) (0.077 g, 0.067 mmol) and silver carbonate (0.37 g, 1.35 mmol) in DMF (10 mL) was sealed in a tube and subjected to microwave irradiation at 170° C. for 15 min. The reaction mixture was diluted with water and extracted with EtOAc. The organic solutions were combined, washed with water and aqueous LiCl solution, dried over MgSO$_4$, filtered and concentrated. The residue was purified by column chromatography to give N-{4-[4-(2-chlorophenyl)-5-(pyridine-2-yl)-1,3-oxazol-2-yl]-5-methylpyridin-2-yl}acetamide (Compound I-78) (0.094 g, 31%). LCMS (FA): m/z=395 (M+H).

Compounds in the following table were prepared from the appropriate starting materials using the procedures described above:

| | |
|---|---|
| I-60 | LCMS (FA): m/z = 411 (M + H). |

Example 10

N-{4-[3-(2-chlorophenyl)-4-(4H-1,2,4-triazol-3-yl)-1,3-oxazol-2-yl]-5-methylpyridin-2-yl}cyclopropanecarboxamide (Compound I-77)

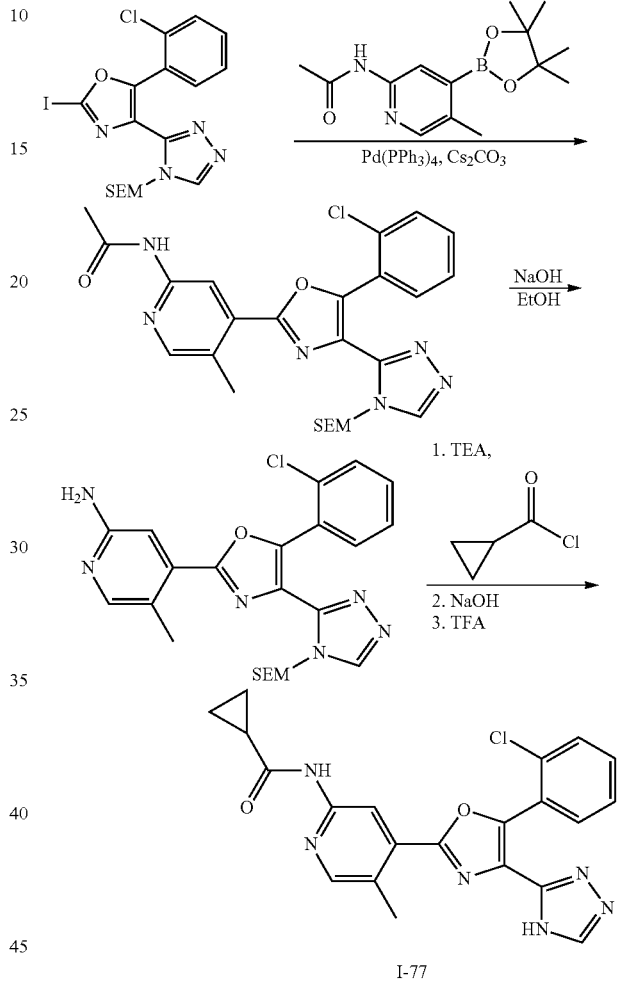

Step 1: N-{4-[5-(2-chlorophenyl)-4-(4-{[2-(trimethylsilyl)ethoxy]methyl}-4H-1,2,4-triazol-3-yl)-1,3-oxazol-2-yl]-5-methylpyridin-2-yl}acetamide A mixture of 3-[5-(2-chlorophenyl)-2-iodo-1,3-oxazol-4-yl]-4-{[2-(trimethylsilyl)-ethoxy]methyl}-4H-1,2,4-triazole (0.39 g, 0.78 mmol), N-[5-methyl-4-(4,4,5,5-tetramethyl-1,3,2-dioxaborolan-2-yl)pyridin-2-yl]acetamide (0.36 g, 1.32 mmol), tetrakis(triphenylphosphine)palladium(0) (0.18 g, 0.16 mmol) and cesium carbonate (1.64 g, 5.04 mmol) in dioxane (13 mL) and water (1.8 mL) was subjected to microwave irradiation at 150° C. for 60 min. The reaction mixture was concentrated and the residue was purified by column chromatography to give N-{4-[5-(2-chlorophenyl)-4-(4-{[2-(trimethylsilyl)ethoxy]methyl}-4H-1,2,4-triazol-3-yl)-1,3-oxazol-2-yl]-5-methylpyridin-2-yl}acetamide (0.33 g, 81%). LCMS (AA): m/z=525.1 (M+H).

Step 2: 4-[5-(2-chlorophenyl)-4-(4-{[2-(trimethylsilyl)ethoxy]methyl}-4H-1,2,4-triazol-3-yl)-1,3-oxazol-2-yl]-5-methylpyridin-2-amine A mixture of N-{4-[5-(2-chlorophenyl)-4-(4-{[2-(trimethylsilyl)ethoxy]methyl}-4H-1,2,4-triazol-3-yl)-1,3-oxazol-2-yl]-5-methylpyridin-2-yl}acetamide (0.42 g, 0.80 mmol), EtOH (25 mL) and aqueous NaOH (1M, 3 mL) was allowed to stir at reflux for 5 h. The reaction mixture was concentrated and the residue was washed with hexane. Diethyl ether was added and the mixture was filtered. The filtrate was concentrated to give 4-[5-(2-chlorophenyl)-4-(4-{[2-(trimethylsilyl)-ethoxy]methyl}-4H-1,2,4-triazol-3-yl)-1,3-oxazol-2-yl]-5-methylpyridin-2-amine (0.24 g, 62%) which was used in the next step without purification. LCMS (AA): m/z=483 (M+H).

Step 3: N-{4-[5-(2-chlorophenyl)-4-(4H-1,2,4-triazol-3-yl)-1,3-oxazol-2-yl]-5-methylpyridin-2-yl}cyclopropanecarboxamide (Compound I-77)

A mixture of 4-[5-(2-chlorophenyl)-4-(4-{[2-(trimethylsilyl)-ethoxy]methyl}-4H-1,2,4-triazol-3-yl)-1,3-oxazol-2-yl]-5-methylpyridin-2-amine (0.12 g, 0.25 mmol) and TEA (0.087 mL, 0.62 mmol) in DCM (2 mL) was allowed to stir at 0° C. for 20 min. To this mixture was added cyclopropanecarbonyl chloride (0.056 mL, 0.62 mmol). The reaction mixture was allowed to stir at 0° C. for 2 h and then MeOH (20 mL) was added. The mixture was allowed to stir at rt for 20 min and was then concentrated. MeOH (25 mL) and aqueous saturated NaHCO₃ (4 mL) were added to the residue and the mixture was allowed to stir at rt overnight before NaOH (1M, 3 mL) was added. The reaction mixture was allowed to stir rt for 3 h and then concentrated. EtOAc (30 mL) was added to the residue and the mixture was allowed to stir at rt for 30 min. The mixture was filtered and the filtrate was concentrated. DCM (5 mL) and TFA (2 mL) were added to the residue and the mixture was allowed to stir at rt overnight. The reaction mixture was concentrated and purified by column chromatography to give N-{4-[5-(2-chlorophenyl)-4-(4H-1,2,4-triazol-3-yl)-1,3-oxazol-2-yl]-5-methylpyridin-2-yl}cyclopropanecarboxamide (Compound I-77) (0.025 g, 24%). LCMS (AA): m/z=421 (M+H).

Example 11

N-{4-[5-(2-chlorophenyl)-4-(4H-1,2,4-triazol-3-yl)-1,3-oxazol-2-yl]pyridine-2-yl}propanamide (Compound I-75)

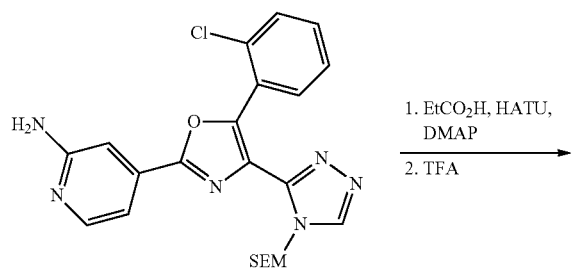

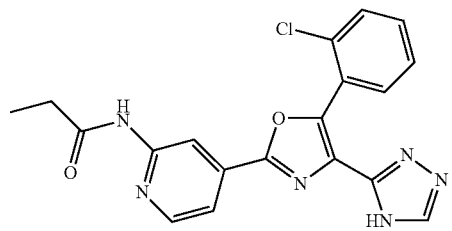

A mixture of propanoic acid (0.0095 mL, 0.13 mmol), HATU (0.019 g, 0.051 mmol) and N-methylmorpholine (0.014 mL, 0.13 mmol) in DCM (1 mL) was allowed to stir at rt for 30 min. Solid 4-[5-(2-chlorophenyl)-4-(4-{[2-(trimethylsilyl)ethoxy]methyl}-4H-1,2,4-triazol-3-yl)-1,3-oxazol-2-yl]pyridine-2-amine (0.020 g, 0.043 mmol) and DMAP (0.016 g, 0.13 mmol) were then added and the reaction mixture was allowed to stir at 80° C. overnight. The reaction mixture was allowed to cool to rt and was diluted with DCM (3 mL) and washed with saturated aqueous NaHCO₃ (2 mL). The organic solution was separated and the aqueous solution was extracted with DCM. The organic solutions were combined and concentrated. The residue was redissolved in DCM (0.5 mL) and to this solution was added TFA (0.5 mL). The reaction mixture was allowed to stir at rt for 12 h and then concentrated to dryness. The residue was purified by column chromatography to give N-{4-[5-(2-chlorophenyl)-4-(4H-1,2,4-triazol-3-yl)-1,3-oxazol-2-yl]pyridine-2-yl}propanamide (Compound I-75) (3.5 mg, 21%). LCMS (FA): m/z=395 (M+H). ¹H NMR (400 MHz, DMSO) δ 10.72 (s, 1H), 8.79 (s, 1H), 8.51 (d, J=5.2 Hz, 1H), 7.79 (d, J=7.6 Hz, 1H), 7.67 (dd, J=5.2, 1.5 Hz, 1H), 7.64 (dd, J=8.1, 1.2 Hz, 1H), 7.58 (td, J=7.7, 1.7 Hz, 1H), 7.50 (td, J=7.5, 1.3 Hz, 1H), 2.44 (q, J=7.5 Hz, 3H), 1.08 (t, J=7.5 Hz, 3H).

Compounds in the following table were prepared from the appropriate starting materials using the procedures described above:

| | |
|---|---|
| I-45 | LCMS (FA): m/z = 425.5 (M + H). |
| I-67 | LCMS (FA): m/z = 457.5 (M + H). |
| I-65 | LCMS (FA): m/z = 423.5 (M + H). |
| I-87 | LCMS (FA): m/z = 411.5 (M + H). |
| I-37 | LCMS (FA): m/z = 447.5 (M + H). |
| I-43 | LCMS (FA): m/z = 421.5 (M + H). |
| I-76 | LCMS (FA): m/z = 409.5 (M + H). |
| I-18 | LCMS (FA): m/z = 407.5 (M + H). |
| I-58 | LCMS (FA): m/z = 473 (M + H). |

Example 12

N-(4-{5-[3-(dimethylamino)piperidin-1-yl]-4-(4H-1,2,4-triazol-3-yl)-2-furyl}-5-methylpyridin-2-yl)acetamide (Compound I-26)

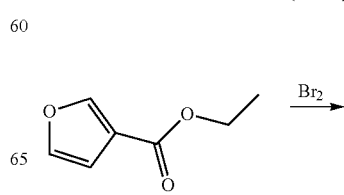

-continued

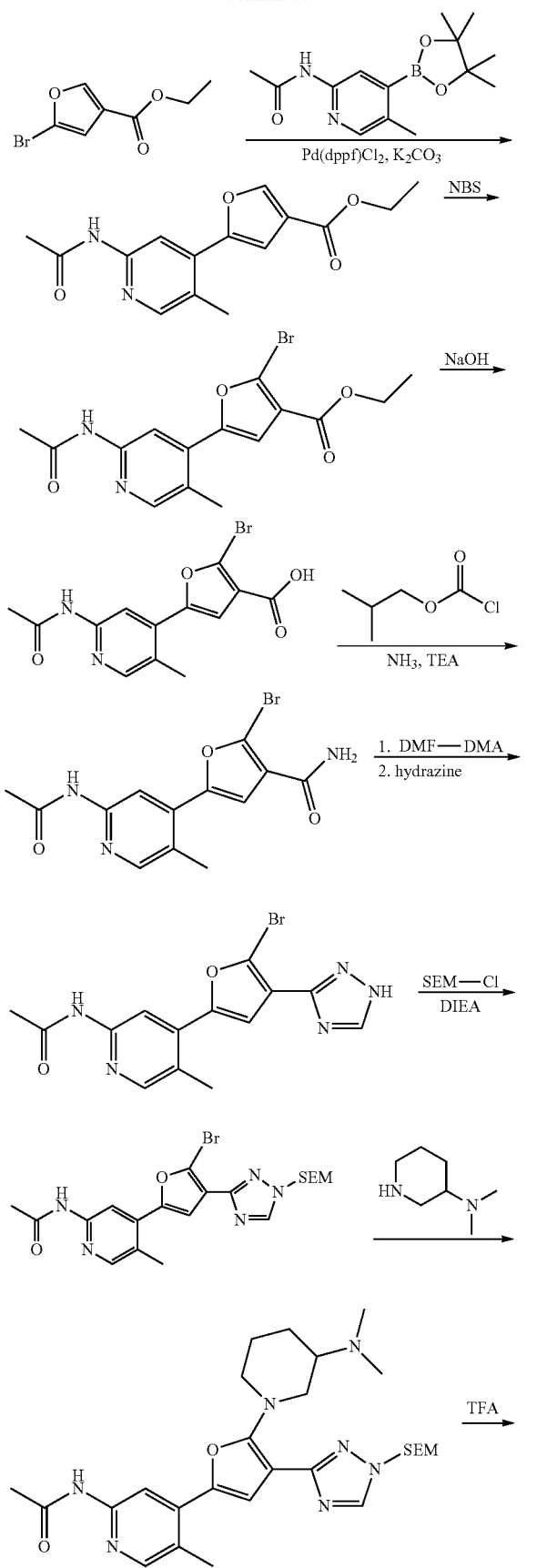

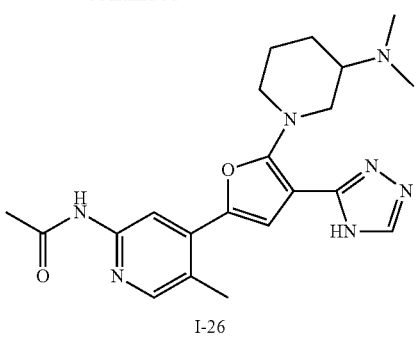

I-26

Step 1: ethyl 5-bromo-3-furoate

To a solution of ethyl 3-furoate (50.0 g, 360 mmol) in chloroform (380 mL) was added bromine (56.0 g, 360 mmol) in chloroform. The reaction mixture was allowed to stir at rt overnight and then poured into 10% aqueous $Na_2CO_3$. The mixture was extracted with DCM. The organic solutions were combined and washed with water until pH=7. The organic solution was concentrated and then distilled to give ethyl 5-bromo-3-furoate (42 g, 40%).

Step 2: ethyl 5-(2-acetamido-5-methylpyridin-4-yl)-3-furoate

A mixture of ethyl 5-bromo-3-furoate (23.7 g, 108.9 mmol), N-[5-methyl-4-(4,4,5,5-tetramethyl-1,3,2-dioxaborolan-2-yl)pyridine-2-yl]acetamide (20.0 g, 72.5 mmol), Pd(dppf)Cl$_2$ (5.92 g, 9.09 mmol) and K$_2$CO$_3$ (20.0 g, 72.5 mmol) in water (72.5 mL) and toluene (1240 mL) was allowed to stir at 100° C. under an atmosphere of nitrogen overnight. The mixture was filtered while hot and then concentrated. The residue was washed with EtOH and water and then dried to give ethyl 5-(2-acetamido-5-methylpyridin-4-yl)-3-furoate (20.0 g, 67%).

Step 3: ethyl 5-(2-acetamido-5-methylpyridin-4-yl)-2-bromo-3-furoate

To a solution of ethyl 5-(2-acetamido-5-methylpyridin-4-yl)-3-furoate (20.0 g, 69.9 mmol) in DMF (90 mL) was added NBS (29.6 g, 168.1 mmol). The reaction mixture was allowed to stir at 80° C. overnight and then concentrated. The residue was washed with EtOH and filtered to give ethyl 5-(2-acetamido-5-methylpyridin-4-yl)-2-bromo-3-furoate (20 g, 60%).

Step 4: 5-(2-acetamido-5-methylpyridin-4-yl)-2-bromo-3-furoic acid

A mixture of ethyl 5-(2-acetamido-5-methylpyridin-4-yl)-2-bromo-3-furoate (20 g, 54.6 mmol) in EtOH (240 mL) and 1M NaOH (80 mL) was allowed to stir at rt for 2 h. The reaction mixture was acidified with concentrated HCl to pH=3-4 and then filtered. The resulting solid was washed with water and dried to give 5-(2-acetamido-5-methylpyridin-4-yl)-2-bromo-3-furoic acid (10.0 g, 43%).

Step 5: 5-(2-acetamido-5-methylpyridin-4-yl)-2-bromo-3-furamide

To a solution of 5-(2-acetamido-5-methylpyridin-4-yl)-2-bromo-3-furoic acid (10.0 g, 29.6 mmol) in THF (950 mL) at −20° C. was added TEA (4.55 mL, 32.5 mmol) over 20 min. The reaction mixture was allowed to stir for 10 min after addition was complete and then isobutyl carbonochloridate (10.7 g, 88.8 mmol) was added over 10 min. The reaction mixture was allowed to stir for 20 min at −20° C. and was then allowed to warm to rt. A solution of $NH_3$ in THF was added and the reaction mixture was allowed to stir at rt overnight. The mixture was concentrated and the residue was diluted with water and filtered to give 5-(2-acetamido-5-methylpyridin-4-yl)-2-bromo-3-furamide (8.5 g, 85%).

Step 6: N-{4-[5-bromo-4-(1H-1,2,4-triazol-3-yl)-2-furyl]-5-methylpyridin-2-yl}acetamide To a suspension of 5-(2-acetamido-5-methylpyridin-4-yl)-2-bromo-3-furamide (8.5 g, 25.2 mmol) in dry toluene (260 mL) was added DMF-DMA (8.85 g, 74.0 mmol). The reaction mixture was allowed to stir at 50° C. overnight and then concentrated. The residue was resuspended in AcOH (90 mL) and hydrazine (3.77 g, 117.6 mmol) was added dropwise at rt. The reaction mixture was allowed to stir for 2 h and then concentrated. The mixture was azeotroped several times with toluene and then the residue was suspended in EtOAc and water. The mixture was basified with saturated aqueous $NaHCO_3$ to pH=8.5. The mixture was filtered and the solid was dried to give N-{4-[5-bromo-4-(1H-1,2,4-triazol-3-yl)-2-furyl]-5-methylpyridin-2-yl}acetamide (6.0 g, 66%).

Step 7: N-{4-[5-bromo-4-(1-{[2-(trimethylsilyl)ethoxy]methyl}-1H-1,2,4-triazol-3-yl)-2-furyl]-5-methylpyridin-2-yl}acetamide A solution of N-{4-[5-bromo-4-(1H-1,2,4-triazol-3-yl)-2-furyl]-5-methylpyridin-2-yl}acetamide (6.0 g, 16.6 mmol) in dry DMF (150 mL) was allowed to stir at 0° C. To this cooled solution was added DIEA (6.5 g, 5.0 mmol) portionwise over 20 min under an atmosphere of nitrogen. The reaction mixture was allowed to stir for 10 min at 0° C. and then SEM-Cl (5.5 g, 33.2 mmol) in dry DMF was add dropwise over 10 min. The reaction mixture was allowed to stir at 0° C. for 10 min and then allowed to warm to rt and allowed to stir for 3 h. The reaction mixture was diluted with water and extracted with EtOAc. The organic solutions were combined, washed with water and brine, dried over $Na_2SO_4$, filtered and concentrated. The residue was purified by column chromatography to give N-{4-[5-bromo-4-(1-{[2-(trimethylsilyl)ethoxy]methyl}-1H-1,2,4-triazol-3-yl)-2-furyl]-5-methylpyridin-2-yl}acetamide (1.1 g, 21%) plus an additional SEM regioisomer (1.7 g, 25%).

Step 8: N-(4-{5-[3-(dimethylamino)piperidin-1-yl]-4-(1-{[2-(trimethylsilyl)ethoxy]methyl}-1H-1,2,4-triazol-3-yl)-2-furyl}-5-methylpyridin-2-yl)acetamide To a solution of N-{-4-[5-bromo-4-(1-{[2-(trimethylsilyl)ethoxy]methyl}-1H-1,2,4-triazol-3-yl)-2-furyl]-5-methylpyridin-2-yl}acetamide (0.19 g, 0.38 mmol) in DMSO (3 mL) was added N,N-dimethylpiperidin-3-amine (0.25 g, 1.9 mmol). The mixture was allowed to stir at 120° C. for 48 h. The reaction mixture was diluted with EtOAc and washed with water. The organic solution was separated, dried over $MgSO_4$, filtered and concentrated. The residue was purified by column chromatography to give N-(4-{5-[3-(dimethylamino)piperidin-1-yl]-4-(1-{[2-(trimethylsilyl)ethoxy]methyl}-1H-1,2,4-triazol-3-yl)-2-furyl}-5-methylpyridin-2-yl)acetamide (0.15 g, 72%). LCMS (FA): m/z=540.7 (M+H).

Step 9: N-(4-{5-[3-(dimethylamino)piperidin-1-yl]-4-(4H-1,2,4-triazol-3-yl)-2-furyl}-5-methylpyridin-2-yl)acetamide (Compound I-26)

To a solution of N-(4-{5-[3-(dimethylamino)piperidin-1-yl]-4-(1-{[2-(trimethylsilyl)-ethoxy]methyl}-1H-1,2,4-triazol-3-yl)-2-furyl}-5-methylpyridin-2-yl)acetamide (0.15 g, 0.28 mmol) in DCM (5.0 mL) was added TFA (2 mL). The mixture was allowed to stir at rt overnight. The mixture was concentrated and the residue was purified by column chromatography to give N-(4-{5-[3-(dimethylamino)piperidin-1-yl]-4-(4H-1,2,4-triazol-3-yl)-2-furyl}-5-methylpyridin-2-yl)acetamide (Compound I-26) as the formate salt (0.095 g, 75%). LCMS (FA): m/z=410.6 (M+H).

Example 13

N-(4-{5-[2-chloro-5-(pyrrolidin-1-ylmethyl)phenyl]-4-(4H-1,2,4-triazol-3-yl)-2-furyl}-5-methylpyridin-2-yl)acetamide (Compound I-36)

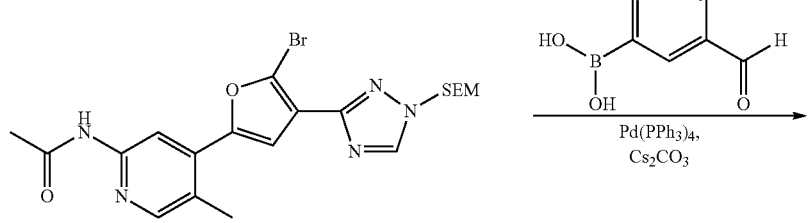

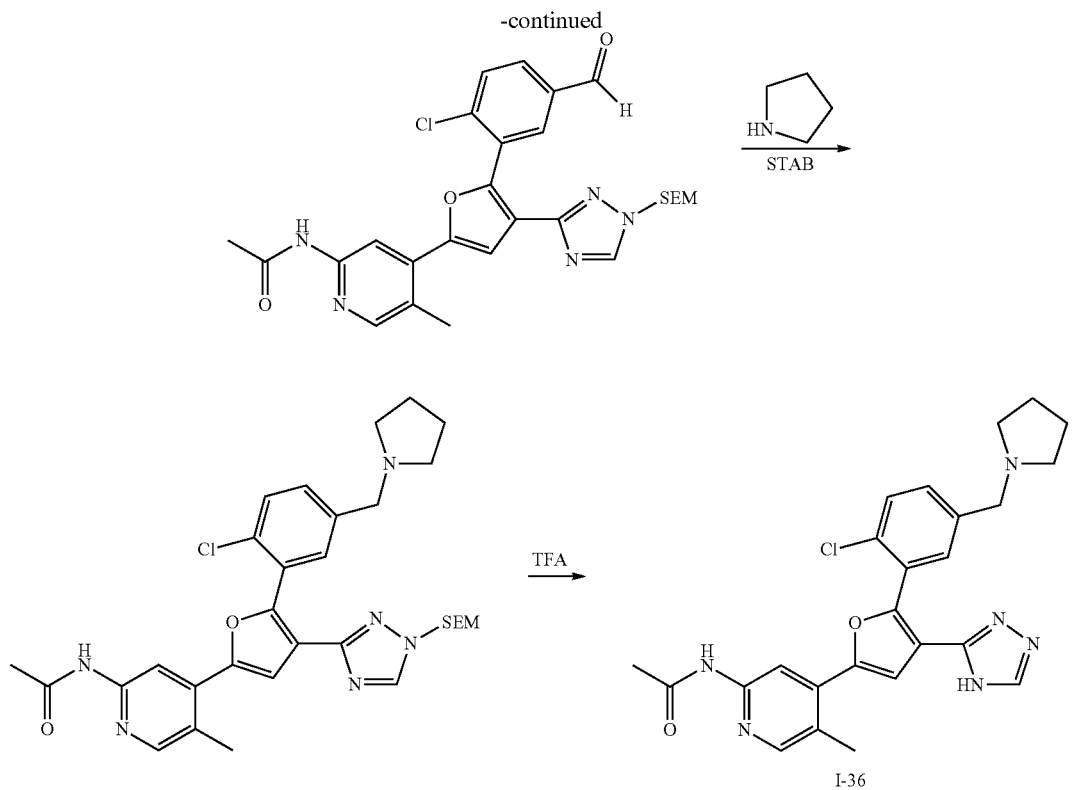

Step 1: N-{4-[5-(2-chloro-5-formylphenyl)-4-(1-{[2-(trimethylsilyl)ethoxy]methyl}-1H-1,2,4-triazol-3-yl)-2-furyl]-5-methylpyridin-2-yl}acetamide To a solution of N-{4-[5-bromo-4-(1-{[2-(trimethylsilyl)ethoxy]methyl}-1H-1,2,4-triazol-3-yl)-2-furyl]-5-methylpyridin-2-yl}acetamide (0.45 g, 0.91 mmol) in 1,4-dioxane (5 mL) was added water (1.2 mL), tetrakis(triphenylphosphine)palladium(0) (0.10 g, 0.091 mmol), (2-chloro-5-formylphenyl)boronic acid (0.22 g, 1.19 mmol) and cesium carbonate (0.89 g, 2.74 mmol). The mixture was allowed to stir and subjected to microwave irradiation at 150° C. for 20 min. The mixture was diluted with water and extracted with EtOAc. The organic solution was dried over MgSO$_4$, filtered and concentrated. The residue was purified by column chromatography to give N-{4-[5-(2-chloro-5-formylphenyl)-4-(1-{[2-(trimethylsilyl)ethoxy]methyl}-1H-1,2,4-triazol-3-yl)-2-furyl]-5-methylpyridin-2-yl}acetamide (0.42 g, 83%). LCMS (FA): m/z=552.6 (M+H).

Step 2: N-(4-{5-[2-chloro-5-(pyrrolidin-1-ylmethyl)phenyl]-4-(1-{[2-(trimethylsilyl)ethoxy]methyl}-1H-1,2,4-triazol-3-yl)-2-furyl}-5-methylpyridin-2-yl)acetamide To a solution of N-{4-[5-(2-chloro-5-formylphenyl)-4-(1-{[2-(trimethylsilyl)ethoxy]methyl}-1H-1,2,4-triazol-3-yl)-2-furyl]-5-methylpyridin-2-yl}acetamide (0.19 g, 0.34 mmol) in DCM (10 mL) was added pyrrolidine (0.14 mL, 1.68 mmol) and STAB (0.21 g, 1.01 mmol). The mixture was allowed to stir at rt overnight. The mixture was diluted with water and extracted with DCM. The organic solutions were combined, dried over MgSO$_4$, filtered and concentrated. The residue was purified by column chromatography to give N-(4-{5-[2-chloro-5-(pyrrolidin-1-ylmethyl)phenyl]-4-(1-{[2-(trimethylsilyl)ethoxy]methyl}-1H-1,2,4-triazol-3-yl)-2-furyl}-5-methylpyridin-2-yl)acetamide (0.20 g, 100%). LCMS (FA): m/z=607.7 (M+H).

Step 3: N-(4-{5-[2-chloro-5-(pyrrolidin-1-ylmethyl)phenyl]-4-(4H-1,2,4-triazol-3-yl)-2-furyl}-5-methylpyridin-2-yl)acetamide (Compound I-36)

To a solution of N-(4-{5-[2-chloro-5-(pyrrolidin-1-ylmethyl)phenyl]-4-(1-{[2-(trimethylsilyl)ethoxy]methyl}-1H-1,2,4-triazol-3-yl)-2-furyl}-5-methylpyridin-2-yl)acetamide (0.20 g, 0.34 mmol) in DCM (5 mL) was added TFA (2 mL). The mixture was allowed to stir at rt overnight. The mixture was concentrated and the residue was purified by column chromatography to give N-(4-{5-[2-chloro-5-(pyrrolidin-1-ylmethyl)phenyl]-4-(4H-1,2,4-triazol-3-yl)-2-furyl}-5-methylpyridin-2-yl)acetamide (0.14 g, 81%). LCMS (FA): m/z=477.6 (M+H).

Compounds in the following table were prepared from the appropriate starting materials using the procedures described above:

| | |
|---|---|
| I-23 | LCMS (FA): m/z = 394.6 (M + H). |
| I-16 | LCMS (FA): m/z = 478.0 (M + H). |
| I-7 | LCMS (FA): m/z = 451.6 (M + H). |
| I-40 | LCMS (FA): m/z = 452.7 (M + H). |

Example 14

N-{4-[4-(2-chlorophenyl)-5-(4H-1,2,4-triazol-3-yl)-1,3-oxazol-2-yl]-5-methylpyridin-2-yl}acetamide (Compound I-39)

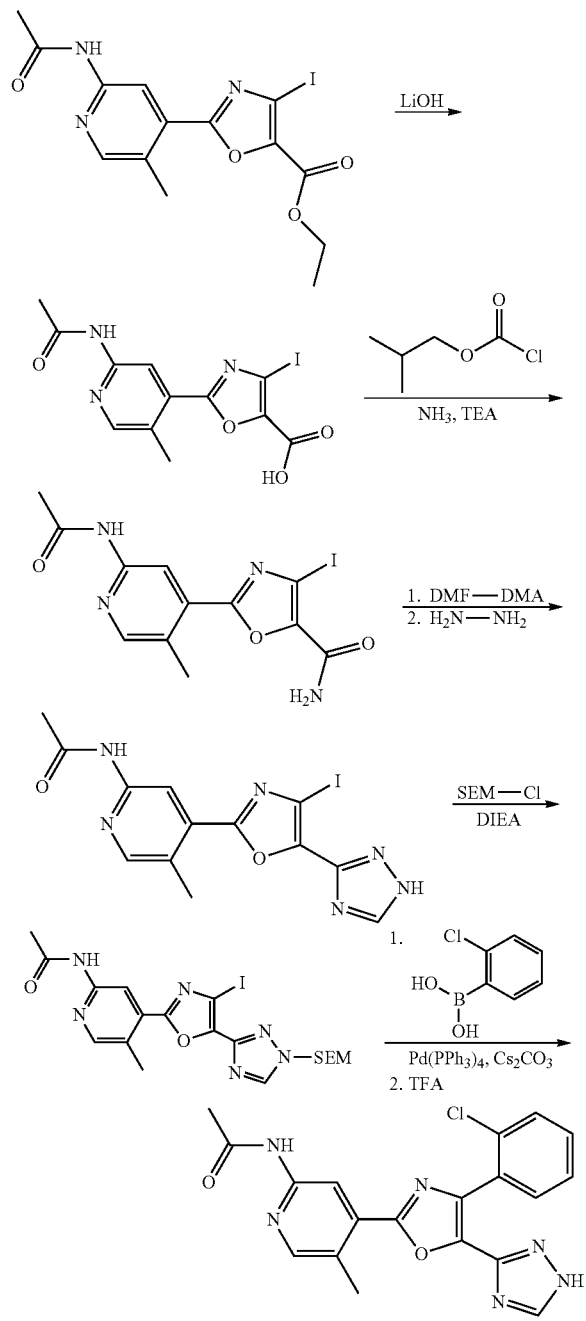

Step 1: 2-(2-acetamido-5-methylpyridin-4-yl)-4-iodo-1,3-oxazole-5-carboxylic acid To a solution of ethyl 2-(2-acetamido-5-methylpyridin-4-yl)-4-iodo-1,3-oxazole-5-carboxylate (33.0 g, 80.0 mmol) in THF (660 mL) was added an aqueous solution of LiOH (1M in water, 80 mL). The reaction mixture was allowed to stir for 5 h and then diluted with water. The organic solvent was removed by evaporation and the pH of the remaining aqueous solution was adjusted to 3-4. The mixture was filtered and the solid was collected, washed with water, and dried to give 2-(2-acetamido-5-methylpyridin-4-yl)-4-iodo-1,3-oxazole-5-carboxylic acid (25.0 g, 81%).

Step 2: 2-(2-acetamido-5-methylpyridin-4-yl)-4-iodo-1,3-oxazole-5-carboxamide To a suspension of 2-(2-acetamido-5-methylpyridin-4-yl)-4-iodo-1,3-oxazole-5-carboxylic acid (10.0 g, 26 mmol) in THF (200 mL) was added TEA (11.0 mL, 78.0 mmol). The reaction mixture was allowed to stir at rt for 1 h and then isobutyl carbonochloridate (10.0 mL, 74.0 mmol) was added. The reaction mixture was allowed to stir at rt for 5 hr and then saturated ammonia in THF (100 mL) was added. The reaction mixture was allowed to stir at rt for 30 min and was then diluted with water. The organic solvent was removed by evaporation and the slurry was filtered. The solid was collected, washed with water and dried to give 2-(2-acetamido-5-methylpyridin-4-yl)-4-iodo-1,3-oxazole-5-carboxamide (8.7 g, 87%).

Step 3: N-{4-[4-iodo-5-(1H-1,2,4-triazol-3-yl)-1,3-oxazol-2-yl]-5-methylpyridin-2-yl}acetamide To a slurry of 2-(2-acetamido-5-methylpyridin-4-yl)-4-iodo-1,3-oxazole-5-carboxamide (12.0 g, 31.0 mmol) in toluene (240 mL) was added DMF-DMA (24.0 mL, 187 mmol). The reaction mixture was allowed to stir at 90° C. for 5 h and then concentrated. The residue was suspended in AcOH (120 mL) and hydrazine hydrate (4.8 mL, 155 mmol) was added slowly. The reaction mixture was allowed to stir at rt overnight and then diluted with water. The slurry was filtered and the solid was collected, washed with water, and dried to give N-{4-[4-iodo-5-(1H-1,2,4-triazol-3-yl)-1,3-oxazol-2-yl]-5-methylpyridin-2-yl}acetamide (12.5 g, 95%).

Step 4: N-{4-[4-iodo-5-(1-{[2-(trimethylsilyl)ethoxy]methyl}-1H-1,2,4-triazol-3-yl)-1,3-oxazol-2-yl]-5-methylpyridin-2-yl}acetamide To a solution of N-{4-[4-iodo-5-(1H-1,2,4-triazol-3-yl)-1,3-oxazol-2-yl]-5-methylpyridin-2-yl}acetamide (6.2 g, 15 mmol) in DMF (60 mL) was added DIEA (4.0 mL, 23.0 mmol). The reaction mixture was allowed to stir at rt for 2 h and then SEM-Cl (4.1 mL, 23.0 mmol) was added. The reaction mixture was allowed to stir at rt overnight and then concentrated. The residue was purified by column chromatography to give N-{4-[4-iodo-5-(1-{[2-(trimethylsilyl)ethoxy]methyl}-1H-1,2,4-triazol-3-yl)-1,3-oxazol-2-yl]-5-methylpyridin-2-yl}acetamide (2.7 g) plus another SEM regioisomer (1.2 g).

Step 5: N-{4-[4-(2-chlorophenyl)-5-(4H-1,2,4-triazol-3-yl)-1,3-oxazol-2-yl]-5-methylpyridin-2-yl}acetamide (Compound I-39)

To a solution of N-{4-[4-iodo-5-(1-{[2-(trimethylsilyl)ethoxy]methyl}-1H-1,2,4-triazol-3-yl)-1,3-oxazol-2-yl]-5-methylpyridin-2-yl}acetamide (0.18 mg, 0.33 mmol) in 1,4-dioxane (3 mL) was added water (0.4 mL), (2-chlorophenyl)boronic acid (0.067 g, 0.43 mmol), tetrakis(triphenylphosphine) palladium(0) (0.038 g, 0.033 mmol) and cesium carbonate (0.32 mg, 0.99 mmol). The reaction mixture was allowed to stir and was subjected to microwave irradiation at 150° C. for 20 min. The mixture was diluted with water and extracted with EtOAc. The organic solutions were combined, dried over MgSO$_4$, filtered and concentrated. The residue was dissolved in DCM (5 mL) and to this solution was added TFA (2 mL). The reaction mixture was allowed to stir at rt overnight and was then concentrated. The residue was purified by column chromatography to give N-{4-[4-(2-chlorophenyl)-5-(4H-1,2,4-triazol-3-yl)-1,3-oxazol-2-yl]-5-methylpyridin-2-yl}acetamide (Compound I-39) (0.095 g, 73%). LCMS (FA): m/z=395.6 (M+H).

Example 15

N-{4-[4-(1,1-dioxidoisothiazolidin-2-yl)-5-(4H-1,2,4-triazol-3-yl)-1,3-oxazol-2-yl]-5-methylpyridin-2-yl}acetamide (Compound I-50)

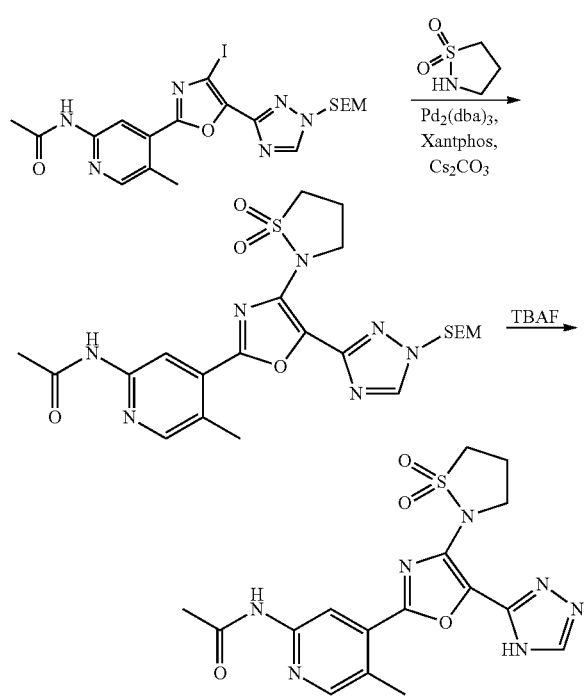

Step 1: N-{4-[4-(1,1-dioxidoisothiazolidin-2-yl)-5-(1-{[2-(trimethylsilyl)ethoxy]methyl}-1H-1,2,4-triazol-3-yl)-1,3-oxazol-2-yl]-5-methylpyridin-2-yl}acetamide To a solution of N-{4-[4-iodo-5-(1-{[2-(trimethylsilyl)ethoxy]methyl}-1H-1,2,4-triazol-3-yl)-1,3-oxazol-2-yl]-5-methylpyridin-2-yl}acetamide (0.33 g, 0.601 mmol) in 1,4-dioxane (4 mL) was added tris(dibenzylideneacetone)dipalladium(0) (0.055 g, 0.060 mmol), Xantphos (0.10 g, 0.18 mmol), isothiazolidine 1,1-dioxide (0.36 g, 3.01 mmol) and cesium carbonate (0.98 g, 3.00 mmol). The mixture was degassed with nitrogen and then subjected to microwave irradiation at 140° C. for 2.5 h. The mixture was diluted with water and extracted with EtOAc. The organic solutions were combined, dried over MgSO$_4$, filtered and concentrated. The residue was purified by column chromatography to give N-{4-[4-(1,1-dioxidoisothiazolidin-2-yl)-5-(1-{[2-(trimethylsilyl)ethoxy]methyl}-1H-1,2,4-triazol-3-yl)-1,3-oxazol-2-yl]-5-methylpyridin-2-yl}acetamide which was used directly in the next step. LCMS (FA): m/z=534.6 (M+H).

Step 2: N-{4-[4-(1,1-dioxidoisothiazolidin-2-yl)-5-(4H-1,2,4-triazol-3-yl)-1,3-oxazol-2-yl]-5-methylpyridin-2-yl}acetamide (Compound I-50)

To a solution of N-{4-[4-(1,1-dioxidoisothiazolidin-2-yl)-5-(1-{[2-(trimethylsilyl)ethoxy]methyl}-1H-1,2,4-triazol-3-yl)-1,3-oxazol-2-yl]-5-methylpyridin-2-yl}acetamide (from the previous step) in THF (10 mL) was added TBAF in THF (1M, 3.3 mL). The reaction mixture was allowed to stir at rt overnight. The mixture was concentrated to dryness and then diluted with EtOAc. The mixture was washed with water. The organic solution was dried over MgSO$_4$, filtered and concentrated. The residue was purified by column chromatography to give N-{4-[4-(1,1-dioxidoisothiazolidin-2-yl)-5-(4H-1,2,4-triazol-3-yl)-1,3-oxazol-2-yl]-5-methylpyridin-2-yl}acetamide (Compound I-50) (0.028 g, 12%). LCMS (FA): m/z=404.6 (M+H).

Compounds in the following table were prepared from the appropriate starting materials using the procedures described above:

| | |
|---|---|
| I-17 | LCMS (FA): m/z = 403.6 (M + H). |
| I-79 | LCMS (FA): m/z = 411.6 (M + H). |

Biological Data:
VPS34 Enzyme Assays
Cloning, Expression, and Purification of PI3Ks
VPS34 (accession number GB:BC033004) was cloned into pDEST20-Thrombin as N-terminal GST tagged fusion proteins using the Gateway system (Invitrogen, catalog#11804-013). The sequences were verified before recombinant protein expression using the Baculovirus Expression System with Gateway® Technology.

For expression VPS34 was infected at 1MOI in SF9 cells and harvested 72 hours post infection.

For purification, VPS34 is purified by Glutathione Sepharose 4 Fast Flow (GE Healthcare #17-5132-03) followed by HiTrap Q (GE Healthcare #17-1153-01).

VPS34 Assay Conditions
Human VPS34 Enzyme Assay Method
100 nL compounds in DMSO are added to wells of a 384 well microtitre plate (Greiner 780076). At room temperature: 5 ul VPS34 reaction buffer (Invitrogen Assay Buffer Q (diluted 1 in 5 with nanopure water) plus 2 mM DTT and 2 mM MnCl$_2$) containing ATP (20 uM, Promega) and 200 uM PI-PS substrate (Invitrogen PV5122) is added followed immediately by 5 ul VPS34 reaction buffer (as above) containing VPS34 (5 nM, Millennium Protein Sciences Group) and the mixture is incubated with shaking at room temperature for 1 hour. Then 5 ul VPS34 stop-detect mix (as per Invitrogen Adapta Assay kit (PV5009) instructions (contains kinase quench buffer, TR-FRET buffer, Adapta Eu anti-ADP antibody and Alexa Fluor 647 ADP tracer)) is added to quench the reaction. The plates are then incubated for 30 minutes at room temperature with shaking and then read on a BMG PheraStar Plus reader.

Vps34 Cell Assays
1) FYVE Domain Redistribution Assay
The FYVE domain redistribution assay monitors translocation of EGFP-2XFYVE from its initial location bound to (PtdIns(3)P) in early endosomes to the cytoplasm in response to test compounds. Recombinant U2OS cells stable expressing the FYVE finger from the human homologue of the hepatocyte growth factor-regulated tyrosine kinase substrate Hrs, duplicated in tanden (GenBank Acc. NM 004712) and fused to the C-terminus of enhanced green fluorescent protein (EGFP). U2OS cells are adherent epithelial cells derived from human osteosarcoma. Expression of EGFP-2X-FYVE is controlled by a standard CMV promoter and continuous expression is maintained by addition of geneticin to the culture medium. Localization of the fusion protein within the cells is imaged on the Evotec Technologies OPERA Confocal Imager and Integrated Spot Signal Per Cellular Signal is quantified using Acapella software. Using this information, IC50 values for inhibitors can be determined.

U2OS EGFP-2XFYVE cells are propagated in Dulbecco's Modified Eagle Media High glucose(D-MEM) (Invitrogen cat. 11995) containing 10% Fetal Bovine Serum (HyClone cat. SH30071.02) and 0.5 mg/ml Geneticin (Invitrogen) and kept in a humidified chamber at 37° C. with 5% $CO_2$. $8 \times 10^3$ cells are cultured in 100 µl of media per well in tissue culture-treated black-walled, clear bottom Optilux 96-well plates (BD Biosciences) for 16-24 hours.

Prior to addition of compounds, cell media is removed and replaced with 75 µl of fresh media. Test compounds in DMSO are diluted 1:100 in media. The diluted test compounds are added to the cells (25 µl per well) in 3-fold dilutions with a final concentration range of 0.0015 to 10 µM. The cells are incubated for 30 minutes in a humidified chamber at 37° C. with 5% $CO_2$. Immediately following compound incubation, all liquid is removed from the wells and cells are fixed with 4% paraformaldehyde in PBS (75 µl per well) for 15 minutes at room temperature. The paraformaldehyde solution is removed from wells and washed once with PBS (100 µl per well). The PBS is removed and cells are incubated with DRAQ5 Nucleur Dye (Alexis/Biostatus) (85 µl per well). The plates are covered with Flash Plate plastic adhesive foil and imaged on the Evotec Technologies OPERA Confocal Imager Opera after at least a 30 minute incubation. Concentration curves are generated by calculating the Integrated Spot Intensity Per Cellular Signal decrease in test-compound treated samples relative to DMSO-treated controls and a 100% control inhibitor.

PI3K Enzyme Assays

Cloning, Expression, and Purification of PI3Ks

The catalytic subunits of PI3Ks are cloned into either pDEST8(p110 alpha) or pDEST10(p110beta, p110delta, and p110gamma) as N-terminal His tagged fusion proteins using the Gateway system (Invitrogen, catalog#11804-010 for pDEST8 and 11806-015 for pDEST10). The sequences are verified before recombinant protein expression using the Baculovirus Expression System with Gateway® Technology. The accession numbers for the subunits are as follows:
p110alpha (GB:U79143)
p110beta (GB:S67334)
p110delta (GB: U86453)
p110gamma (GB:X83368)

The regulatory subunits of PI3Ks are cloned into pDEST8 as un-tagged protein using the Gateway system (Catalog#11804-010). The sequences are verified before recombinant protein expression using the Baculovirus Expression System with Gateway® Technology. The accession numbers for the subunits are as following:
p85 alpha (GB: BC030815)
p101(GB: AB028925)
VPS34 is cloned into pDEST20-Thombin as N-terminal GST tagged fusion proteins using the Gateway system (Invitrogen, catalog#11804-013). The sequences are verified before recombinant protein expression using the Baculovirus Expression System with Gateway® Technology.

For expression of the p110 complexes, the p85 (MOI of 4) is co-infected with p110 alpha, beta, and delta respectively (1MOI) in SF9 cells and harvested at 60 hours post co-infection. P110 gamma was infected at 1 MOI and harvested at 60 hours post infection.

For purification, PI3Ks are purified by Ni-NTA Agarose (Qiagen #30250) followed by Mono Q 10/100 GL (Ge Healthcare #17-5167-01). VPS34 is purified by Glutathione Sepharose 4 Fast Flow (GE Healthcare #17-5132-03) followed by HiTrap Q (GE Healthcare #17-1153-01).

PI3K Assay Conditions

1) Human PI3Kα Enzyme Assay Method 0.5 uL compounds in DMSO are added to wells of a 384 well microtitre plate (Corning 3575). At room temperature: 10 ul PI3K reaction buffer (50 mM Hepes, 5 mM DTT, 150 mM NaCl, 10 mM beta-glycerophosphate, 10 mM MgCl2, 0.25 mM sodium cholate and 0.001% CHAPS, pH 7.00) containing ATP (25 uM, Promega) is added followed immediately by 10 ul PI3K reaction buffer containing di-C8 PI(4,5)P2 (3.5 uM, CellSignals) and PI3Kalpha (0.4875 nM, Millennium Protein Sciences Group) and the mixture is incubated with shaking at room temperature for 30 minutes. Then 5 ul PI3K stop mix (50 mM Hepes, 5 mM DTT, 150 mM NaCl, 0.01% Tween-20, 15 mM EDTA and 25 nM biotin-PI (3,4,5)P3 (Echelon) is added to quench the reaction followed immediately by addition of 5 ul HTRF detection mix (50 mM Hepes, 5 mM DTT, 150 mM NaCl, 0.01% Tween-20, 40 mM KF, 1.0 nM GST:GRP-1 PH domain (Millennium Protein Sciences Group), 15 nM Streptavidin-XL (CisBio) and 0.375 nM anti-GST Eu++ antibody (CisBio) at pH 7.00). The plates are then incubated for 1 hour at room temperature with shaking and then read on a BMG PheraStar Plus reader.

2) Human PI3K beta, delta and gamma isoforms are tested using the procedure described for PI3K alpha above but with the following changes: PI3K beta (5.25 nM), PI3K delta (0.75 nM) and PI3K gamma (5 nM). All isoforms supplied by Millennium Protein Science Group.

3) VPS34 is assayed using Adapta™ Universal Kinase Assay Kit (Invitrogen).

PI3K Cell Assays

1) In-Cell Western Assay

The pSer473 AKT LI-COR In-Cell Western Assay is a quantitative immunofluorescent assay that measures phosphorylation of serine 473 AKT (pSer473 AKT) in WM266.4 and SKOV3 tumor cell lines grown in cell culture.

WM266.4 cells are propagated in Minimum Essential Media (MEM) (Invitrogen) containing L-glutamine, 10% Fetal Bovine Serum, 1 mM MEM Sodium Pyruvate, and 0.1 mM MEM Non-Essential Amino Acids and SKOV3 cells are propagated in McCoy's 5A Media (modified) (Invitrogen) containing L-Glutamine and 10% Fetal Bovine Serum. Both cell lines are kept in a humidified chamber at 37° C. with 5% $CO_2$. For the pSer473 AKT LI-COR In-Cell Western Assay, $1.5 \times 10^4$ WM266.4 and $1.5 \times 10^4$ SKOV3 cells are cultured in 100 µl of media per well in tissue culture-treated black-walled, clear bottom Optilux 96-well plates (BD Biosciences) for 16-20 hours. Prior to addition of compounds, cell media is removed and replaced with 75 µl of fresh media. Test compounds in DMSO are diluted 1:100 in media. The diluted test compounds are added to the cells (25 µl per well) in 3-fold dilutions with a final concentration range of 0.0015 to 10 µM. The cells are incubated for 2 hours in a humidified chamber at 37° C. with 5% $CO_2$. Immediately following compound incubation, all liquid is removed from the wells and cells are fixed with 4% paraformaldehyde in PBS (150 µl per well) for 20 minutes at room temperature. The paraformaldehyde solution is removed from wells and the cells are permeabilized with 200 μl 0.1% Triton X-100 in PBS per well for 10 min×3 at room temperature. After removal of PBS+ 0.1% Triton X-100, 150 μl Odyssey blocking buffer (LI-COR Biosciences) is added to each well and plates are incubated at room temperature for 1.5 h. Blocking buffer is removed from the wells and primary antibodies (Phospho-AKT (Ser473) (D9E) XP™ Rabbit mAb and AKT (pan) (40D4) Mouse mAb, Cell Signaling Technology) diluted in Odyssey blocking buffer are added (50 μl per well). Plates are incubated at 4° C. overnight. The cells are washed for 20 min×3 with PBS+ 0.1% Tween-20 (200 μl per well). Secondary antibodies (IRDye 680 Goat anti-Rabbit IgG (H+L) and IRDye 800CW Goat anti-Mouse IgG (H+L), LI-COR Biosciences) are diluted in Odyssey blocking buffer and added to wells (50 per well) followed by a 1 h incubation at room temperature, protected from light. Cells are washed for 20 min×3 with PBS+0.1% Tween-20 (200 μl per well). Wash buffer is completely removed from wells after last wash, plates are protected from light until scanned and analyzed with the Odyssey Infrared Imaging System (LI-COR Biosciences). Both pS473 AKT and AKT are simultaneously visualized with the 680 nm fluorophore indicated by a red color and the 800 nm fluorophore indicated by a green color. Relative fluorescence units derived from the scans allow for quantitative analyses of both labeled proteins and the ratio of pS473 AKT to AKT is calculated. Concentration response curves are generated by plotting the average ratios of PI3K inhibitor-treated samples relative to DMSO-treated controls to determine percent change in expression of pS473 AKT.

2) ATPlite Viability Assay

The ATPLite™ Assay (Perkin-Elmer) measures cellular adenosine-triphosphate (ATP) through the generation of a luminescent signal formed from the ATP-dependent enzyme firefly luciferase. The luminescent signal intensity can be used as a measure of cellular proliferation, and can be used to assess the anti-proliferative effects of PI3K inhibitors.

WM266.4 cells propagated in Minimum Essential Media (MEM) (Invitrogen) containing L-Glutamine, 10% Fetal Bovine Serum, 1 mM MEM Sodium Pyruvate, and 0.1 mM MEM Non-Essential Amino Acids are cultured in 384-well tissue culture-treated Black/Clear plates (Falcon) at $1\times10^3$ cells per well in a volume of 75 μl in a humidified chamber at 37° C. with 5% $CO_2$ for 24 h. Test compounds (2 μl in 100% DMSO) are diluted in 95 μl of cell culture media. The diluted test compounds are added (8 μl per well) to 384-well plates. Final concentration range of 3-fold serial dilution of compounds is 0.001 to 20 μM. Plates are incubated for 72 h in a humidified chamber at 37° C. with 5% $CO_2$. One control plate without compound addition is processed at the start of the 72 h incubation as a "Time Zero" reading for quantitative evaluation of cell viability at start of assay. After 72 h, all but 25 μl of cell culture media is removed from each well, followed by the addition of 25 μl of ATPlite 1 step reagent (Perkin Elmer) to each well. Luminescence is measured on a LEADSeeker Luminescence Counter (GE Healthcare Life Sciences). Concentration response curves are generated by calculating the luminescence decrease in test compound-treated samples relative to DMSO-treated controls, and growth inhibition ($IC_{50}$) values are determined from the curves.

Table 3 below depicts % inhibition of VPS34 for compounds of the invention:

| I-number | Average VPS34 % INH @ 1.111 μM |
|---|---|
| I-54 | 152 |
| I-7 | 147 |
| I-69 | 144 |
| I-42 | 117 |
| I-56 | 139 |
| I-23 | 139 |
| I-57 | 135 |
| I-66 | 131 |
| I-27 | 133 |
| I-10 | 132 |
| I-16 | 131 |
| I-83 | 130 |
| I-48 | 130 |
| I-34 | 128 |
| I-36 | 129 |
| I-26 | 129 |
| I-3 | 112 |
| I-24 | 102 |
| I-39 | 125 |
| I-17 | 127 |
| I-2 | 124 |
| I-88 | 114 |
| I-15 | 103 |
| I-51 | 131 |
| I-44 | 150 |
| I-1 | 120 |
| I-60 | 122 |
| I-53 | 104 |
| I-81 | 112 |
| I-80 | 92 |
| I-29 | 116 |
| I-77 | 120 |
| I-18 | 120 |
| I-28 | 81 |
| I-5 | 108 |
| I-52 | 117 |
| I-22 | 110 |
| I-86 | 117 |
| I-37 | 117 |
| I-35 | 117 |
| I-41 | 90 |
| I-73 | 115 |
| I-50 | 115 |
| I-40 | 115 |
| I-68 | 104 |
| I-30 | 114 |
| I-33 | 102 |
| I-75 | 114 |
| I-61 | 96 |
| I-14 | 88 |
| I-72 | 78 |
| I-43 | 98 |
| I-46 | 89 |
| I-4 | 118 |
| I-9 | 64 |
| I-87 | 109 |
| I-6 | 99 |
| I-45 | 104 |
| I-76 | 79 |
| I-59 | 101 |
| I-64 | 64 |
| I-78 | 43 |
| I-13 | 95 |
| I-58 | 94 |
| I-85 | 56 |
| I-12 | 61 |
| I-71 | 87 |
| I-70 | 45 |
| I-84 | 54 |
| I-79 | 82 |
| I-19 | 48 |
| I-62 | 51 |
| I-38 | 43 |
| I-31 | 56 |
| I-25 | 41 |
| I-20 | 37 |
| I-82 | 68 |
| I-47 | 31 |
| I-21 | 25 |
| I-11 | 22 |

-continued

| I-number | Average VPS34 % INH @ 1.111 μM |
|---|---|
| I-32 | 26 |
| I-74 | 28 |
| I-65 | 21 |
| I-55 | 20 |
| I-49 | 19 |
| I-67 | 39 |
| I-63 | 14 |
| I-8 | 7 |

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

The invention claimed is:

1. A compound of formula IB:

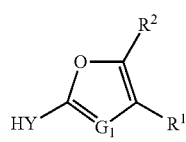

or a pharmaceutically acceptable salt thereof, wherein:
  $G_1$ is N or $CR^3$, wherein $R^3$ is H, —CN, halogen, —Z—$R^5$, $C_{1-6}$ aliphatic, or 3-10-membered cycloaliphatic, wherein:
    Z is selected from an optionally substituted $C_{1-3}$ alkylene chain, —O—, —N($R^{3a}$)—, —S—, —S(O)—, —S(O)$_2$—, —C(O)—, —CO$_2$—, —C(O)N$R^{3a}$-, —N($R^{3a}$)C(O)—, —N($R^{3a}$)CO$_2$—, —S(O)$_2$N$R^{3a}$-, —N($R^{3a}$)S(O)$_2$—, —OC(O)N($R^{3a}$)—, —N($R^{3a}$)C(O)N$R^{3a}$-, —N($R^{3a}$)S(O)$_2$N($R^{3a}$)—, and —OC(O)—;
    $R^{3a}$ is hydrogen or an optionally substituted $C_{1-4}$ aliphatic, and
    $R^5$ is an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;
  $R^1$ is CY, CN, —CON($R^4$)$_2$, —COO$R^4$, —C(O)CH$_3$, —NHCO$R^4$, —NHSO$_2R^4$, —NHCON($R^4$)$_2$, —NHCOO$R^4$, —NHSO$_2$N($R^4$)$_2$, —CONHOH, —CH$_2$OH, —CH$_2$NH$_2$, —CH$_2$NHCOCH$_3$, —SO$_2$NH$_2$, —CONH=NHNH$_2$, or —NHSO$_2$O$R^4$, wherein CY is group selected from a 3-7-membered substituted cycloaliphatic or optionally substituted heterocyclic group, a substituted phenyl group, and a 5-6-membered optionally substituted heteroaryl group; wherein:
    $R^4$ is H, —Z$_2$—$R^6$, optionally substituted $C_{1-6}$ aliphatic, 6-10-membered aryl, or 5-10-membered heteroaryl having 1-5 heteroatoms independently selected from nitrogen, oxygen, and sulfur or optionally substituted 3-10-membered cycloaliphatic, wherein:
      $Z_2$ is selected from an optionally substituted $C_{1-3}$ alkylene chain, —S(O)—, —S(O)$_2$—, —C(O)—, —CO$_2$—, —C(O)N$R^{4a}$-, S(O)$_2$N$R^{4a}$-, and —(CH$_2$)$_q$O(CH$_2$)$_q$—;
    $R^{4a}$ is hydrogen or an optionally substituted $C_{1-4}$ aliphatic, and
    $R^6$ is an optionally substituted group selected from $C_{1-6}$ aliphatic, —O$R^{4a}$, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;
    q is 0 to 3;
  $R^2$ is a substituted monocyclic group selected from 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur, wherein $R^2$ is substituted with 1-4 occurrences of $R^{2a}$, wherein each occurrence of $R^{2a}$ is independently —$R^{12a}$, -$T_2$-$R^{12d}$, -$T_2$-$R^{12a}$, or —$V_2$-$T_2$-$R^{12d}$, and:
    each occurrence of $R^{12a}$ is independently halogen, —CN, —NO$_2$, —$R^{12c}$, —N($R^{12b}$)$_2$, —O$R^{12b}$, —S$R^{12c}$, —S(O)$_2R^{12c}$, —C(O)$R^{12b}$, —C(O)O$R^{12b}$, —C(O)N($R^{12b}$)$_2$, —S(O)$_2$N($R^{12b}$)$_2$, —OC(O)N($R^{12b}$)$_2$, —N($R^{12e}$)C(O)$R^{12b}$, —N($R^{12e}$)SO$_2R^{12c}$, —N($R^{12e}$)C(O)O$R^{12b}$, —N($R^{12e}$)C(O)N($R^{12b}$)$_2$, or —N($R^{12e}$)SO$_2$N($R^{12}$)$_2$;
    each occurrence of $R^{12b}$ is independently hydrogen or an optionally substituted group selected from $C_1$-$C_6$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;
    or two occurrences of $R^{12b}$, taken together with a nitrogen atom to which they are bound, form an optionally substituted 4-7-membered heterocyclyl ring having 0-1 additional heteroatoms selected from nitrogen, oxygen, and sulfur;
    each occurrence of $R^{12c}$ is independently an optionally substituted group selected from $C_1$-$C_6$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;
    each occurrence of $R^{12d}$ is independently hydrogen or an optionally substituted from 3-10-membered cycloaliphatic, 4-10-membered heterocyclyl having 1-5 heteroatoms independently selected from nitrogen, oxygen, and sulfur, 6-10-membered aryl, or 5-10-membered heteroaryl having 1-5 heteroatoms independently selected from nitrogen, oxygen, and sulfur;
    each occurrence of $R^{12e}$ is independently hydrogen or an optionally substituted $C_{1-6}$ aliphatic group;
    each occurrence of $V_2$ is independently —N($R^{12e}$)—, —O—, —S—, —S(O)—, —S(O)$_2$—, —C(O)—, —C(O)O—, —C(O)N($R^{12e}$)—, —S(O)$_2$N($R^{12e}$)—, —OC(O)N($R^{12e}$)—, —N($R^{12e}$)C(O)—, —N($R^{12e}$)SO$_2$—, —N($R^{12e}$)C(O)O—, —N($R^{12e}$)C(O)N($R^{12e}$)—, —N($R^{12e}$)SO$_2$N($R^{12e}$)—, —OC(O)—, or —C(O)N($R^{12e}$)—O—; and
  $T_2$ is an optionally substituted $C_1$-$C_6$alkylene chain wherein the alkylene chain optionally is interrupted by —N($R^{13}$)—, —O—, —S—, —S(O)—, —S(O)$_2$—, —C(O)—, —C(O)O—, —C(O)N($R^{13}$)—, —S(O)$_2$N($R^{13}$)—, —OC(O)N($R^{13}$)—, —N($R^{13}$)C(O)—, —N($R^{13}$)SO$_2$—, —N($R^{13}$)C(O)O—, —N($R^{13}$)C(O)N($R^{13}$)—, —N($R^{13}$)S(O)$_2$N($R^{13}$)—, —OC(O)—, or —C(O)N($R^{13}$)—O— or wherein $T_2$ or a portion thereof optionally forms part of an optionally substituted 3-7 membered cycloaliphatic or heterocyclyl ring, wherein $R^{13}$ is hydrogen or an optionally substituted $C_{1-4}$ aliphatic group;

and

HY is a group selected from:

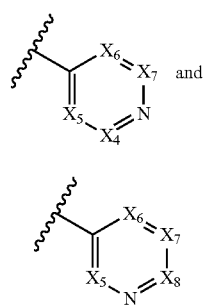

A

B wherein each occurrence of $X_4$, $X_5$, $X_6$, $X_7$, and $X_8$ is independently —$CR^{10}$ or N, provided no more than two occurrences of $X_4$, $X_5$, $X_6$, $X_7$, and $X_8$ are N;
or wherein two adjacent occurrences of $X_4$ and $X_5$, $X_6$, and $X_7$, or $X_7$, and $X_8$, together with the atom to which they are bound, form an optionally substituted fused group selected from phenyl and 5-6-membered heteroaryl having 1-5 heteroatoms independently selected from nitrogen, oxygen, and sulfur;

wherein $R^{10}$ is —$R^{10b}$, —$V_1$—$R^{10c}$, —$T_1$—$R^{10b}$, or —$V_1$—$T_1$—$R^{10b}$ wherein:

$V_1$ is —$NR^{11}$—, —$NR^{11}$—C(O)—, —$NR^{11}$—C(S)—, —$NR^{11}$—C($NR^{11}$)—, —$NR^{11}$C(O)O$R^{10a}$-, —$NR^{11}$C(O)$NR^{11}$—, —$NR^{11}$C(O)S$R^{10a}$-, —$NR^{11}$C(S)O$R^{10a}$-, —$NR^{11}$C(S)$NR^{11}$—, —$NR^{11}$C(S)S$R^{10a}$-, —$NR^{11}$C($NR^{11}$)O$R^{10a}$-, —$NR^{11}$C($NR^{11}$)$NR^{11}$—, —$NR^{11}$S(O)—, —$NR^{11}$S(O)$_2$—, —$NR^{11}$S(O)$_2$$NR^{11}$—, —C(O)—, —CO$_2$—, —C(O)$NR^{11}$—, —C(O)$NR^{11}$O—, —SO$_2$—, or —SO$_2$$NR^{11}$—;

each occurrence of $R^{10a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

$T_1$ is an optionally substituted $C_1$-$C_6$ alkylene chain wherein the alkylene chain optionally is interrupted by —N($R^{11}$)—, —O—, —S—, —S(O)—, —S(O)$_2$—, —C(O)—, —C(O)O—, —C(O)N($R^{11}$)—, —S(O)$_2$N($R^{11}$)—, —OC(O)N($R^{11}$)—, —N($R^{11}$)C(O)—, —N($R^{11}$)SO$_2$—, —N($R^{11a}$)C(O)O—, —N$R^{10a}$C(O)N($R^{10a}$)—, —N($R^{10a}$)S(O)$_2$N($R^{10a}$)—, —OC(O)—, or —C(O)N($R^{11}$)—O— or wherein $T_1$ forms part of an optionally substituted 3-7 membered cycloaliphatic or heterocyclyl ring;

each occurrence of $R^{10b}$ is independently hydrogen, halogen, —CN, —NO$_2$, —N($R^{11}$)$_2$, —O$R^{10a}$, —S$R^{10a}$, —S(O)$_2$$R^{10a}$, —C(O)$R^{10a}$, —C(O)O$R^{10a}$, —C(O)N($R^{11}$)$_2$, —S(O)$_2$N($R^{11}$)$_2$, —OC(O)N($R^{11}$)$_2$, —N($R^{11}$)C(O)$R^{10a}$, —N($R^{11}$)SO$_2$$R^{10a}$, —N($R^{11}$)C(O)O$R^{10a}$, —N($R^{11}$)C(O)N($R^{11}$)$_2$, or —N($R^{11}$)SO$_2$N($R^{11}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, or 5-10-membered heteroaryl having 1-5 heteroatoms independently selected from nitrogen, oxygen, and sulfur;

each occurrence of $R^{10c}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur, or $R^{10a}$ and $R^{10c}$ taken together with a nitrogen atom to which they are bound form an optionally substituted 4-7-membered heterocyclyl ring having 0-1 additional heteroatoms independently selected from nitrogen, oxygen, and sulfur;

each occurrence of $R^{11}$ is independently hydrogen, —C(O)$R^{11a}$, —CO$_2$$R^{11a}$, —C(O)N($R^{11a}$)$_2$, —C(O)N($R^{11a}$)—O$R^{11a}$, —SO$_2$$R^{11a}$, —SO$_2$N($R^{11a}$)$_2$, or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

wherein each occurrence of $R^{11a}$ is independently hydrogen or an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

provided that:

a. when $G_1$ is N, $R^1$ is CONH$_2$, $R^2$ is phenyl substituted with a para-piperazin-1-yl group or a para-methoxy group, then HY is a group other than 4-pyridinyl or 3-pyridinyl;

b. when HY is unsubstituted 3-pyridinyl, then neither $R^1$ nor $R^2$ is CN or unsubstituted piperidinyl;

c. when HY is 4-pyridinyl, then HY is not tetra substituted; and d. the compound is other than:

2-Pyrimidinamine, 4-[4-(4-fluorophenyl)-2-(4-pyridinyl)-5-oxazolyl]-N-[(1S)-1-phenylethyl]-;

Ethanone, 1-[5-(4-chlorophenyl)-2-(4-pyridinyl)-4-oxazolyl]-;

Pyridine, 4-[4-chloro-5-[4-(trichloromethyl)phenyl]-2-oxazolyl]-;

Benzenepropanamide, α-[[4-[5-(3,4-dichlorophenyl)-2-(3-pyridinyl)-4-oxazolyl]benzoyl]amino]-, (αS)-;

Benzoic acid, 4-[5-(3,4-dichlorophenyl)-2-(3-pyridinyl)-4-oxazolyl]-, methyl ester;

Benzoic acid, 4-[5-(3,4-dichlorophenyl)-2-(3-pyridinyl)-4-oxazolyl]-;

Pyridine, 3-[4-(4-chlorophenyl)-5-(4-methylphenyl)-2-oxazolyl]-4-methyl-;

Pyridinium, 4-[4,5-bis(4-methoxyphenyl)-2-oxazolyl]-1-methyl-, perchlorate; or

Benzenamine, 4-[5-(4-chlorophenyl)-2-(4-pyridinyl)-4-oxazolyl]-N,N-dimethyl-.

2. The compound of claim 1, wherein $R^1$ is CY.

3. The compound of claim 1, wherein $R^1$ is CY and CY is

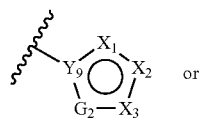

i-a or

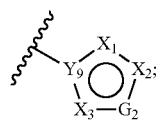

ii-a wherein:

$X_1$, $X_2$, and $X_3$, are each independently N, O, S, $NR^{4'}$, or $CR^7$, provided that only one of $X_1$, $X_2$, or $X_3$ may be O or S;

$Y_9$ is N or C;

$G_2$ is $CR^{7'}$, —N= or —$NR^{4'}$—, wherein:

$R^{4'}$ is independently hydrogen, —$Z_2$—$R^6$, optionally substituted $C_{1-6}$ aliphatic, or optionally substituted 3-10-membered cycloaliphatic, wherein:

$Z_2$ is selected from an optionally substituted $C_{1-3}$ alkylene chain, —S(O)—, —S(O)$_2$—, —C(O)—, —CO$_2$—, —C(O)$NR^{4a}$-, and —S(O)$_2NR^{4a}$-, $R^{4a}$ is hydrogen or an optionally substituted $C_{1-4}$ aliphatic, and $R^6$ is an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^7$ and $R^{7'}$ is independently hydrogen, —CN, halogen, —$Z_3$—$R^8$, $C_{1-6}$ aliphatic, or 3-10-membered cycloaliphatic, wherein:

$Z_3$ is selected from an optionally substituted $C_{1-3}$ alkylene chain, —O—, —N($R^{7a}$)—, —S—, —S(O)—, —S(O)$_2$—, —C(O)—, —CO$_2$—, —C(O)$NR^{7a}$-, —N($R^{7a}$)C(O)—, —N($R^{7a}$)CO$_2$—, —S(O)$_2NR^{7a}$-, —N($R^{7a}$)S(O)$_2$—, —OC(O)N($R^{7a}$)—, —N($R^{7a}$)C(O)$NR^{7a}$-, —N($R^{7a}$)S(O)$_2$N($R^{7a}$)—, and —OC(O)—;

$R^{7a}$ is hydrogen or an optionally substituted $C_{1-4}$ aliphatic, and $R^8$ is an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur.

4. The compound of claim 1, wherein $R^1$ is CY and CY is

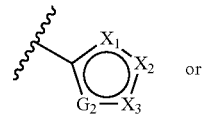

i or

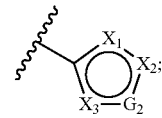

ii wherein:

$X_1$, $X_2$, and $X_3$, are each independently N, O, S, $NR^{4'}$, or $CR^7$, provided that only one of $X_1$, $X_2$, or $X_3$ may be O or S, $G_2$ is $CR^{7'}$, —N= or —$NR^{4'}$—, wherein:

$R^{4'}$ is independently H, —$Z_2$—$R^6$, optionally substituted $C_{1-6}$ aliphatic, or optionally substituted 3-10-membered cycloaliphatic, wherein:

$Z_2$ is selected from an optionally substituted $C_{1-3}$ alkylene chain, —S(O)—, —S(O)$_2$—, —C(O)—, —CO$_2$—, —C(O)$NR^{4a}$-, and —S(O)$_2NR^{4a}$-, $R^{4a}$ is hydrogen or an optionally substituted $C_{1-4}$ aliphatic, and $R^6$ is an optionally substituted group selected from $C_{1-6}$ aliphatic, 3-10 membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur;

each occurrence of $R^7$ or $R^{7'}$ is independently hydrogen, —CN, halogen, —$Z_3$—$R^8$, $C_{1-6}$ aliphatic, or 3-10-membered cycloaliphatic, wherein:

$Z_3$ is selected from an optionally substituted $C_{1-3}$ alkylene chain, —O—, —N($R^{7a}$)—, —S—, —S(O)—, —S(O)$_2$—, —C(O)—, —CO$_2$—, —C(O)$NR^{7a}$-, —N($R^{7a}$)C(O)—, —N($R^{7a}$)CO$_2$—, —S(O)$_2NR^{7a}$-, —N($R^{7a}$)S(O)$_2$—, —OC(O)N($R^{7a}$)—, —N($R^{7a}$)C(O)$NR^{7a}$-, —N($R^{7a}$)S(O)$_2$N($R^{7a}$)—, and —OC(O)—, $R^{7a}$ is hydrogen or an optionally substituted $C_{1-4}$ aliphatic, and $R^8$ is an optionally substituted group selected from $C_{1-6}$ aliphatic, 3-10-membered cycloaliphatic, 4-10-membered heterocyclyl having 1-5 heteroatoms independently selected from nitrogen, oxygen, and sulfur, 6-10-membered aryl, and 5-10-membered heteroaryl having 1-5 heteroatoms independently selected from nitrogen, oxygen, and sulfur.

5. The compound of claim 4, wherein $R^1$ is CY; and CY is

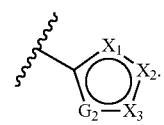

i

6. The compound of claim 4, wherein $R^1$ is CY; and CY is

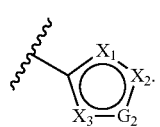

ii

7. The compound of claim 5 or 6, wherein $X_1$ and $X_2$ are N, $G_2$ is $N(R^{4'})$, and $X_3$ is CH.

8. The compound of claim 5 or 6, wherein $X_1$ and $G_2$ are N, $X_3$ is $N(R^{4'})$, and $X_2$ is CH.

9. The compound of claim 1, wherein $R^1$ is a substituted phenyl or an optionally substituted heteroaryl ring.

10. The compound of claim 1, wherein HY is selected from:

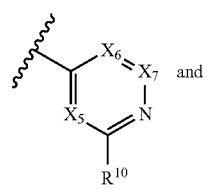

H

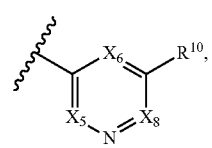

J wherein each occurrence of $X_5$, $X_6$, and $X_7$ is independently —$CR^{10}$ or N, provided no more than two occurrences of $X_5$, $X_6$, and $X_7$ are N;

each occurrence of $Q_1$ and $Q_2$ is independently S, O or —$NR^9$;

each occurrence of $Y_1$, $Y_7$, and $Y_8$ is independently —$CR^{10}$ or N;

or wherein two adjacent occurrences of $X_6$, and $X_7$, $Y_1$ and $Q_1$, or two adjacent occurrences of $R^{10}$, taken together with the atom to which they are bound, form an optionally substituted fused group selected from phenyl or 5-6-membered heteroaryl having 1-5 heteroatoms independently selected from nitrogen, oxygen, and sulfur.

11. The compound of claim 10, wherein HY is selected from:

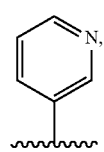

v

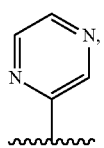

vi

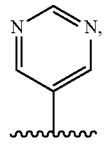

vii

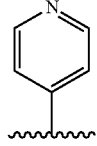

ix

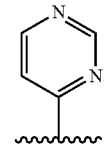

x

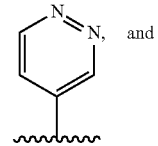

xi and

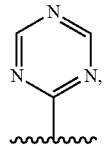

xii wherein each HY group is optionally additionally substituted with one or more occurrences of $R^{10}$.

12. The compound of claim 10, wherein HY is selected from:

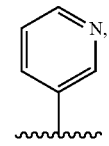

v

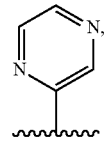

vi

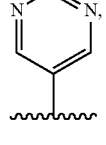

vii

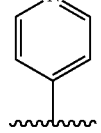

ix

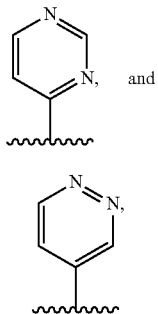

wherein each HY group is optionally additionally substituted with one or more occurrences of $R^{10}$.

13. The compound of claim 12, wherein HY is

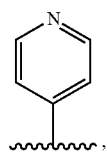

wherein HY is additionally optionally substituted with one or more occurrences of $R^{10}$.

14. The compound of claim 1, wherein HY is

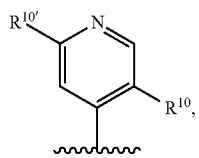

wherein $R^{10'}$ is $NHCOR^{10c}$ or $-NHCOOR^{10c}$.

15. The compound of claim 1, wherein HY is

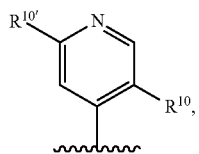

wherein $R^{10'}$ is $NHCOR^{10c}$.

16. The compound of claim 15, wherein HY is

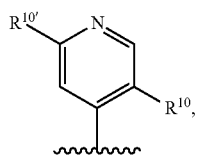

wherein $R^{10'}$ is hydrogen, methyl, chloro, bromo, fluoro, CN, $CF_3$, $OR^{10c}$, $COR^{10a}$, and $R^{10'}$ is $NHCOR^{10c}$ or $-NHCOOR^{10c}$.

17. The compound of claim 1, wherein $G_1$ is $CR^3$.
18. The compound of claim 1, wherein $G_1$ is CH.

19. The compound of claim 1, wherein $R^2$ is a 6-10-membered aryl or 5-10-membered heteroaryl having 1-5 heteroatoms independently selected from nitrogen, oxygen, and sulfur; substituted with 1-3 occurrences of $R^{2a}$.

20. The compound of claim 19, wherein $R^2$ is a phenyl group substituted with one or more independent occurrences of halogen, $C_{1-3}$ alkyl, $C_{3-6}$ cycloalkyl, $C_{3-6}$ heterocyclyl, $-CN$, $C_{1-3}$ haloalkyl, $-(CH_2)_pN(R^{12b})_2$, $-OR^{12b}$, $-NHC(O)R^{12b}$, $-NHC(O)NHR^{12b}$, $-NHS(O)_2R^{12b}$, $C(O)OR^{12b}$, $-C(O)N(R^{12b})_2$, or $-C(O)R^{12b}$.

21. The compound of claim 20, wherein $R^2$ is a phenyl group optionally substituted with one or more independent occurrences of halogen, $C_{1-3}$ alkyl, $-CN$, $C_{1-3}$ haloalkyl, $-CH_2N(R^{12b})_2$, $-OC_{1-3}$ alkyl, $-OC_{1-3}$ haloalkyl, $-NHC(O)C_{1-3}$ alkyl, $-NHC(O)NHC_{1-3}$ alkyl, $-NHS(O)_2C_{1-3}$ alkyl, or $-C(O)H$.

22. The compound of claim 20, wherein $R^2$ is a phenyl group substituted with one or more independent occurrences of halogen, $C_{1-3}$ alkyl, $-CN$, $C_{1-3}$ haloalkyl, $-CH_2N(CH_3)_2$, $-OC_{1-3}$ alkyl, $-OC_{1-3}$ haloalkyl, $-NHC(O)C_{1-3}$ alkyl, $-NHC(O)NHC_{1-3}$ alkyl, $-NHS(O)_2C_{1-3}$ alkyl, or $-C(O)H$.

23. The compound of claim 20, wherein $R^2$ is a phenyl group substituted with 1 or 2 occurrences of halogen.

24. The compound of claim 20, wherein $R^2$ is a phenyl group substituted with 1 occurrence of halogen.

25. The compound of claim 24, wherein the halogen is Cl.

26. A composition comprising a compound of claim 1, or a pharmaceutically acceptable salt thereof, and a pharmaceutically acceptable carrier.

27. A compound selected from:

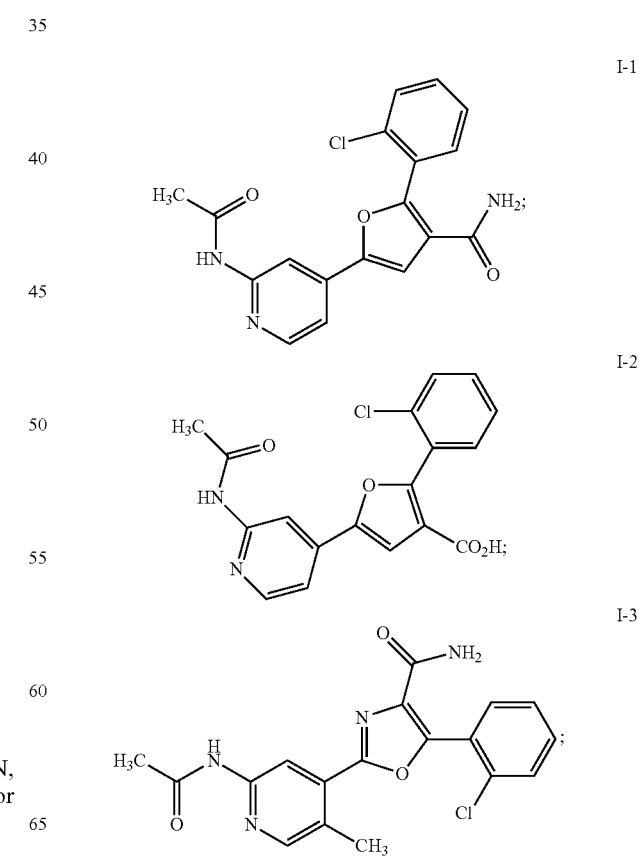

-continued

I-4, I-5, I-6, I-7, I-8, I-9, I-10, I-11, I-12, I-13

I-14
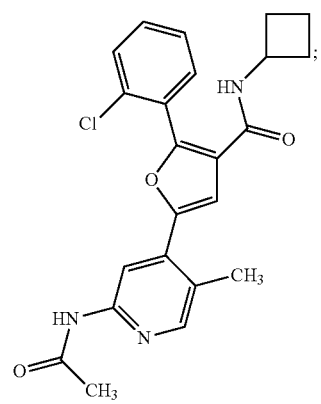
I-15
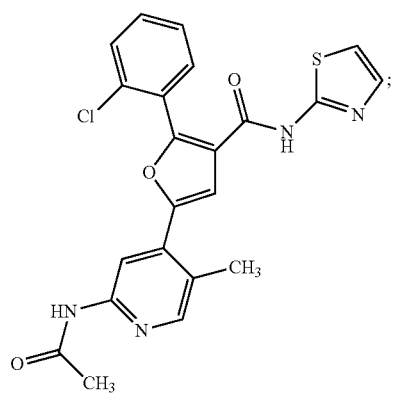
I-16
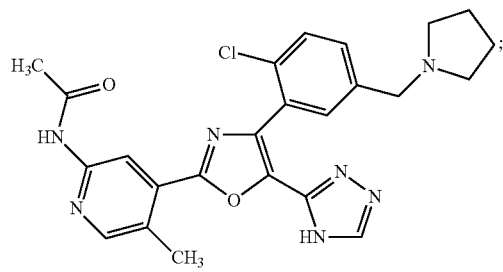
I-17
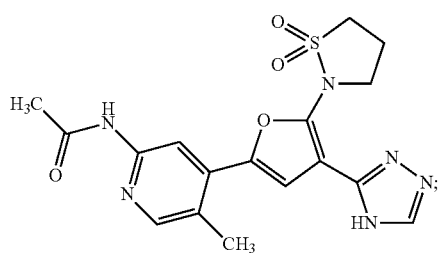
I-18
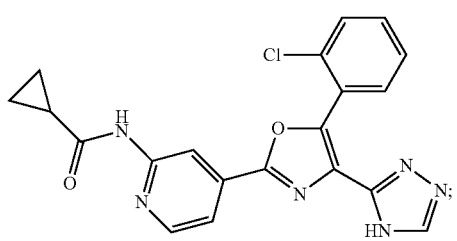
I-19
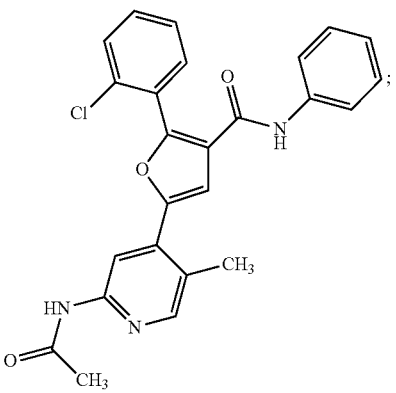
I-20
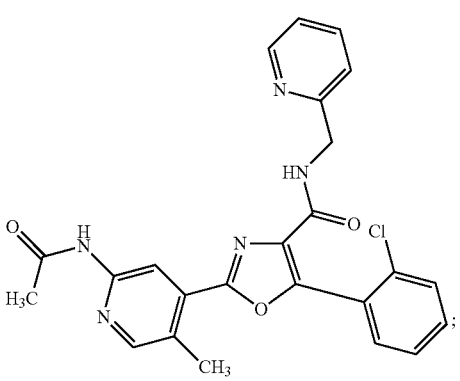
I-21
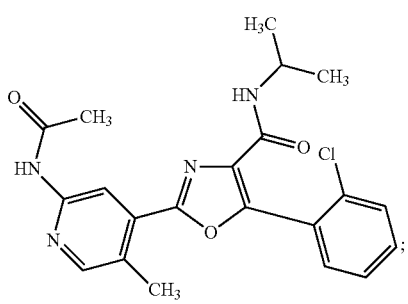
I-22
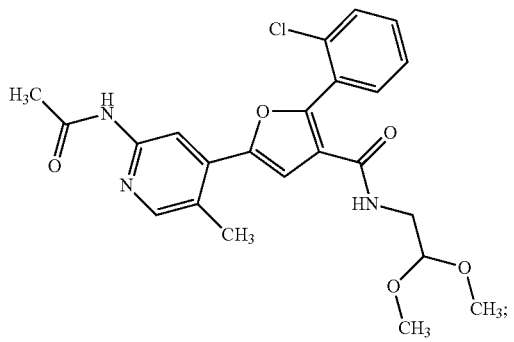

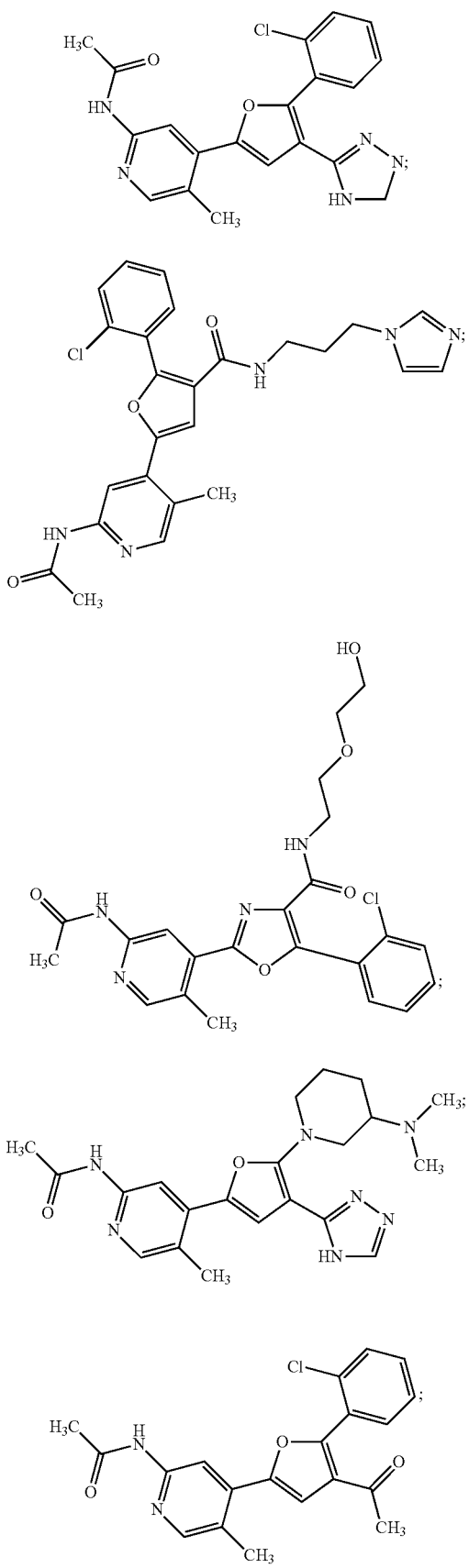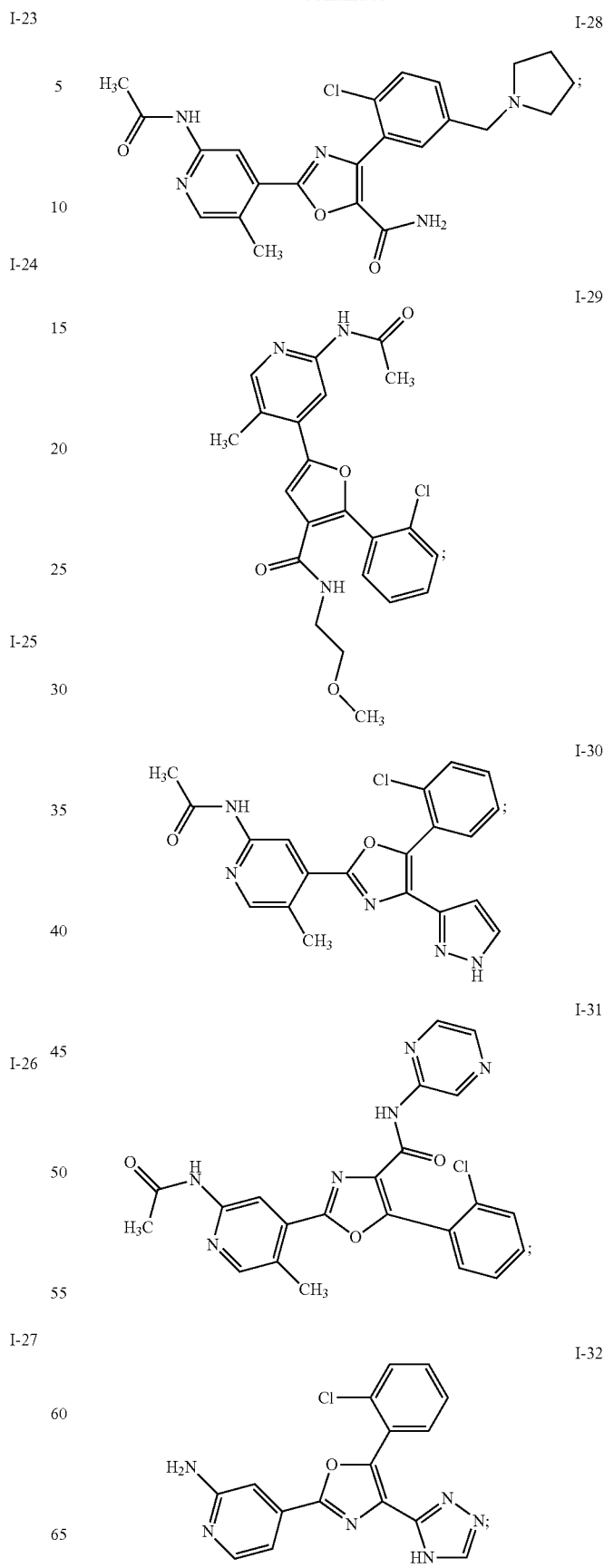

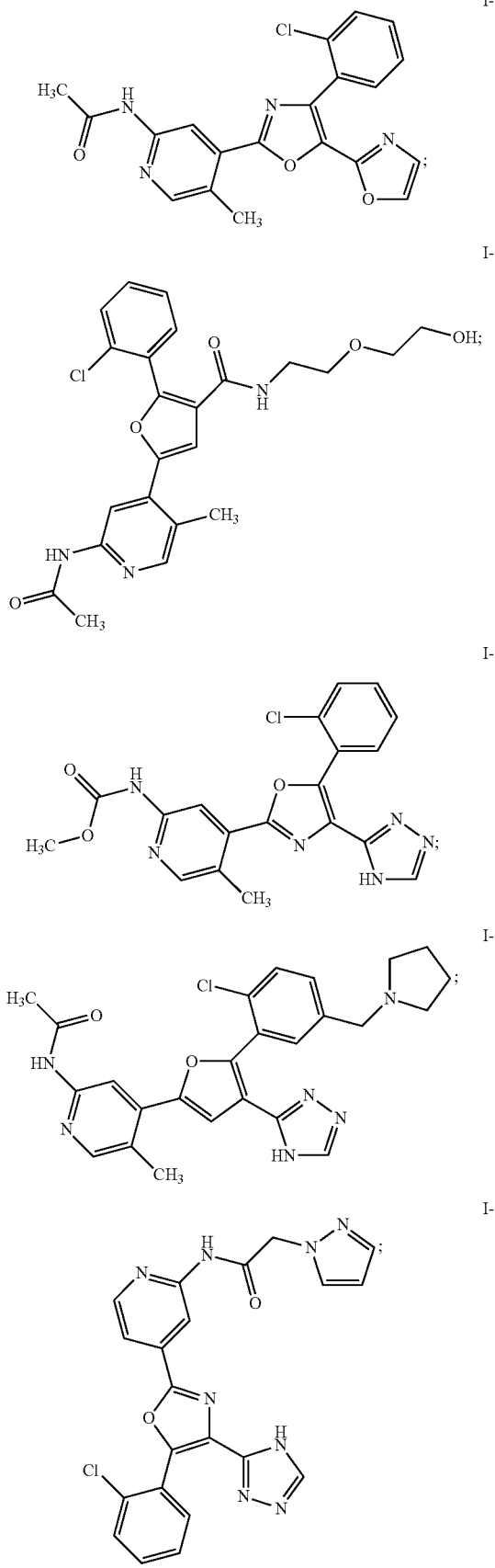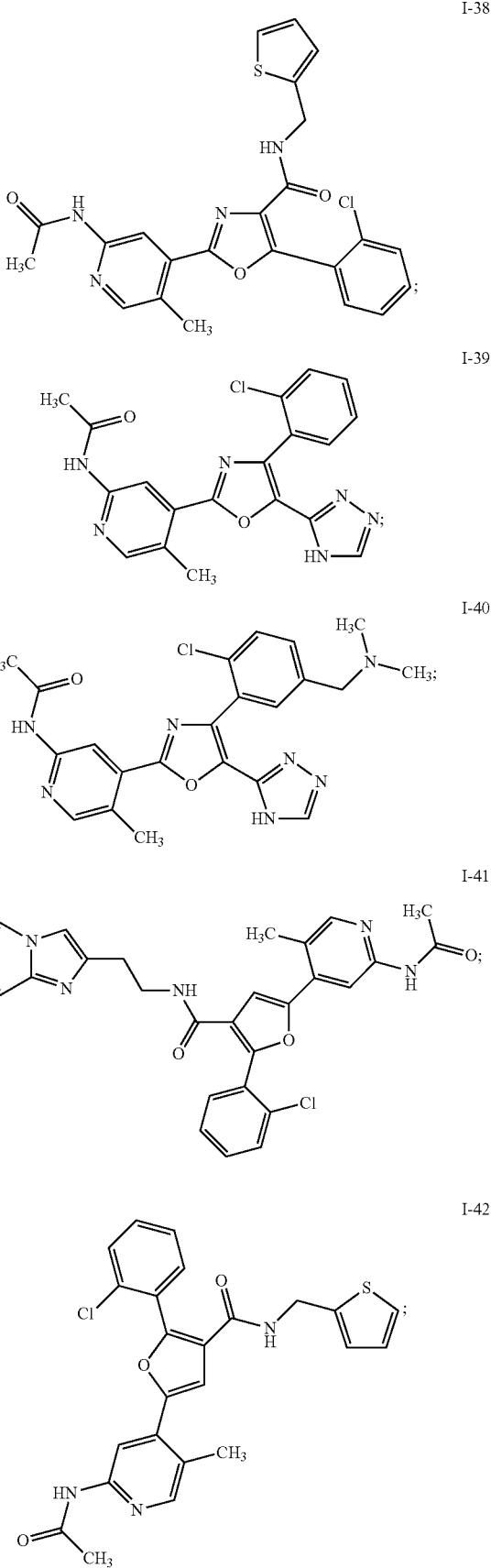

-continued
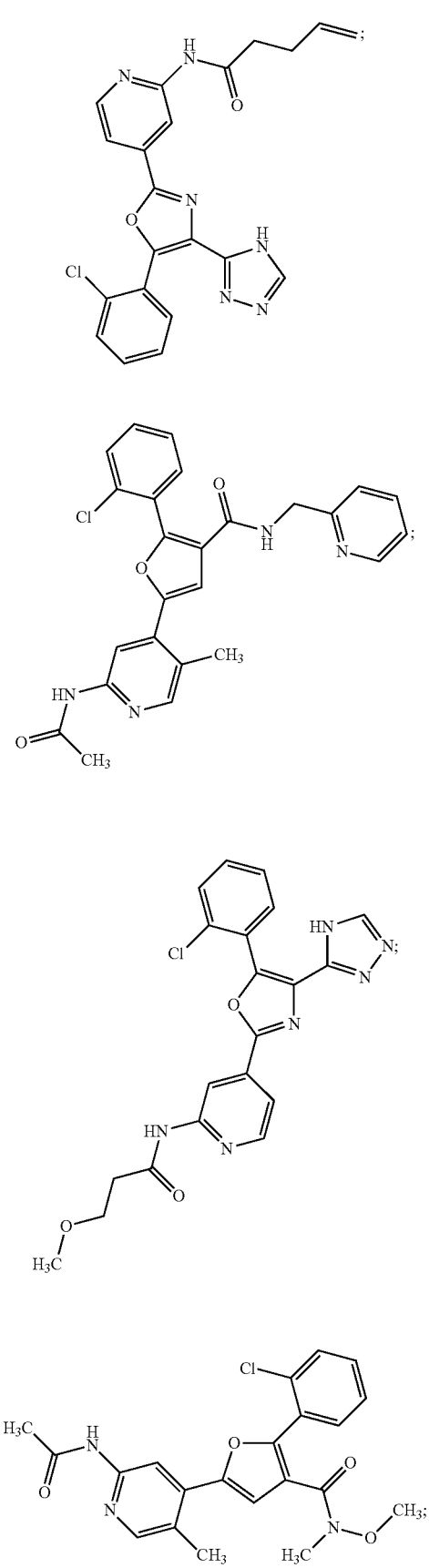
I-43
I-44
I-45
I-46
-continued
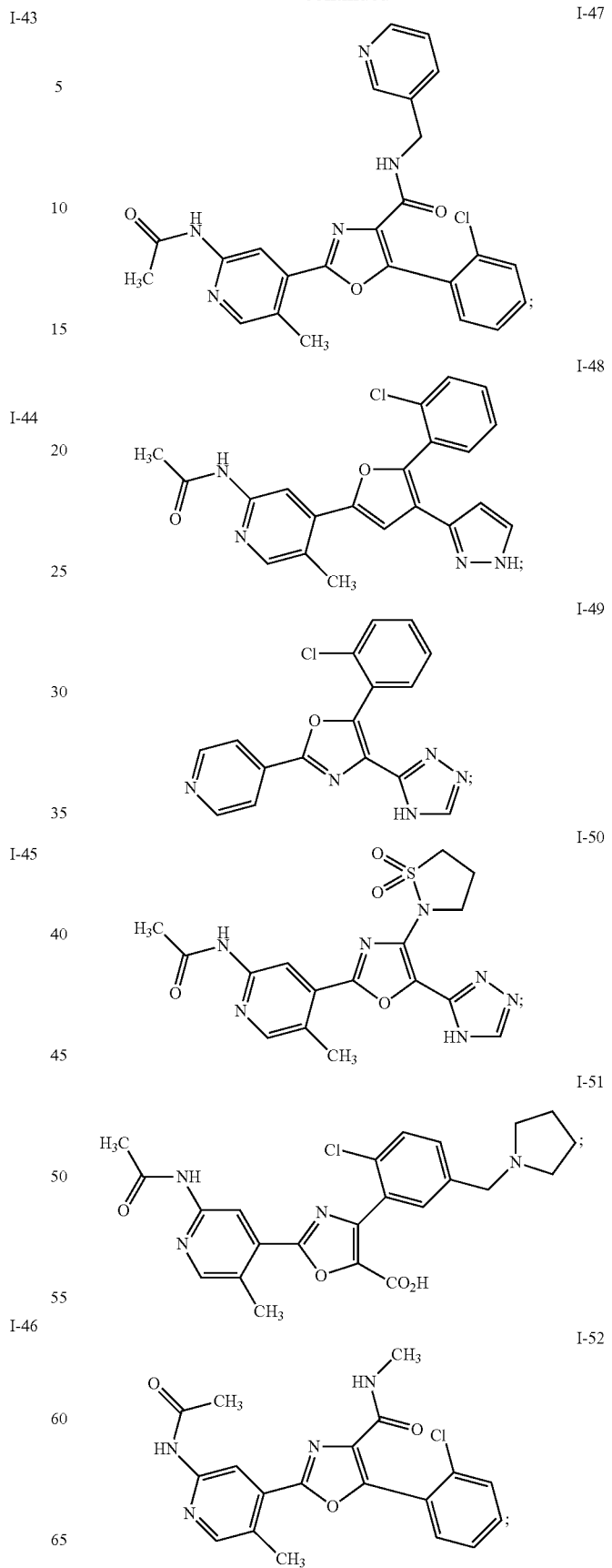
I-47
I-48
I-49
I-50
I-51
I-52

I-53 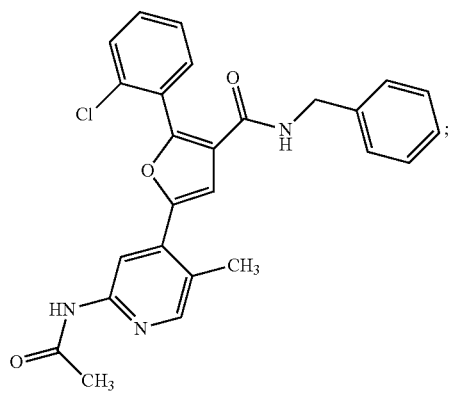
I-54 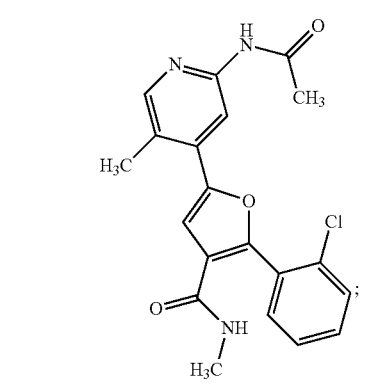
I-55 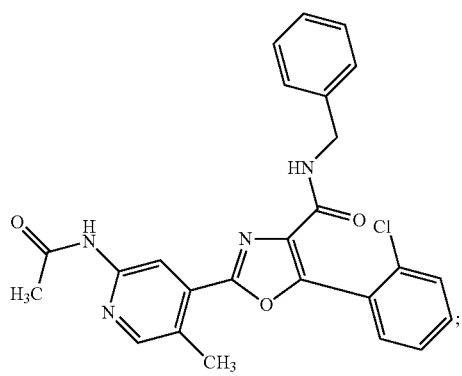
I-56 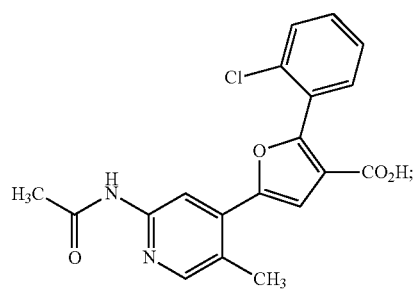
I-57 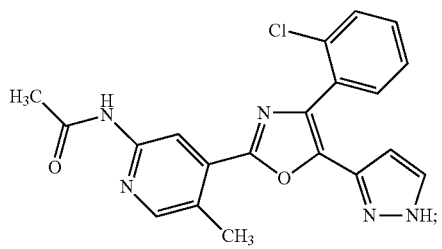
I-58 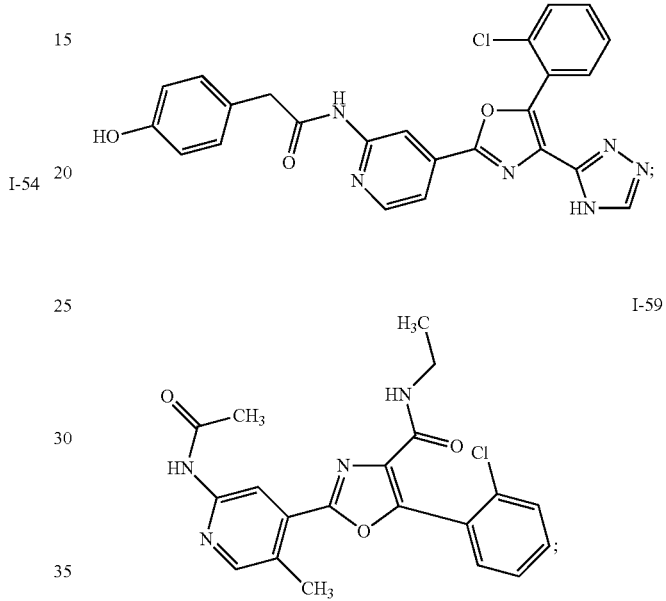
I-59 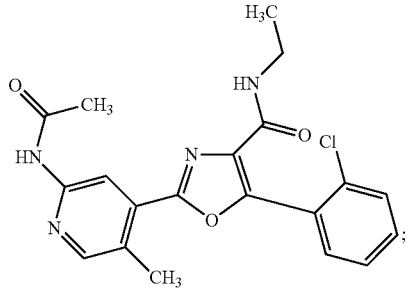
I-60 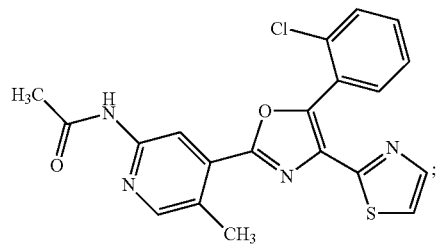
I-61 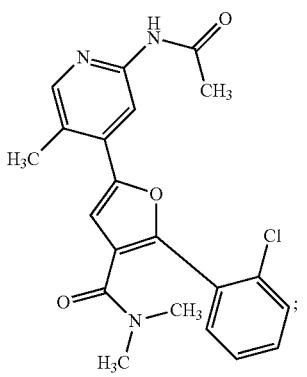

I-62
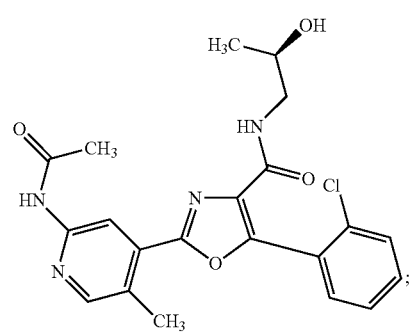
I-63
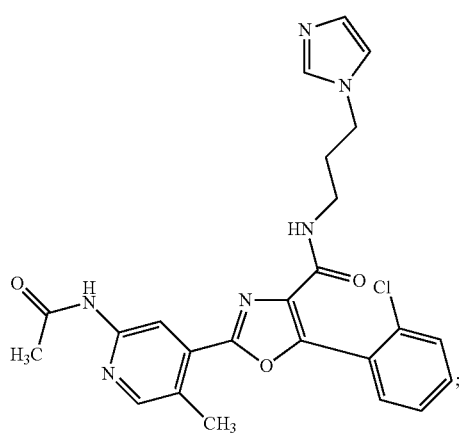
I-64
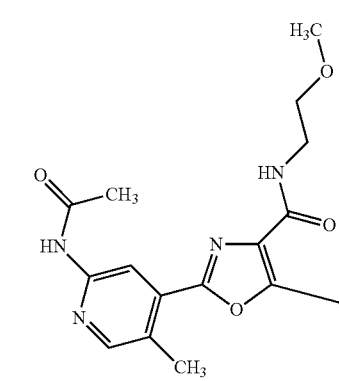
I-65
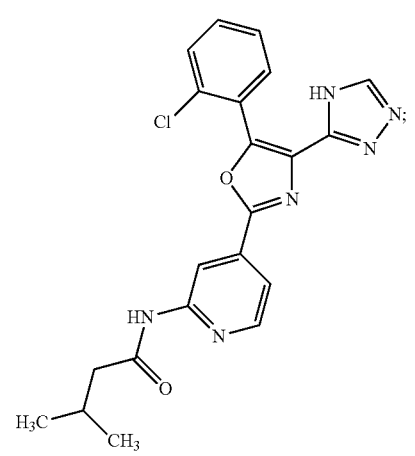
I-66
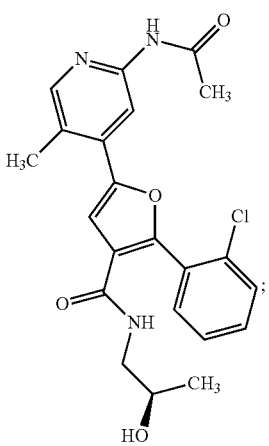
I-67
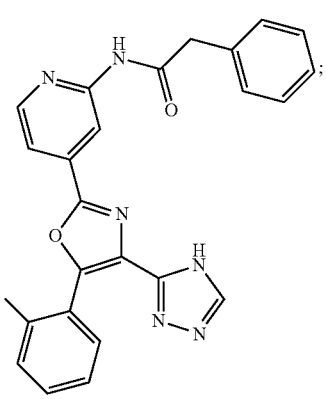
I-68
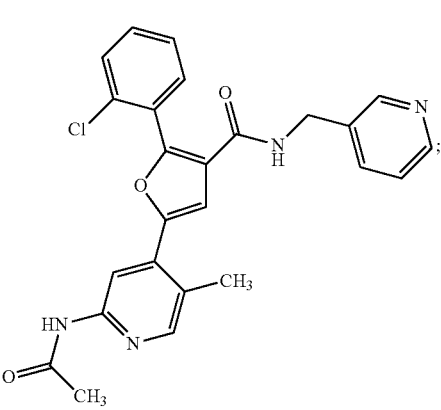
I-69
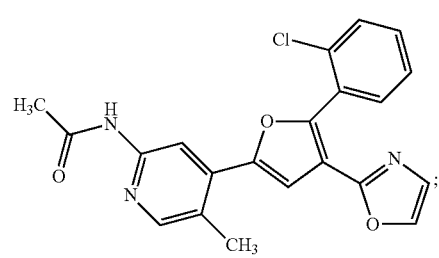

-continued
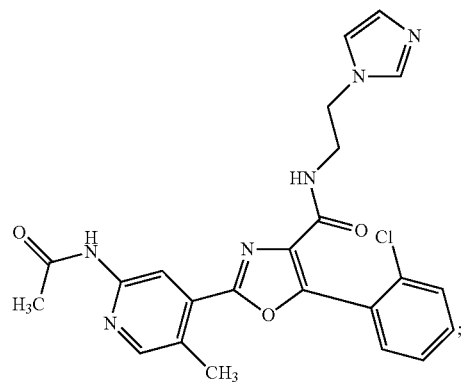
I-70
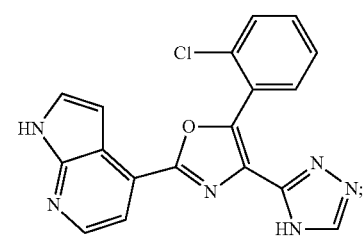
I-71
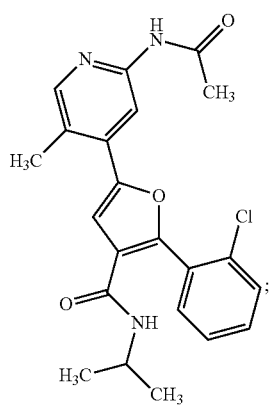
I-72
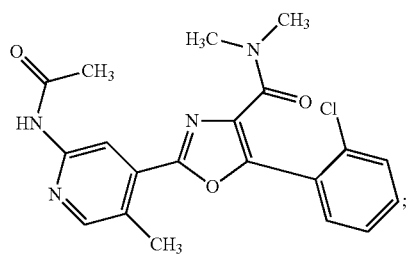
I-73
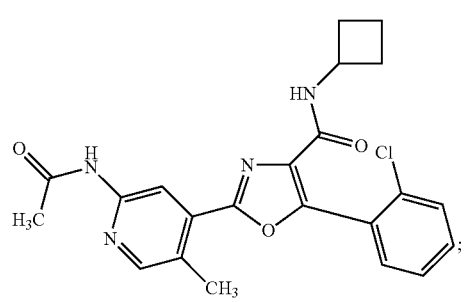
I-74
-continued
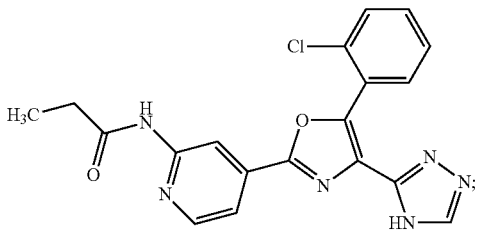
I-75
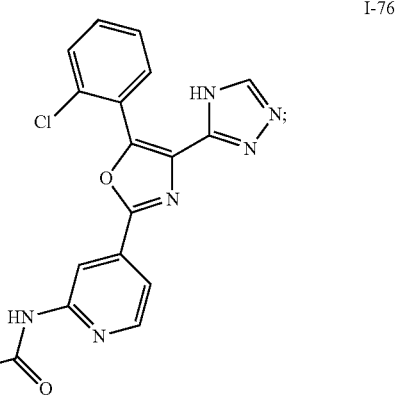
I-76
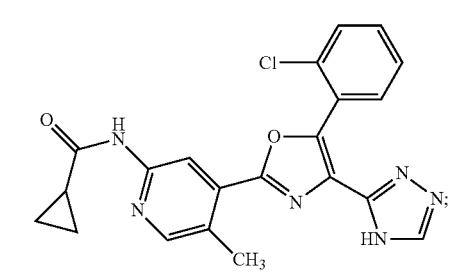
I-77
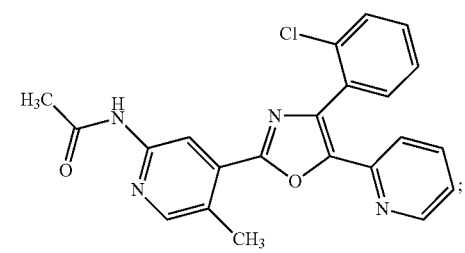
I-78
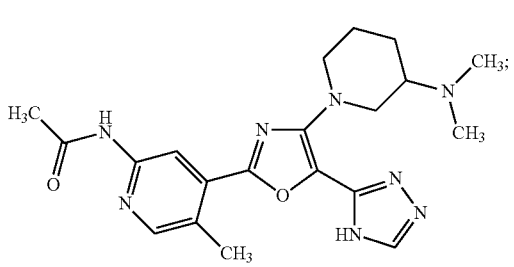
I-79

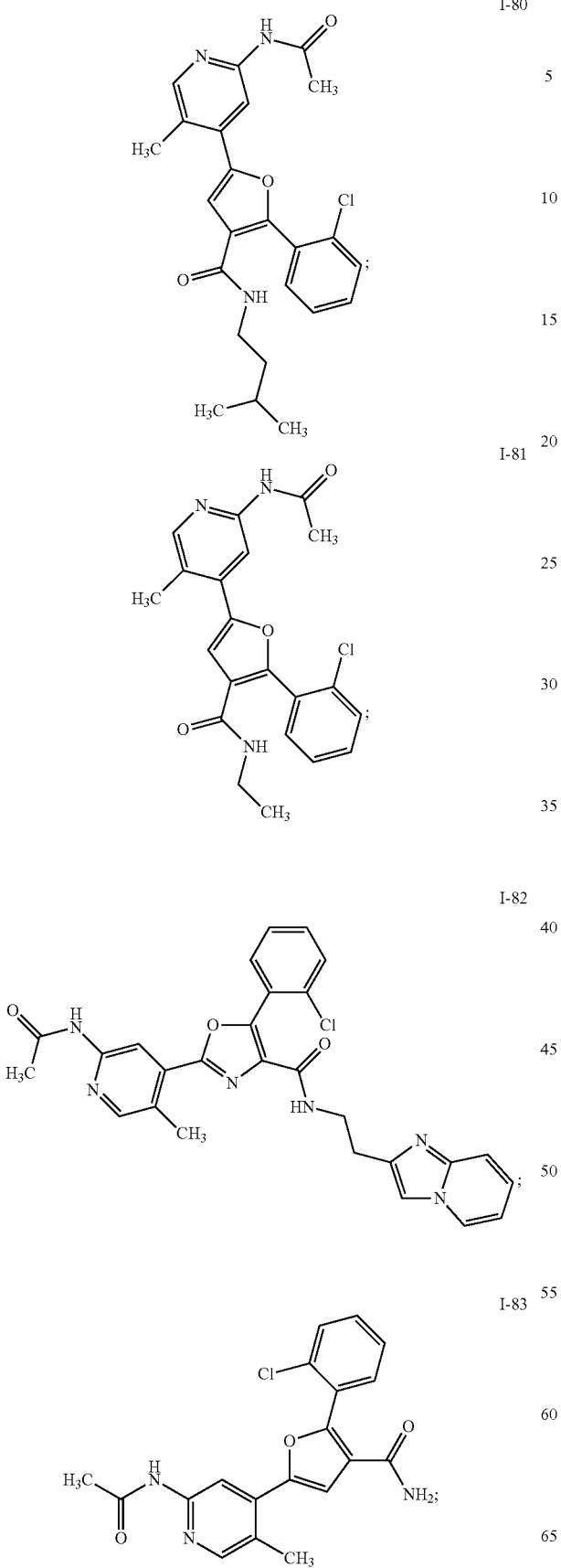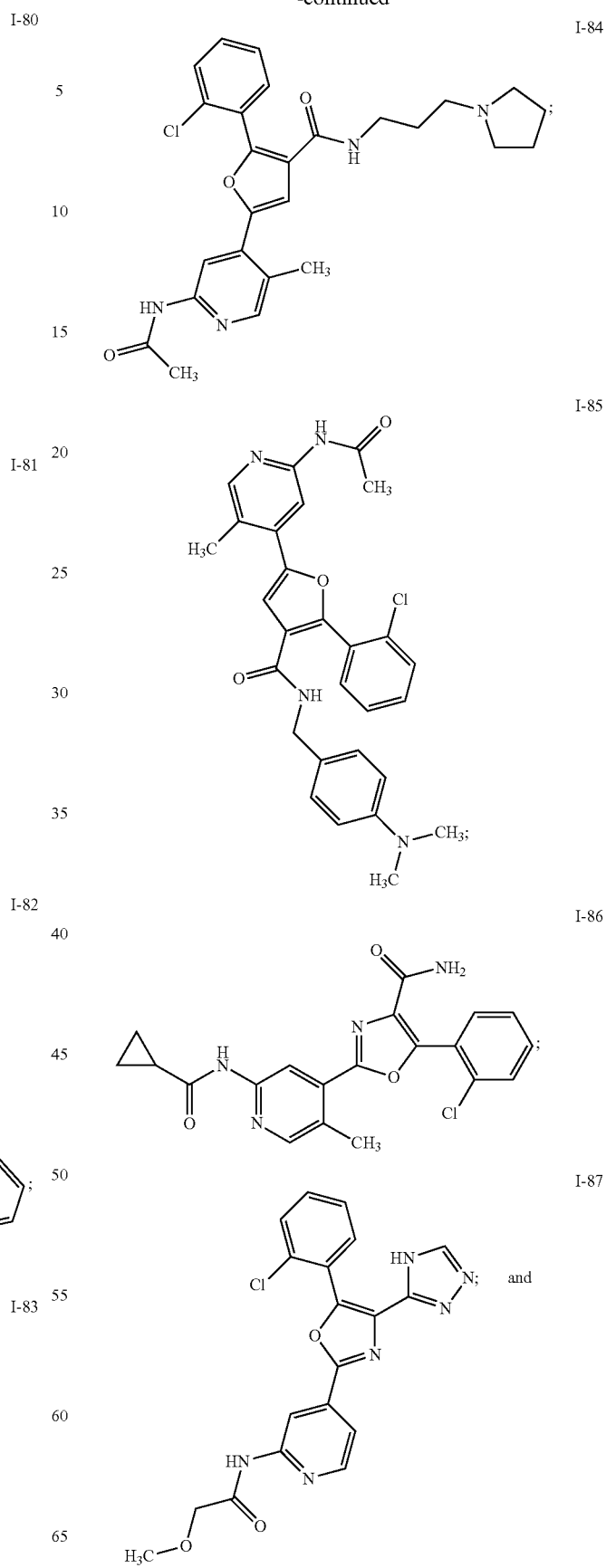

I-88
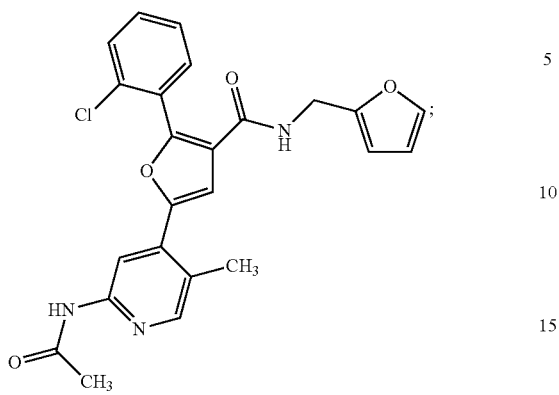
or a pharmaceutically acceptable salt thereof.
28. A composition comprising a compound of claim 27, or a pharmaceutically acceptable salt thereof, and a pharmaceutically acceptable carrier.
* * * * *